(12) United States Patent
Yamamoto et al.

(10) Patent No.: US 10,407,378 B2
(45) Date of Patent: Sep. 10, 2019

(54) COMPOUND, AND FLAVOR AND/OR FRAGRANCE COMPOSITION CONTAINING SAID COMPOUND

(71) Applicant: TAKASAGO INTERNATIONAL CORPORATION, Tokyo (JP)

(72) Inventors: Kenichi Yamamoto, Hiratsuka (JP); Takashi Aida, Hiratsuka (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 344 days.

(21) Appl. No.: 15/303,590

(22) PCT Filed: Mar. 9, 2015

(86) PCT No.: PCT/JP2015/056793
§ 371 (c)(1),
(2) Date: Oct. 12, 2016

(87) PCT Pub. No.: WO2015/163023
PCT Pub. Date: Oct. 29, 2015

(65) Prior Publication Data
US 2017/0029358 A1    Feb. 2, 2017

(30) Foreign Application Priority Data
Apr. 21, 2014   (JP) ................. 2014-087538

(51) Int. Cl.
| | |
|---|---|
| *C07C 69/75* | (2006.01) |
| *A61Q 19/10* | (2006.01) |
| *A23L 27/20* | (2016.01) |
| *A61K 8/37* | (2006.01) |
| *A61Q 13/00* | (2006.01) |
| *C07C 69/54* | (2006.01) |
| *C11D 3/50* | (2006.01) |
| *A61Q 5/02* | (2006.01) |
| *C11B 9/00* | (2006.01) |
| *C07C 69/02* | (2006.01) |
| *C07C 69/22* | (2006.01) |
| *C07C 69/533* | (2006.01) |

(52) U.S. Cl.
CPC .......... *C07C 69/75* (2013.01); *A23L 27/2024* (2016.08); *A61K 8/37* (2013.01); *A61Q 5/02* (2013.01); *A61Q 13/00* (2013.01); *A61Q 19/10* (2013.01); *C07C 69/02* (2013.01); *C07C 69/22* (2013.01); *C07C 69/533* (2013.01); *C07C 69/54* (2013.01); *C11B 9/003* (2013.01); *C11B 9/0034* (2013.01); *C11B 9/0061* (2013.01); *C11D 3/50* (2013.01); *C07C 2601/02* (2017.05); *C07C 2601/04* (2017.05); *C07C 2601/14* (2017.05); *C07C 2601/16* (2017.05)

(58) Field of Classification Search
CPC ........ A61K 8/37; C11D 3/50; C07C 2601/02; A23L 27/204; A23L 27/203
See application file for complete search history.

(56) References Cited

U.S. PATENT DOCUMENTS

| | | | | |
|---|---|---|---|---|
| 4,435,428 | A | * 3/1984 | Boden | ....... A23G 4/06 131/276 |
| 4,481,225 | A | * 11/1984 | Boden | ....... A23G 4/06 426/536 |
| 4,521,331 | A | 6/1985 | Martel et al. | |
| 5,767,305 | A | * 6/1998 | Monteleone | ........ C07C 69/74 512/22 |

(Continued)

FOREIGN PATENT DOCUMENTS

| | | |
|---|---|---|
| JP | 58-090529 A | 5/1983 |
| JP | 2003-012587 A | 1/2003 |

(Continued)

OTHER PUBLICATIONS

Motoichi Indo, "Synthetic Flavors and/or Fragrances", Chemistry and Product Knowledge, 2005, pp. 391-419.

Janine Cossy, et al., "Stereoselective Synthesis of Cyclopropanes Bearing Adjacent Stereocenters", Synthesis, 1999, pp. 1063-1075, No. 6.

Hiromasa Kiyota, et al., "Syntheses and odour descriptions of cyclopropanated compounds 3. Analogues of leaf alcohol, its esters and leaf acetal", Flavour and Fragrance Journal, 2002, pp. 227-231, vol. 17.

(Continued)

*Primary Examiner* — Nikki H. Dees
(74) *Attorney, Agent, or Firm* — Sughrue Mion, PLLC

(57) ABSTRACT

The present invention provides a compound represented by general formula (1).

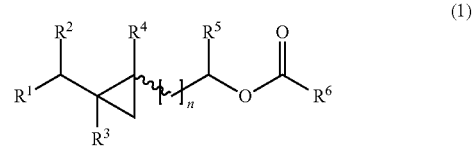

(1)

(In the formula, $R^1$ represents an alkyl group having 2 to 9 carbon atoms, an alkenyl group having 2 to 9 carbon atoms, a cyclic alkyl group having 3 to 10 carbon atoms which may have a substituent, or a phenyl group which may have a substituent; $R^2$ represents an alkyl group having 1 to 3 carbon atoms; $R^3$ to $R^5$ independently represent a hydrogen atom, or an alkyl group having 1 to 3 carbon atoms; $R^6$ represents an alkyl group having 1 to 5 carbon atoms, an alkenyl group having 2 to 5 carbon atoms, a cyclic alkyl group having 3 to 10 carbon atoms which may have a substituent, or an alkoxy group having 1 to 5 carbon atoms; n represents 0 or 1; and the wavy line represents a cis form, a trans form or a mixture of a cis form and a trans form.)

8 Claims, No Drawings

(56) References Cited

U.S. PATENT DOCUMENTS

| | | | |
|---|---|---|---|
| 7,323,606 B2* | 1/2008 | Turin | C07C 33/05 424/65 |
| 8,030,524 B2* | 10/2011 | Bajgrowicz | C07C 31/13 512/18 |
| 8,409,649 B2* | 4/2013 | Ungureanu | A23L 2/56 424/48 |
| 8,609,603 B2* | 12/2013 | Smets | A61K 8/738 512/1 |
| 2003/0089885 A1 | 5/2003 | Rogers et al. | |
| 2004/0186043 A1 | 9/2004 | Williams | |
| 2004/0234568 A1 | 11/2004 | Kraft et al. | |
| 2006/0046955 A1 | 3/2006 | Kraft | |
| 2006/0052277 A1 | 3/2006 | Kraft | |
| 2007/0225201 A1 | 9/2007 | Kraft | |
| 2007/0264340 A1* | 11/2007 | Turin | A61K 8/33 424/484 |
| 2010/0069508 A1 | 3/2010 | Bajgrowicz | |
| 2011/0308556 A1* | 12/2011 | Smets | A61K 8/738 134/26 |
| 2015/0038386 A1 | 2/2015 | Dang et al. | |

FOREIGN PATENT DOCUMENTS

| | | |
|---|---|---|
| JP | 2004-285357 A | 10/2004 |
| JP | 2004-535412 A | 11/2004 |
| JP | 2006-508153 A | 3/2006 |
| JP | 2006-508175 A | 3/2006 |
| JP | 2007-536285 A | 12/2007 |
| JP | 2011-037761 A | 2/2011 |
| WO | 2012/160189 A1 | 11/2012 |

OTHER PUBLICATIONS

International Searching Authority, International Search Report for PCT/JP2015/056793 dated May 26, 2015 [PCT/ISA/210].
International Searching Authority, Written Opinion for PCT/JP2015/056793 dated May 26, 2015 [PCT/ISA/237].

* cited by examiner

COMPOUND, AND FLAVOR AND/OR FRAGRANCE COMPOSITION CONTAINING SAID COMPOUND

CROSS REFERENCE TO RELATED APPLICATIONS

This application is a National Stage of International Application No. PCT/JP2015/056793 filed Mar. 9, 2015, claiming priority based on Japanese Patent Application No. 2014-087538 filed Apr. 21, 2014, the contents of all of which are incorporated herein by reference in their entirety.

The present invention relates to a novel compound having a cyclopropane ring structure, and a flavor and/or fragrance composition comprising the compound. The present invention also relates to a beverage, food, cosmetic, toiletry product, air-care product, daily-necessity or grocery product, oral-care composition, hair-care product, skin-care product, body-care product, laundry detergent, finishing softener for clothes, quasi drug, or drug comprising the flavor and/or fragrance composition, and a method for strengthening an odor of a flavor and/or fragrance.

BACKGROUND ART

The recent product diversification of cosmetics, health and sanitary materials, drugs, and the like have caused an unprecedentedly high demand for development of flavor and/or fragrance substances which are to be used for cosmetics, flavors and/or fragrances for health and sanitary materials, and further flavors and/or fragrances for drugs and which are high in diffusibility, unique in odor quality, highly preferred, high in fixation ability, good in stability, and high in safety. Especially, numerous compounds with musky odor have been developed so far (for example, GOUSEI KOURYOU, KAGAKU TO SHOUHIN CHISHIKI (Synthetic Flavors and/or Fragrances, Chemistry and Product Knowledge)<enlarged and revised edition> (authored by Indo Motoichi), The Chemical Daily Co., Ltd., pp. 391 to 419, the enlarged and revised edition being published on Mar. 22, 2005). These compounds have been developed for the reason that natural musk flavors and/or fragrances are difficult to obtain from the viewpoint of animal protection, and for the purpose of meeting the shifting trend of odor.

Compounds having musky odor reported so far include macrocyclic musks (muscone, civetone, ethylene brassylate, etc.), nitro-musks (Musk xylol, Musk ambrette, Musk ketone, etc.), polycyclic musks (tetralin musk, indane musk, isocoumarin musk, etc.), alicyclic musks (see, for example, Published Japanese Translation of PCT International Application No. 2004-535412, Japanese Patent Application Publication No. 2004-285357, Published Japanese Translation of PCT International Application No. 2006-508153, Published Japanese Translation of PCT International Application No. 2006-508175, Published Japanese Translation of PCT International Application No. 2007-536285, and Japanese Patent Application Publication No. 2011-37761), and the like.

Meanwhile, some compounds having a cyclopropane ring are known to be useful as raw materials for compound flavors and/or fragrances. For example, [(1S*,2R*)-1-methyl-2-[(R*)-5-methyl-4-hexen-2-yl]cyclopropyl]methanol has a rose-like odor with a floral note similar to those of citrus and 3-methyl-5-phenyl-1-pentanol (International Patent Application Publication No. WO2012/160189). In addition, 1-methyl-2-[[(1R)-2,2,3-trimethylcyclopentyl]methyl]cyclopropyl]methanol has an sandalwood-like odor with a natural nuance (United States Patent Application Publication No. 2010/069508) In addition, (1S*,2S*)-2-((R*)-1-phenylethyl)cyclopropylmethanol and the like are known as compounds having a cyclopropane ring and a benzene ring, although the odors thereof are not described (Synthesis (1999), No. 6, pp. 1063-1075).

SUMMARY OF INVENTION

However, as for flavor and/or fragrance materials having musky odor, flavor and/or fragrance materials satisfying such requirements are scarce. Hence, beside conventionally known flavor and/or fragrance substances, development of a novel flavor and/or fragrance material satisfying the above-described characteristics has been awaited.

Accordingly, an object of the present invention is to provide a compound which has a musky odor with excellent odor quality, and which satisfies the above-described requirements.

Under such circumstances, the present inventors have conducted intensive study, and consequently have found that ester compounds having a cyclopropane ring have pleasant strong musky odor. This finding has led to the completion of the present invention.

Specifically, the present invention includes the following inventions [1] to [4].

[1]

A compound represented by general formula (1):

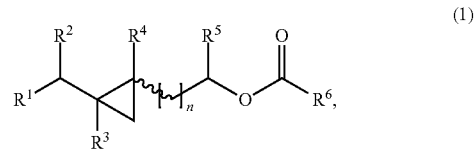

wherein $R^1$ is an alkyl group having 2 to 9 carbon atoms, an alkenyl group having 2 to 9 carbon atoms, a cycloalkyl group having 3 to 10 carbon atoms which may have a substituent, or a phenyl group which may have a substituent, $R^2$ is an alkyl group having 1 to 3 carbon atoms, $R^3$ to $R^5$ are each independently a hydrogen atom or an alkyl group having 1 to 3 carbon atoms, $R^6$ is an alkyl group having 1 to 5 carbon atoms, an alkenyl group having 2 to 5 carbon atoms, a cycloalkyl group having 3 to 10 carbon atoms which may have a substituent, or an alkoxy group having 1 to 5 carbon atoms, n is 0 or 1, and the wavy line means that the compound is a cis isomer, a trans isomer, or a mixture of cis and trans isomers.

[2]

A flavor and/or fragrance composition comprising the compound described in [1].

[3]

A beverage, food, cosmetic, toiletry product, air-care product, daily-necessity or grocery product, oral-care composition, hair-care product, skin-care product, body-care product, laundry detergent, finishing softener for clothes, quasi drug, or drug comprising the flavor and/or fragrance composition described in [2].

[4]

A method for improving an odor of a flavor and/or fragrance, the method comprising adding the compound described in [1] to the flavor and/or fragrance.

The ester compound having a cyclopropane ring, which is the compound according to the present invention, is an extremely useful flavor and/or fragrance material having a pleasant and strong musky odor and being excellent in diffusibility and persistence. Blending the compound of the present invention makes it possible to provide a highly preferred flavor and/or fragrance composition.

DESCRIPTION OF EMBODIMENTS

Hereinafter, the present invention will be described in detail.

A compound of the present invention is an ester compound having a cyclopropane ring and being represented by the following general formula (1):

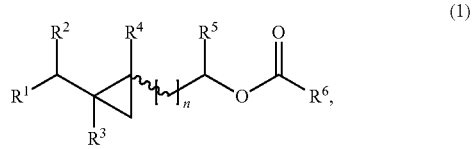

wherein $R^1$ is an alkyl group having 2 to 9 carbon atoms, an alkenyl group having 2 to 9 carbon atoms, a cycloalkyl group having 3 to 10 carbon atoms which may have a substituent, or a phenyl group which may have a substituent, $R^2$ is an alkyl group having 1 to 3 carbon atoms, $R^3$ to $R^5$ are each independently a hydrogen atom or an alkyl group having 1 to 3 carbon atoms, $R^6$ is an alkyl group having 1 to 5 carbon atoms, an alkenyl group having 2 to 5 carbon atoms, a cycloalkyl group having 3 to 10 carbon atoms which may have a substituent, or an alkoxy group having 1 to 5 carbon atoms, n is 0 or 1, and the wavy line means that the compound is a cis isomer, a trans isomer, or a mixture of cis and trans isomers.

$R^1$ in general formula (1) is an alkyl group having 2 to 9 carbon atoms, an alkenyl group having 2 to 9 carbon atoms, a cycloalkyl group having 3 to 10 carbon atoms which may have a substituent, or a phenyl group which may have a substituent.

Examples of the alkyl group having 2 to 9 carbon atoms represented by $R^1$ include an ethyl group, a n-propyl group, an isopropyl group, a n-butyl group, an isobutyl group, a sec-butyl group, a tert-butyl group, a n-pentyl group, an isopentyl group, a neopentyl group, a hexyl group, a heptyl group, an octyl group, a nonyl group, and the like.

Examples of the alkenyl group having 2 to 9 carbon atoms represented by $R^1$ include a vinyl group, a 1-propenyl group, a 2-propenyl group, an isopropenyl group, a 1-butenyl group, a 2-butenyl group, a 3-butenyl group, a 2-methyl-1-butenyl group, a 3-methyl-1-butenyl group, a 2-methyl-2-butenyl group, a 3-methyl-2-butenyl group, a 2-methyl-3-butenyl group, a 3-methyl-3-butenyl group, a pentenyl group, a hexenyl group, a heptenyl group, an octenyl group, a nonenyl group, and the like.

Examples of the cycloalkyl group having 3 to 10 carbon atoms which may have a substituent represented by $R^1$ include a cyclopropyl group, a cyclobutyl group, a cyclopentyl group, a cyclopentenyl group, a cyclopentadienyl group, a cyclohexyl group, a cyclohexenyl group, a cyclohexadienyl group, a cycloheptyl group, a cycloheptenyl group, a cycloheptadienyl group, a cyclooctyl group, a cyclooctenyl group, a cyclooctadienyl group, a cyclononyl group, a cyclononenyl group, a cyclononadienyl group, a cyclodecyl group, a cyclodecenyl group, a cyclodecadienyl group, and the like.

Examples of substituents which may be present on the cycloalkyl groups and the phenyl group include alkyl groups having 1 to 6 carbon atoms such as a methyl group, an ethyl group, a n-propyl group, an isopropyl group, a n-butyl group, an isobutyl group, a sec-butyl group, a tert-butyl group, a pentyl group, and a hexyl group; alkoxy groups having 1 to 4 carbon atoms such as a methoxy group, an ethoxy group, a n-propoxy group, an isopropoxy group, a n-butoxy group, an isobutoxy group, a sec-butoxy group, a tert-butoxy group, and a methylenedioxy group; and the like.

$R^1$ in general formula (1) is preferably an alkenyl group having 2 to 9 carbon atoms, a cycloalkyl group having 3 to 10 carbon atoms which may have a substituent, or a phenyl group which may have a substituent, and is more preferably a 2-methyl-2-butenyl group, a cyclohexyl group, or a phenyl group.

$R^2$ in general formula (1) is an alkyl group having 1 to 3 carbon atoms.

Examples of the alkyl group having 1 to 3 carbon atoms represented by $R^2$ include a methyl group, an ethyl group, a n-propyl group, an isopropyl group, and the like.

$R^2$ in general formula (1) is preferably a methyl group.

$R^3$ to $R^5$ in general formula (1) are each independently a hydrogen atom or an alkyl group having 1 to 3 carbon atoms.

Examples of the alkyl group having 1 to 3 carbon atoms represented by each of $R^3$ to $R^5$ include a methyl group, an ethyl group, a n-propyl group, an isopropyl group, and the like.

$R^3$ in general formula (1) is preferably a hydrogen atom.
$R^4$ in general formula (1) is preferably a methyl group.
$R^5$ in general formula (1) is preferably a hydrogen atom.
$R^6$ in general formula (1) is an alkyl group having 1 to 5 carbon atoms, an alkenyl group having 2 to 5 carbon atoms, a cycloalkyl group having 3 to 10 carbon atoms which may have a substituent, or an alkoxy group having 1 to 5 carbon atoms.

Examples of the alkyl group having 1 to 5 carbon atoms represented by $R^6$ include a methyl group, an ethyl group, a n-propyl group, an isopropyl group, a n-butyl group, an isobutyl group, a sec-butyl group, a tert-butyl group, a n-pentyl group, an isopentyl group, a neopentyl group, and the like.

Examples of the alkenyl group having 2 to 5 carbon atoms represented by $R^6$ include a vinyl group, a 1-propenyl group, a 2-propenyl group, an isopropenyl group, a 1-butenyl group, a 2-butenyl group, a 3-butenyl group, a 2-methyl-1-butenyl group, a 3-methyl-1-butenyl group, a 2-methyl-2-butenyl group, a 3-methyl-2-butenyl group, a 2-methyl-3-butenyl group, a 3-methyl-3-butenyl group, a pentenyl group, and the like.

Examples of the cycloalkyl group having 3 to 10 carbon atoms which may have a substituent represented by $R^6$ include a cyclopropyl group, a cyclobutyl group, a cyclopentyl group, a cyclohexyl group, a cycloheptyl group, a cyclooctyl group, a cyclononyl group, a cyclodecyl group, and the like.

Examples of the alkoxy group having 1 to 5 carbon atoms represented by $R^6$ include a methoxy group, an ethoxy group, a n-propoxy group, an isopropoxy group, a n-butoxy group, an isobutoxy group, a sec-butoxy group, a tert-butoxy group, a n-pentoxy group, an isopentoxy group, a neopentoxy group, and the like.

Examples of substituents which may be present on the cycloalkyl groups include alkyl groups having 1 to 6 carbon atoms such as a methyl group, an ethyl group, a n-propyl group, an isopropyl group, a n-butyl group, an isobutyl group, a sec-butyl group, a tert-butyl group, a pentyl group, and a hexyl group, and the like.

$R^6$ in general formula (1) is preferably an alkyl group having 1 to 5 carbon atoms, an alkenyl group having 2 to 5 carbon atoms, or a cycloalkyl group having 3 to 10 carbon atoms which may have a substituent, and is more preferably an ethyl group, an isopropyl group, a cyclopropyl group, a cyclobutyl group, a vinyl group, or an isopropenyl group.

n is preferably 0.

Preferred specific examples of the ester compound having a cyclopropane ring and being represented by general formula (1) of the present invention include, but are not limited to, the compounds shown in Tables 1 to 9 below.

Abbreviations used in Tables 1 to 9 have the following meaning, and abbreviations used for compounds described below in this Description also have the same meaning. Note that each numeric value represents a position of a substituent on a phenyl group (for example, 4-Me-Ph means a phenyl group having a methyl group at position 4 of the phenyl group, and 3,4-Me-Ph means a phenyl group having a methyl group at each of positions 3 and 4 of the phenyl group).

H hydrogen atom
Ph phenyl group
Me methyl group
Et ethyl group
nPr n-propyl group
iPr isopropyl group
nBu n-butyl group
iBu isobutyl group
secBu sec-butyl group
tBu tert-butyl group
nPen n-pentyl group
iPen isopentyl group
neoPen neopentyl group
Hex hexyl group
Hep heptyl group
Oct octyl group
Non nonyl group
Vinyl vinyl group
Allyl allyl group (2-propenyl group)
1-propenyl 1-propenyl group
isopropenyl isopropenyl group
1-butenyl 1-butenyl group
2-butenyl 2-butenyl group
2-methylallyl 2-methylallyl group
(2-methyl-2-propenyl) (2-methyl-2-propenyl group)
cycloPro cyclopropyl group
cycloBu cyclobutyl group
cycloPen cyclopentyl group
cycloHex cyclohexyl group
2,2,3-TriCyPen 2,2,3-trimethylcyclopentyl group
2,2,3-TriCyPente 2,2,3-trimethylcyclopentenyl group
2,2,6-TriCyHex 2,2,6-trimethylcyclohexyl group
2,2,6-TriCyHexe 2,2,6-trimethylcyclohexenyl group
3-Me-2-Bute 3-methyl-2-butenyl group
MeO methoxy group
EtO ethoxy group
nPrO n-propoxy group
iPrO isopropoxy group

TABLE 1

| Example Compound | $R^1$ | $R^2$ | $R^3$ | $R^4$ | $R^5$ | $R^6$ | n |
|---|---|---|---|---|---|---|---|
| 1 | Ph | Me | H | H | H | Me | 0 |
| 2 | Ph | Me | H | H | H | Et | 0 |
| 3 | Ph | Me | H | H | H | nPr | 0 |
| 4 | Ph | Me | H | H | H | iPr | 0 |
| 5 | Ph | Me | H | H | H | nBu | 0 |
| 6 | Ph | Me | H | H | H | iBu | 0 |
| 7 | Ph | Me | H | H | H | secBu | 0 |
| 8 | Ph | Me | H | H | H | tBu | 0 |
| 9 | Ph | Me | H | H | H | nPen | 0 |
| 10 | Ph | Me | H | H | H | iPen | 0 |
| 11 | Ph | Me | H | H | H | neoPen | 0 |
| 12 | Ph | Me | H | H | H | Hex | 0 |
| 13 | Ph | Me | H | H | H | Hep | 0 |
| 14 | Ph | Me | H | H | H | Oct | 0 |
| 15 | Ph | Me | H | H | H | Non | 0 |
| 16 | Ph | Me | H | H | H | Vinyl | 0 |
| 17 | Ph | Me | H | H | H | Allyl | 0 |
| 18 | Ph | Me | H | H | H | 1-propenyl | 0 |
| 19 | Ph | Me | H | H | H | isopropenyl | 0 |
| 20 | Ph | Me | H | H | H | 1-butenyl | 0 |
| 21 | Ph | Me | H | H | H | 2-butenyl | 0 |
| 22 | Ph | Me | H | H | H | 2-methylallyl | 0 |
| 23 | Ph | Me | H | H | H | cycloPro | 0 |
| 24 | Ph | Me | H | H | H | cycloBu | 0 |
| 25 | Ph | Me | H | H | H | cycloPen | 0 |
| 26 | Ph | Me | H | H | H | cycloHex | 0 |
| 27 | Ph | Me | H | H | H | MeO | 0 |
| 28 | Ph | Me | H | H | H | EtO | 0 |
| 29 | Ph | Me | H | H | H | nPrO | 0 |
| 30 | Ph | Me | H | H | H | iPrO | 0 |

TABLE 2

| Example Compound | $R^1$ | $R^2$ | $R^3$ | $R^4$ | $R^5$ | $R^6$ | n |
|---|---|---|---|---|---|---|---|
| 31 | Ph | Me | H | Me | H | Me | 0 |
| 32 | Ph | Me | H | Me | H | Et | 0 |
| 33 | Ph | Me | H | Me | H | nPr | 0 |
| 34 | Ph | Me | H | Me | H | iPr | 0 |
| 35 | Ph | Me | H | Me | H | nBu | 0 |
| 36 | Ph | Me | H | Me | H | iBu | 0 |
| 37 | Ph | Me | H | Me | H | secBu | 0 |
| 38 | Ph | Me | H | Me | H | tBu | 0 |
| 39 | Ph | Me | H | Me | H | nPen | 0 |
| 40 | Ph | Me | H | Me | H | iPen | 0 |
| 41 | Ph | Me | H | Me | H | neoPen | 0 |
| 42 | Ph | Me | H | Me | H | Hex | 0 |
| 43 | Ph | Me | H | Me | H | Hep | 0 |
| 44 | Ph | Me | H | Me | H | Oct | 0 |
| 45 | Ph | Me | H | Me | H | Non | 0 |
| 46 | Ph | Me | H | Me | H | Vinyl | 0 |
| 47 | Ph | Me | H | Me | H | Allyl | 0 |
| 48 | Ph | Me | H | Me | H | 1-propenyl | 0 |
| 49 | Ph | Me | H | Me | H | isopropenyl | 0 |
| 50 | Ph | Me | H | Me | H | 1-butenyl | 0 |
| 51 | Ph | Me | H | Me | H | 2-butenyl | 0 |
| 52 | Ph | Me | H | Me | H | 2-methylallyl | 0 |
| 53 | Ph | Me | H | Me | H | cycloPro | 0 |
| 54 | Ph | Me | H | Me | H | cycloBu | 0 |
| 55 | Ph | Me | H | Me | H | cycloPen | 0 |
| 56 | Ph | Me | H | Me | H | cycloHex | 0 |
| 57 | Ph | Me | H | Me | H | MeO | 0 |
| 58 | Ph | Me | H | Me | H | EtO | 0 |
| 59 | Ph | Me | H | Me | H | nPrO | 0 |
| 60 | Ph | Me | H | Me | H | iPrO | 0 |

TABLE 3

| Example Compound | R¹ | R² | R³ | R⁴ | R⁵ | R⁶ | n |
|---|---|---|---|---|---|---|---|
| 61 | 4-Me—Ph | Me | H | Me | H | Me | 0 |
| 62 | 4-Me—Ph | Me | H | Me | H | Et | 0 |
| 63 | 4-Me—Ph | Me | H | Me | H | nPr | 0 |
| 64 | 4-Me—Ph | Me | H | Me | H | iPr | 0 |
| 65 | 4-Me—Ph | Me | H | Me | H | Vinyl | 0 |
| 66 | 4-Me—Ph | Me | H | Me | H | Allyl | 0 |
| 67 | 4-Me—Ph | Me | H | Me | H | cycloPro | 0 |
| 68 | 4-Me—Ph | Me | H | Me | H | cycloBu | 0 |
| 69 | 4-Me—Ph | Me | H | H | H | Et | 0 |
| 70 | 4-Me—Ph | Me | H | H | H | Allyl | 0 |
| 71 | 3-Me—Ph | Me | H | Me | H | Me | 0 |
| 72 | 3-Me—Ph | Me | H | Me | H | Et | 0 |
| 73 | 3-Me—Ph | Me | H | Me | H | nPr | 0 |
| 74 | 3-Me—Ph | Me | H | Me | H | iPr | 0 |
| 75 | 3-Me—Ph | Me | H | Me | H | Vinyl | 0 |
| 76 | 3-Me—Ph | Me | H | Me | H | Allyl | 0 |
| 77 | 3-Me—Ph | Me | H | Me | H | cycloPro | 0 |
| 78 | 3-Me—Ph | Me | H | Me | H | cycloBu | 0 |
| 79 | 3-Me—Ph | Me | H | H | H | Et | 0 |
| 80 | 3-Me—Ph | Me | H | H | H | Allyl | 0 |
| 81 | 2-Me—Ph | Me | H | Me | H | Me | 0 |
| 82 | 2-Me—Ph | Me | H | Me | H | Et | 0 |
| 83 | 2-Me—Ph | Me | H | Me | H | nPr | 0 |
| 84 | 2-Me—Ph | Me | H | Me | H | iPr | 0 |
| 85 | 2-Me—Ph | Me | H | Me | H | Vinyl | 0 |
| 86 | 2-Me—Ph | Me | H | Me | H | Allyl | 0 |
| 87 | 2-Me—Ph | Me | H | Me | H | cycloPro | 0 |
| 88 | 2-Me—Ph | Me | H | Me | H | cycloBu | 0 |
| 89 | 2-Me—Ph | Me | H | H | H | Et | 0 |
| 90 | 2-Me—Ph | Me | H | H | H | Allyl | 0 |

TABLE 4

| Example Compound | R¹ | R² | R³ | R⁴ | R⁵ | R⁶ | n |
|---|---|---|---|---|---|---|---|
| 91 | Ph | Me | H | Me | H | Me | 1 |
| 92 | Ph | Me | H | Me | H | Et | 1 |
| 93 | Ph | Me | H | Me | H | nPr | 1 |
| 94 | Ph | Me | H | Me | H | iPr | 1 |
| 95 | Ph | Me | H | Me | H | Vinyl | 1 |
| 96 | Ph | Me | H | Me | H | Allyl | 1 |
| 97 | Ph | Me | H | Me | H | cycloPro | 1 |
| 98 | Ph | Me | H | Me | H | cycloBu | 1 |
| 99 | Ph | Me | H | H | H | Et | 1 |
| 100 | Ph | Me | H | H | H | Allyl | 1 |
| 101 | 4-Me—Ph | Me | H | Me | H | Me | 1 |
| 102 | 4-Me—Ph | Me | H | Me | H | Et | 1 |
| 103 | 4-Me—Ph | Me | H | Me | H | nPr | 1 |
| 104 | 4-Me—Ph | Me | H | Me | H | iPr | 1 |
| 105 | 4-Me—Ph | Me | H | Me | H | Vinyl | 1 |
| 106 | 4-Me—Ph | Me | H | Me | H | Allyl | 1 |
| 107 | 4-Me—Ph | Me | H | Me | H | cycloPro | 1 |
| 108 | 4-Me—Ph | Me | H | Me | H | cycloBu | 1 |
| 109 | 4-Me—Ph | Me | H | H | H | Et | 1 |
| 110 | 4-Me—Ph | Me | H | H | H | Allyl | 1 |
| 111 | 3-Me—Ph | Me | H | Me | H | Me | 1 |
| 112 | 3-Me—Ph | Me | H | Me | H | Et | 1 |
| 113 | 3-Me—Ph | Me | H | Me | H | nPr | 1 |
| 114 | 3-Me—Ph | Me | H | Me | H | iPr | 1 |
| 115 | 3-Me—Ph | Me | H | Me | H | Vinyl | 1 |
| 116 | 3-Me—Ph | Me | H | Me | H | Allyl | 1 |
| 117 | 3-Me—Ph | Me | H | Me | H | cycloPro | 1 |
| 118 | 3-Me—Ph | Me | H | Me | H | cycloBu | 1 |
| 119 | 3-Me—Ph | Me | H | H | H | Et | 1 |
| 120 | 3-Me—Ph | Me | H | H | H | Allyl | 1 |

TABLE 5

| Example Compound | R¹ | R² | R³ | R⁴ | R⁵ | R⁶ | n |
|---|---|---|---|---|---|---|---|
| 121 | 2-Me—Ph | Me | H | Me | H | Me | 1 |
| 122 | 2-Me—Ph | Me | H | Me | H | Et | 1 |
| 123 | 2-Me—Ph | Me | H | Me | H | nPr | 1 |
| 124 | 2-Me—Ph | Me | H | Me | H | iPr | 1 |
| 125 | 2-Me—Ph | Me | H | Me | H | Vinyl | 1 |
| 126 | 2-Me—Ph | Me | H | Me | H | Allyl | 1 |
| 127 | 2-Me—Ph | Me | H | Me | H | cycloPro | 1 |
| 128 | 2-Me—Ph | Me | H | Me | H | cycloBu | 1 |
| 129 | 2-Me—Ph | Me | H | H | H | Et | 1 |
| 130 | 2-Me—Ph | Me | H | H | H | Allyl | 1 |
| 131 | cycloPen | Me | H | Me | H | Me | 0 |
| 132 | cycloPan | Me | H | Me | H | Et | 0 |
| 133 | cycloPen | Me | H | Me | H | nPr | 0 |
| 134 | cycloPen | Me | H | Me | H | iPr | 0 |
| 135 | cycloPan | Me | H | Me | H | Vinyl | 0 |
| 136 | cycloPen | Me | H | Me | H | Allyl | 0 |
| 137 | cycloPen | Me | H | Me | H | cycloPro | 0 |
| 138 | cycloPan | Me | H | Me | H | cycloBu | 0 |
| 139 | cycloPen | Me | H | H | H | Et | 0 |
| 140 | cycloPen | Me | H | H | H | Allyl | 0 |
| 141 | cycloPan | Me | H | Me | H | Me | 1 |
| 142 | cycloPen | Me | H | Me | H | Et | 1 |
| 143 | cycloPen | Me | H | Me | H | nPr | 1 |
| 144 | cycloPan | Me | H | Me | H | iPr | 1 |
| 145 | cycloPen | Me | H | Me | H | Vinyl | 1 |
| 146 | cycloPen | Me | H | Me | H | Allyl | 1 |
| 147 | cycloPan | Me | H | Me | H | cycloPro | 1 |
| 148 | cycloPen | Me | H | Me | H | cycloBu | 1 |
| 149 | cycloPan | Me | H | H | H | Et | 1 |
| 150 | cycloPen | Me | H | H | H | Allyl | 1 |

TABLE 6

| Example Compound | R¹ | R² | R³ | R⁴ | R⁵ | R⁶ | n |
|---|---|---|---|---|---|---|---|
| 151 | cycloHex | Me | H | Me | H | Me | 0 |
| 152 | cycloHex | Me | H | Me | H | Et | 0 |
| 153 | cycloHex | Me | H | Me | H | nPr | 0 |
| 154 | cycloHex | Me | H | Me | H | iPr | 0 |
| 155 | cycloHex | Me | H | Me | H | Vinyl | 0 |
| 156 | cycloHex | Me | H | Me | H | Allyl | 0 |
| 157 | cycloHex | Me | H | Me | H | cycloPro | 0 |
| 158 | cycloHex | Me | H | Me | H | cycloBu | 0 |
| 159 | cycloHex | Me | H | H | H | Et | 0 |
| 160 | cycloHex | Me | H | H | H | Allyl | 0 |
| 161 | cycloHex | Me | H | Me | H | Me | 1 |
| 162 | cycloHex | Me | H | Me | H | Et | 1 |
| 163 | cycloHex | Me | H | Me | H | nPr | 1 |
| 164 | cycloHex | Me | H | Me | H | iPr | 1 |
| 165 | cycloHex | Me | H | Me | H | Vinyl | 1 |
| 166 | cycloHex | Me | H | Me | H | Allyl | 1 |
| 167 | cycloHex | Me | H | Me | H | cycloPro | 1 |
| 178 | cycloHex | Me | H | Me | H | cycloBu | 1 |
| 169 | cycloHex | Me | H | H | H | Et | 1 |
| 170 | cycloHex | Me | H | H | H | Allyl | 1 |
| 171 | 2,3,3-TriCyPen | Me | H | Me | H | Me | 0 |
| 172 | 2,3,3-TriCyPen | Me | H | Me | H | Et | 0 |
| 173 | 2,3,3-TriCyPen | Me | H | Me | H | nPr | 0 |
| 174 | 2,3,3-TriCyPen | Me | H | Me | H | iPr | 0 |
| 175 | 2,3,3-TriCyPen | Me | H | Me | H | Vinyl | 0 |
| 176 | 2,3,3-TriCyPen | Me | H | Me | H | Allyl | 0 |
| 177 | 2,3,3-TriCyPen | Me | H | Me | H | cycloPro | 0 |
| 178 | 2,3,3-TriCyPen | Me | H | Me | H | cycloBu | 0 |
| 179 | 2,3,3-TriCyPen | Me | H | H | H | Et | 0 |
| 180 | 2,3,3-TriCyPen | Me | H | H | H | Allyl | 0 |

TABLE 7

| Example Compound | R¹ | R² | R³ | R⁴ | R⁵ | R⁶ | n |
|---|---|---|---|---|---|---|---|
| 181 | 2,3,3-TriCyPen | Me | H | Me | H | Me | 1 |
| 182 | 2,3,3-TriCyPen | Me | H | Me | H | Et | 1 |
| 183 | 2,3,3-TriCyPen | Me | H | Me | H | nPr | 1 |
| 184 | 2,3,3-TriCyPen | Me | H | Me | H | iPr | 1 |
| 185 | 2,3,3-TriCyPen | Me | H | Me | H | Vinyl | 1 |
| 186 | 2,3,3-TriCyPen | Me | H | Me | H | Allyl | 1 |
| 187 | 2,3,3-TriCyPen | Me | H | Me | H | cycloPro | 1 |
| 188 | 2,3,3-TriCyPen | Me | H | Me | H | cycloBu | 1 |
| 189 | 2,3,3-TriCyPen | Me | H | H | H | Et | 1 |
| 190 | 2,3,3-TriCyPen | Me | H | H | H | Allyl | 1 |
| 191 | 2,3,3-TriCyPente | Me | H | Me | H | Me | 0 |
| 192 | 2,3,3-TriCyPente | Me | H | Me | H | Et | 0 |
| 193 | 2,3,3-TriCyPente | Me | H | Me | H | nPr | 0 |
| 194 | 2,3,3-TriCyPente | Me | H | Me | H | iPr | 0 |
| 195 | 2,3,3-TriCyPente | Me | H | Me | H | Vinyl | 0 |
| 196 | 2,3,3-TriCyPente | Me | H | Me | H | Allyl | 0 |
| 197 | 2,3,3-TriCyPente | Me | H | Me | H | cycloPro | 0 |
| 198 | 2,3,3-TriCyPente | Me | H | Me | H | cycloBu | 0 |
| 199 | 2,3,3-TriCyPenet | Me | H | H | H | Et | 0 |
| 200 | 2,3,3-TriCyPente | Me | H | H | H | Allyl | 0 |
| 201 | 2,3,3-TriCyPente | Me | H | Me | H | Me | 1 |
| 202 | 2,3,3-TriCyPente | Me | H | Me | H | Et | 1 |
| 203 | 2,3,3-TriCyPente | Me | H | Me | H | nPr | 1 |
| 204 | 2,3,3-TriCyPente | Me | H | Me | H | iPr | 1 |
| 205 | 2,3,3-TriCyPente | Me | H | Me | H | Vinyl | 1 |
| 206 | 2,3,3-TriCyPente | Me | H | Me | H | Allyl | 1 |
| 207 | 2,3,3-TriCyPente | Me | H | Me | H | cycloPro | 1 |
| 208 | 2,3,3-TriCyPente | Me | H | Me | H | cycloBu | 1 |
| 209 | 2,3,3-TriCyPenet | Me | H | H | H | Et | 1 |
| 210 | 2,3,3-TriCyPente | Me | H | H | H | Allyl | 1 |

TABLE 8

| Example Compound | R¹ | R² | R³ | R⁴ | R⁵ | R⁶ | n |
|---|---|---|---|---|---|---|---|
| 211 | 2,2,6-TriCyHex | Me | H | Me | H | Me | 0 |
| 212 | 2,2,6-TriCyHex | Me | H | Me | H | Et | 0 |
| 213 | 2,2,6-TriCyHex | Me | H | Me | H | nPr | 0 |
| 214 | 2,2,6-TriCyHex | Me | H | Me | H | iPr | 0 |
| 215 | 2,2,6-TriCyHex | Me | H | Me | H | Vinyl | 0 |
| 216 | 2,2,6-TriCyHex | Me | H | Me | H | Allyl | 0 |
| 217 | 2,2,6-TriCyHex | Me | H | Me | H | cycloPro | 0 |
| 218 | 2,2,6-TriCyHex | Me | H | Me | H | cycloBu | 0 |
| 219 | 2,2,3-TriCyHex | Me | H | H | H | Et | 0 |
| 220 | 2,2,6-TriCyHex | Me | H | H | H | Allyl | 0 |
| 221 | 2,2,6-TriCyHex | Me | H | Me | H | Me | 1 |
| 222 | 2,2,6-TriCyHex | Me | H | Me | H | Et | 1 |
| 223 | 2,2,6-TriCyHex | Me | H | Me | H | nPr | 1 |
| 224 | 2,2,6-TriCyHex | Me | H | Me | H | iPr | 1 |
| 225 | 2,2,6-TriCyHex | Me | H | Me | H | Vinyl | 1 |
| 226 | 2,2,6-TriCyHex | Me | H | Me | H | Allyl | 1 |
| 227 | 2,2,6-TriCyHex | Me | H | Me | H | cycloPro | 1 |
| 228 | 2,2,6-TriCyHex | Me | H | Me | H | cycloBu | 1 |
| 229 | 2,2,6-TriCyHex | Me | H | H | H | Et | 1 |
| 230 | 2,2,6-TriCyHex | Me | H | H | H | Allyl | 1 |
| 231 | 2,2,6-TriCyHexe | Me | H | Me | H | Me | 0 |
| 232 | 2,2,6-TriCyHexe | Me | H | Me | H | Et | 0 |
| 233 | 2,2,6-TriCyHexe | Me | H | Me | H | nPr | 0 |
| 234 | 2,2,6-TriCyHexe | Me | H | Me | H | iPr | 0 |
| 235 | 2,2,6-TriCyHexe | Me | H | Me | H | Vinyl | 0 |
| 236 | 2,2,6-TriCyHexe | Me | H | Me | H | Allyl | 0 |
| 237 | 2,2,6-TriCyHexe | Me | H | Me | H | cycloPro | 0 |
| 238 | 2,2,6-TriCyHexe | Me | H | Me | H | cycloBu | 0 |
| 239 | 2,2,6-TriCyHexe | Me | H | H | H | Et | 0 |
| 240 | 2,2,6-TriCyHexe | Me | H | H | H | Allyl | 0 |

TABLE 9

| Example Compound | R¹ | R² | R³ | R⁴ | R⁵ | R⁶ | n |
|---|---|---|---|---|---|---|---|
| 241 | 2,2,6-TriCyHexe | Me | H | Me | H | Me | 1 |
| 242 | 2,2,6-TriCyHexe | Me | H | Me | H | Et | 1 |
| 243 | 2,2,6-TriCyHexe | Me | H | Me | H | nPr | 1 |
| 244 | 2,2,6-TriCyHexe | Me | H | Me | H | iPr | 1 |
| 245 | 2,2,6-TriCyHexe | Me | H | Me | H | Vinyl | 1 |
| 246 | 2,2,6-TriCyHexe | Me | H | Me | H | Allyl | 1 |
| 247 | 2,2,6-TriCyHexe | Me | H | Me | H | cycloPro | 1 |
| 248 | 2,2,6-TriCyHexe | Me | H | Me | H | cycloBu | 1 |
| 249 | 2,2,6-TriCyHexe | Me | H | H | H | Et | 1 |
| 250 | 2,2,6-TriCyHexe | Me | H | H | H | Allyl | 1 |
| 251 | 2-Me-2-Bute | Me | H | Me | H | Me | 0 |
| 252 | 2-Me-2-Bute | Me | H | Me | H | Et | 0 |
| 253 | 2-Me-2-Bute | Me | H | Me | H | nPr | 0 |
| 254 | 2-Me-2-Bute | Me | H | Me | H | iPr | 0 |
| 255 | 2-Me-2-Bute | Me | H | Me | H | Vinyl | 0 |
| 256 | 2-Me-2-Bute | Me | H | Me | H | Allyl | 0 |
| 257 | 2-Me-2-Bute | Me | H | Me | H | cycloPro | 0 |
| 258 | 2-Me-2-Bute | Me | H | Me | H | cycloBu | 0 |
| 259 | 2-Me-2-Bute | Me | H | H | H | Et | 0 |
| 260 | 2-Me-2-Bute | Me | H | H | H | Allyl | 0 |
| 261 | 2-Me-2-Bute | Me | H | Me | H | Me | 1 |
| 262 | 2-Me-2-Bute | Me | H | Me | H | Et | 1 |
| 263 | 2-Me-2-Bute | Me | H | Me | H | nPr | 1 |
| 264 | 2-Me-2-Bute | Me | H | Me | H | iPr | 1 |
| 265 | 2-Me-2-Bute | Me | H | Me | H | Vinyl | 1 |
| 266 | 2-Me-2-Bute | Me | H | Me | H | Allyl | 1 |
| 267 | 2-Me-2-Bute | Me | H | Me | H | cycloPro | 1 |
| 268 | 2-Me-2-Bute | Me | H | Me | H | cycloBu | 1 |
| 269 | 2-Me-2-Bute | Me | H | H | H | Et | 1 |
| 270 | 2-Me-2-Bute | Me | H | H | H | Allyl | 1 |

More preferred ester compounds having a cyclopropane ring and being represented by general formula (1) include [1-methyl-2-(1-phenylethyl)cyclopropyl)]methyl propionate (Example Compound 32),
[l-methyl-2-(l-phenylethyl)cyclopropyl)]methyl isobutanoate (Example Compound 34),
[1-methyl-2-(1-phenylethyl)cyclopropyl)]methyl acrylate (Example Compound 46),
[1-methyl-2-(1-phenylethyl)cyclopropyl)]methyl methacrylate (Example Compound 47),
[1-methyl-2-(1-phenylethyl)cyclopropyl)]methyl cyclopropanecarboxylate (Example Compound 53),
[1-methyl-2-(1-phenylethyl)cyclopropyl)]methyl cyclobutanecarboxylate (Example Compound 54),
[2-(1-cyclohexylethyl)-1-methylcyclopropyl)]methyl propionate (Example Compound 152),
[2-(1-cyclohexylethyl)-1-methylcyclopropyl)]methyl isobutyrate (Example Compound 154),
[2-(1-cyclohexylethyl)-1-methylcyclopropyl)]methyl cyclopropanecarboxylate (Example Compound 157),
[2-(1-cyclohexylethyl)-1-methylcyclopropyl)]methyl cyclobutanecarboxylate (Example Compound 158),
[1-methyl-2-(5-methylhex-4-en-2-yl)cyclopropyl)]methyl propionate (Example Compound 252),
[1-methyl-2-(5-methylhex-4-en-2-yl)cyclopropyl)]methyl isobutyrate (Example Compound 254),
[1-methyl-2-(5-methylhex-4-en-2-yl)cyclopropyl)]methyl cyclopropanecarboxylate (Example Compound 257),
[1-methyl-2-(5-methylhex-4-en-2-yl)cyclopropyl)]methyl cyclobutanecarboxylate (Example Compound 258), and the like.

The ester compound having a cyclopropane ring of the present invention is synthesized by, for example, the methods shown in schemes 1 to 4 shown below. However, the methods for synthesizing the ester compound are not limited to the methods of schemes 1 to 4 shown below.

A compound of formula (1), in which R⁵ is a hydrogen atom, and n=0, is synthesized by, for example, the method shown in scheme 1:

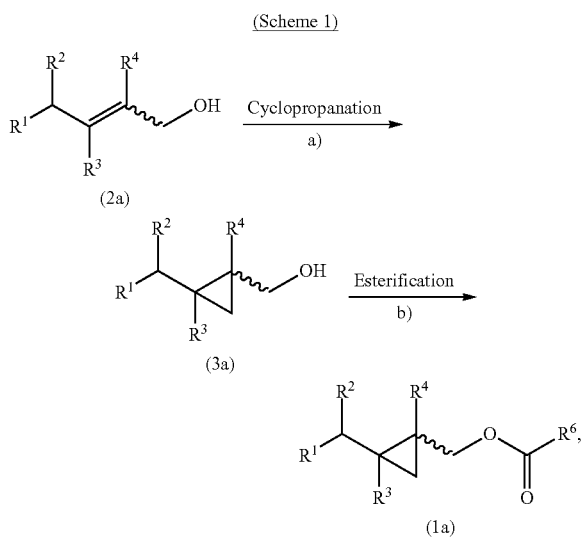

wherein R¹ is an alkyl group having 2 to 9 carbon atoms, an alkenyl group having 2 to 9 carbon atoms, a cycloalkyl group having 3 to 10 carbon atoms which may have a substituent, or a phenyl group which may have a substituent, R² is an alkyl group having 1 to 3 carbon atoms, R³ and R⁴ are each independently a hydrogen atom or an alkyl group having 1 to 3 carbon atoms, R⁶ is an alkyl group having 1 to 5 carbon atoms, an alkenyl group having 2 to 5 carbon atoms, a cycloalkyl group having 3 to 10 carbon atoms which may have a substituent, or an alkoxy group having 1 to 5 carbon atoms, and the wavy line means that the compound is a cis isomer, a trans isomer, or a mixture of cis and trans isomers.
a) Et₂Zn, ICH₂Cl
b) Base, XCOR⁶, where X=a halogen atom, for example, a chlorine atom, a bromine atom, or an iodine atom In scheme 1, allyl alcohol (2a) is reacted with a carbenoid prepared from diethylzinc and chloroiodomethane to synthesize alcohol compound (3a) having a cyclopropane ring. The alcohol compound having a cyclopropane ring is obtained as an isomer mixture of diastereomers having the relative configurations shown below:

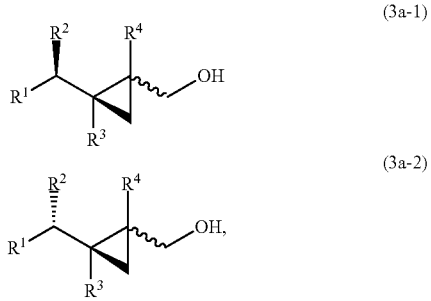

wherein R¹, R², R³, R⁴, and the wavy line have the same meaning as described above.

Esterification of alcohol compound (3a) having a cyclopropane ring and being obtained here can give ester compound (1a) having a cyclopropane ring.

A compound of formula (1), in which R⁵ is an alkyl group having 1 to 3 carbon atoms, and n=0, is synthesized by, for example, the method shown in scheme 2:

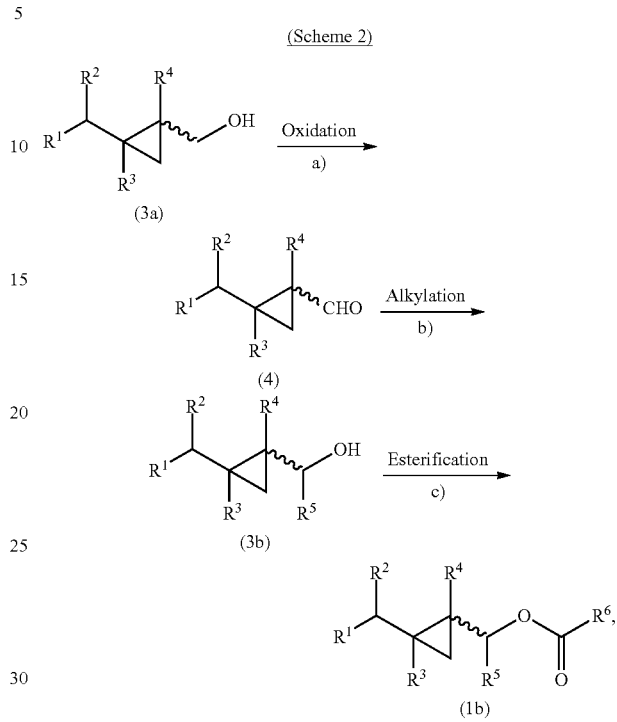

wherein R¹, R², R³, R⁴, R⁵, R⁶, and the wavy line have the same meaning as described above.
a) TEMPO oxidation
b) R⁵MgX, where X=a halogen atom, for example, a chlorine atom, a bromine atom, or an iodine atom
c) Base, XCOR⁶, where X=a halogen atom, for example, a chlorine atom, a bromine atom, or an iodine atom In scheme 2, alcohol compound (3a) having a cyclopropane ring and being obtained by the method described in scheme 1 is oxidized to obtain aldehyde compound (4) having a cyclopropane ring. A subsequent Grignard reaction can give alkylated alcohol compound (3b). Here, as a method for the oxidation reaction, a method for oxidizing a primary alcohol to an aldehyde can be used, in general. For example, it is possible to use a reaction such as TEMPO oxidation, the Uemura oxidation, the Albright-Goldman oxidation, the Mukaiyama oxidation, the Ley-Griffith oxidation, or the Swern oxidation.

Esterification of alkylated alcohol compound (3b) obtained here can give ester compound (1b) having a cyclopropane ring.

A compound of formula (1), in which R⁵ is a hydrogen atom, and n=1, is synthesized by, for example, the method shown in scheme 3:

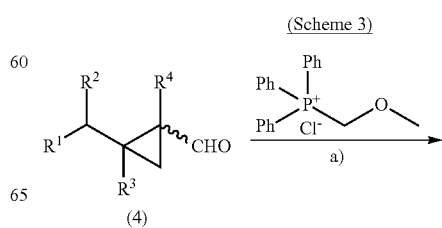

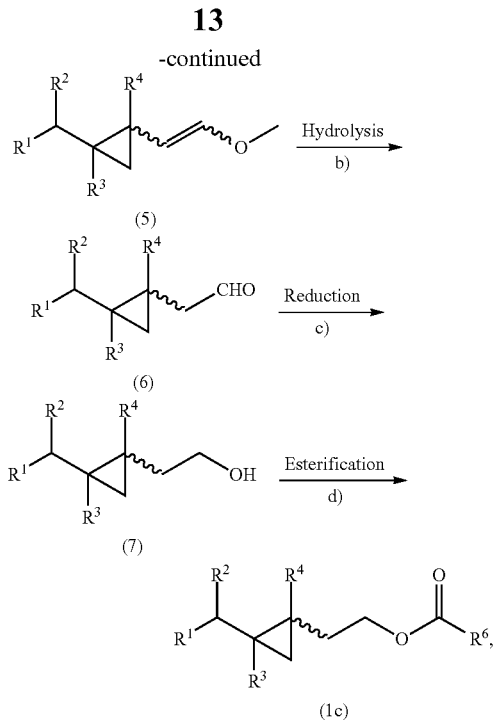

wherein $R^1$, $R^2$, $R^3$, $R^4$, $R^6$, and the wavy line have the same meaning as described above.
a) $(Ph)_3P^+CH_2OCH_3 \cdot Cl^-$, Base
b) $H^+$, $H_2O$
c) $NaBH_4$
d) Base, $XCOR^6$, where X=a halogen atom, for example, a chlorine atom, a bromine atom, or an iodine atom In scheme 3, enol ether (5) can be obtained by a Witting reaction of aldehyde compound (4) having a cyclopropane ring and being obtained by the method described in scheme 2. By hydrolysis of the enol ether in the presence of an acid catalyst, corresponding compound (6) having a cyclopropane ring can be easily synthesized. Acids used here include acetic acid, citric acid, hydrochloric acid, sulfuric acid, and the like. Corresponding alcohol compound (7) is formed by reduction of the aldehyde moiety of compound (6) having a cyclopropane ring and being obtained here. Subsequent esterification can give ester compound (1c) having a cyclopropane ring.

A compound of formula (1), in which $R^5$ is an alkyl group having 1 to 3 carbon atoms, and n=1, is synthesized by, for example, the method shown in scheme 4:

(Scheme 4)

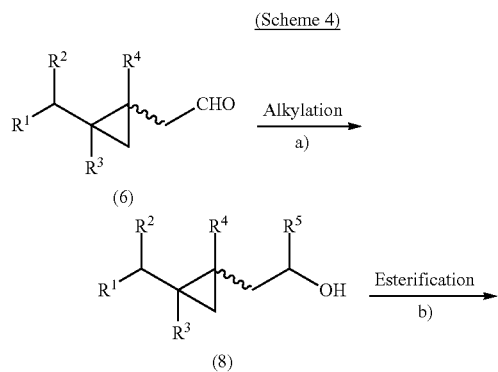

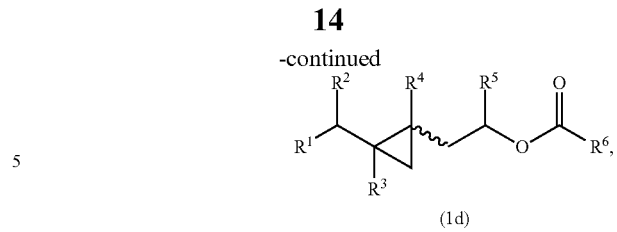

wherein $R^1$, $R^2$, $R^3$, $R^4$, $R^5$, $R^6$, and the wavy line have the same meaning as described above.
a) $R^5MgX$, where X=a halogen atom, for example, a chlorine atom, a bromine atom, or an iodine atom
b) Base, $XCOR^6$, where X=a halogen atom, for example, a chlorine atom, a bromine atom, or an iodine atom In scheme 4, alkylated alcohol compound (8) can be obtained by a Grignard reaction of aldehyde compound (6) having a cyclopropane ring and being obtained by the method described in scheme 3. Subsequent esterification of alkylated alcohol compound (8) can give ester compound (id) having a cyclopropane ring.

If necessary, the thus obtained compound of the present invention can be isolated and purified. Examples of methods for the isolation and purification include column chromatography, vacuum distillation, crystallization, and the like. The isolation and purification can be achieved by one of these methods alone or by a combination thereof.

The ester compound having a cyclopropane ring and being represented by general formula (1) of the present invention has a musky odor.

Note that the ester compound having a cyclopropane ring and being represented by general formula (1) of the present invention can be obtained as an isomer mixture of diastereomers having the relative configurations shown below.

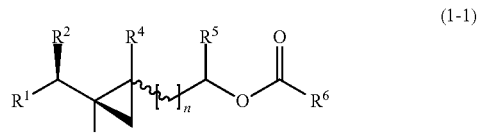

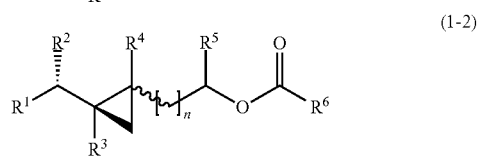

wherein $R^1$, $R^2$, $R^3$, $R^4$, $R^5$, $R^6$, n, and the wavy line have the same meaning as described above.

Of these diastereomers, the syn isomer represented by general formula (1-1) has a strong musky odor, whereas the strength of the odor of the anti isomer represented by general formula (1-2) is extremely low.

The ester compound having a cyclopropane ring and being represented by general formula (1) can be added to a flavor and/or fragrance composition comprising an ordinary used flavor and/or fragrance component. The other flavor and/or fragrance components include various synthetic flavors and/or fragrances, natural essential oils, synthetic essential oils, citrus oils, animal flavors and/or fragrances, and the like. For example, a wide variety of flavor and/or fragrance components as described in documents shown below can be used. The amount of the ester compound having a cyclopropane ring and being represented by general formula (1) blended in the flavor and/or fragrance composition is not particularly limited, and is preferably 0.001 to 60% by weight, and particularly preferably 0.01 to 40% by weight relative to the flavor and/or fragrance composition.

Representative flavor and/or fragrance components include α-pinene, limonene, cis-3-hexenol, phenylethyl alcohol, styralyl acetate, eugenol, rose oxide, linalool, benzaldehyde, methyl dihydrojasmonate, muscone, Musk T (Takasago International Corporation), Thesaron (Takasago International Corporation), and the like. Other examples include a wide variety of flavor and/or fragrance components as described in Arctander S. "Perfume and Flavor Chemicals" published By the author, Montclair, N.J. (U.S.A.), 1969 or "Collection of Well-known Prior Arts (Flavors and Fragrances), Part I" (published by Japan Patent office on Jan. 29, 1999).

When the ester compound having a cyclopropane ring and being represented by general formula (1) is added to, for example, a natural essential oil such as bergamot oil, galbanum oil, lemon oil, geranium oil, lavender oil, or mandarin oil, it is possible to prepare a novel flavor and/or fragrance composition which is mild, rich, fresh, and highly preferred, and is persistent with enhanced diffusibility and enhanced fixation ability, in addition to having the odor and flavor intrinsic to the natural essential oil.

In the present invention, one of or two or more of ordinarily used additional flavor and/or fragrance fixatives may be blended in the flavor and/or fragrance composition comprising the ester compound having a cyclopropane ring and being represented by general formula (1). Examples of the flavor and/or fragrance fixatives include ethylene glycol, propylene glycol, dipropylene glycol, glycerin, hexyl glycol, benzyl benzoate, triethyl citrate, diethyl phthalate, Hercolyn (methyl abietate), medium-chain fatty acid triglycerides, and the like.

Examples of products which can be scented with the flavor and/or fragrance composition comprising the ester compound having a cyclopropane ring and being represented by general formula (1) of the present invention include, but are not particularly limited to, beverages, foods, cosmetics, toiletry products, air-care products, daily-necessity or grocery products, oral-care compositions, hair-care products, skin-care products, body-care products, laundry detergents, finishing softeners for clothes, quasi drugs, drugs, and the like.

Specific examples of the beverages and foods, include, but are not at all limited to, beverages such as fruit juice beverages, alcoholic fruit beverages, dairy beverages, carbonated beverages, refreshing beverages, and drink preparations; cold desserts such as ice creams, sorbets, and ice pops; desserts such as jellies and puddings; Western confectionery products such as cakes, cookies, chocolates, and chewing gums; Japanese confectionery products such as steamed bean-jam buns, Yokan (soft adzuki-bean jellies), and Uiro (traditional Japanese steamed cakes made of rice flour and sugar); jams; candies; breads; tea beverages and favorite beverages such as green tea, oolong tea, black tea, persimmon leaf tea, chamomile tea, Kumazasa (*Sasa veitchii*) tea, mulberry leaf tea, *Houttuynia cordata* tea, pu-erh tea, mate tea, rooibos tea, gymnema tea, guava tea, coffee, and cocoa; soups such as Japanese style soups, Western style soups, and Chinese soups; flavor seasonings; various instant beverages and foods; various snack foods; oral cavity compositions such as dentifrices, oral cavity-washing agents, mouthwashes, troches, and chewing gums; and the like.

Meanwhile, examples of the cosmetics, toiletry products, air-care products, daily-necessity or grocery products, oral cavity compositions, hair-care products, skin-care products, body-care products, laundry detergents, finishing softeners for clothes, and quasi drugs include fragrance products, basic skin-care cosmetics, make-up cosmetics, hair cosmetics, sunscreen cosmetics, medicated cosmetics, hair-care products, soaps, body cleaning agents, bath agents, detergents, finishing softeners, cleaning agents, kitchen detergents, bleaching agents, aerosols, air fresheners, repellents, other grocery products, and the like.

More specifically, the fragrance products include perfumes, Eau de Parfum, Eau de Toilette, Eau de Cologne, and the like;

the basic skin-care cosmetics include face wash creams, vanishing creams, cleansing creams, cold creams, massage creams, emulsions, lotions, cosmetic serums, packs, make-up removers, and the like;

the make-up cosmetics include foundations, loose face powders, pressed face powders, talcum powders, lipsticks, lip balms, cheek rouges, eyeliners, mascaras, eye shadows, eyebrow-colors, eye packs, nail enamels, enamel removers, and the like; and the hair cosmetics include pomades, brilliantine, set lotions, hair sticks, hair solids, hair oils, hair treatments, hair creams, hair tonics, hair liquids, hair sprays, bandolines, hair-growing agents, hair dyes, and the like.

The sunscreen cosmetics include suntan products, sunscreen products, and the like;

the medicated cosmetics include antiperspirants, after-shaving lotions and gels, permanent wave agents, medicated soaps, medicated shampoos, medicated skin cosmetics, and the like;

the hair-care products include shampoos, rinses, two-in-one shampoos, conditioners, treatments, hair packs, and the like;

the soaps include toilet soaps, bath soaps, fragrance soaps, transparent soaps, synthetic soaps, and the like;

the body cleaning agents include body soaps, body shampoos, hand soaps, and the like;

the bath agents include bath additives (bath salts, bath tablets, bath liquids, and the like), foam baths (bubble baths and the like), bath oils (bath perfumes, bath capsules, and the like), milk baths, bath jellies, bath cubes, and the like; and the detergents include heavy duty detergents for clothes, light duty detergents for clothes, liquid detergents, laundry soaps, compact detergents, powder soaps, and the like.

The finishing softeners include softeners, furniture-cares, and the like;

the cleaning agents include cleansers, house cleaning agents, toilet cleaning agents, bathroom cleaning agents, glass cleaners, mold removers, drainpipe cleaning agents, and the like;

the kitchen detergents include kitchen soaps, kitchen synthetic soaps, dish detergents, and the like;

the bleaching agents include oxidation-type bleaching agents (chlorine-based bleaching agents, oxygen-based bleaching agents, and the like), reduction-type bleaching agents (sulfur-based bleaching agents and the like), optical bleaching agents, and the like;

the aerosols include spray-type aerosols, powder sprays, and the like;

the air fresheners include solid-type air fresheners, gel-type air fresheners, liquid-type air fresheners, and the like; and the groceries include tissue paper, toilet paper, and the like.

Specific examples of the drugs include, but are not at all limited to, skin external agents such as cataplasms and ointments, internal agents, and the like.

The form of each of the products which can be scented with the flavor and/or fragrance composition comprising the ester compound having a cyclopropane ring and being represented by general formula (1) may be the form of a mixture, as it is. Examples of other forms include a liquid form in which the components are dissolved in an alcohol, a polyol such as propylene glycol, glycerin, or dipropylene glycol, or an ester such as triethyl citrate, benzyl benzoate, or diethyl phthalate; an emulsion form in which the components are emulsified with an emulsifier such as a natural gum substance, including gum arabic, gum tragacanth, and the like, a glycerin fatty acid ester, a sucrose fatty acid ester, or the like; a powder form in which the components are coated with an excipient such as a natural gum substance, including gum arabic and the like, gelatin, dextrin, or the like; a solubilized or dispersed form in which the components are solubilized or dispersed by using a surfactant, for example, a nonionic surfactant, an anionic surfactant, a cationic surfactant, an amphoteric surfactant, or the like; a microcapsule obtained by treatment with an encapsulating agent; and the like. Any of these forms is selected and used according to the purpose.

Moreover, in some cases, the fragrance composition may be used in a stabilized and sustained-release form by forming an inclusion compound in an agent for inclusion such as cyclodextrin. These are suitable for the forms of finished products such as, for example, liquid forms, solid forms, powder forms, gel forms, mist forms, and aerosol forms, and are selectively used as appropriate. These are suitable for the forms of finished products such as, for example, liquid forms, solid forms, powder forms, gel forms, mist forms, and aerosol forms, and are selectively used as appropriate.

EXAMPLES

Hereinafter, the present invention is described specifically based on Examples. However, the present invention is not limited to these Examples at all, and may be modified or altered in various manners within the scope of the present invention. Note that, unless otherwise noted, the unit "%" means "% by mass," and each of the compositional ratios in the recipes described below shows a mass ratio.

Note that, in Examples, physical properties were measured by using the following instruments.
NMR: DRX500 (manufactured by Bruker)
GC/MS: HP5973 (manufactured by HEWLETT PACKARD) Column: capillary column of GL Sciences Inc.
 Inertcap-1 (30 m in length×0.25 mm in inner diameter with a film thickness of 0.25 μm)
GC purity: HP6890 (manufactured by HEWLETT PACKARD)
Column: Capillary column of GL Sciences Inc.
 Inertcap-1 (30 min length×0.25 mm in inner diameter with a film thickness of 0.25 μm) Injection temperature: 250° C., detector temperature: 250° C.
The temperature was raised from 100° C. to 200° C. at 10° C./min.

Synthesis Example 1

Synthesis of [1-Methyl-2-(1-phenylethyl)cyclopropyl]methanol

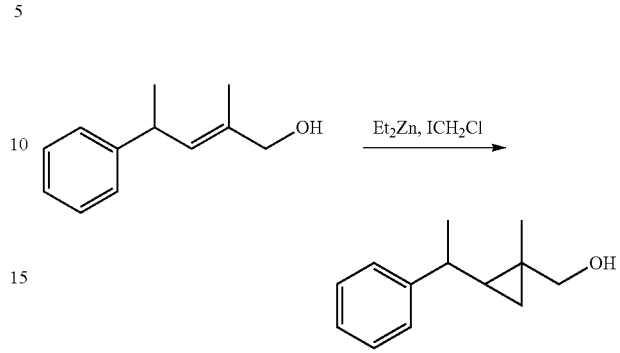

In a nitrogen atmosphere, a diethylzinc solution in toluene (concentration: 15% by weight, 37.9 g, 0.046 mol) was placed in a 200 ml flask equipped with a stirrer, a dropping funnel, and a thermometer, and cooled to −20° C. Chloroiodomethane (16.22 g, 0.092 mol) was placed in a dropping funnel, and added dropwise with the temperature being kept at −15 to −20° C. After completion of the dropwise addition, the mixture was stirred at −10 to −15° C. for 30 minutes. Then, the mixture was cooled to −25° C., and (E)-2-methyl-4-phenylpent-2-en-1-ol (4.11 g, 0.0233 mol) was added dropwise over 60 minutes in the range from −20 to −25° C. After completion of the dropwise addition, stirring was continued at −15 to −25° C. for 60 minutes. Next, a 20% aqueous sulfuric acid solution (17.0 ml) was added, followed by stirring for 10 minutes. Then, the aqueous layer was separated. The organic layer was washed with water (20 ml) twice, and the solvent was recovered under reduced pressure to obtain a concentrated residue. This residue was purified by silica gel column chromatography (hexane:ethyl acetate=8:2) to obtain [(1R*,2S*)-1-methyl-2-((R*)-1-phenylethyl)cyclopropyl]methanol (1.85 g, 0.00974 mol, yield: 42%) as a main isomer, and [(1R*,2S*)-1-methyl-2-((S*)-1-phenylethyl)cyclopropyl]methanol (0.55 g, 0.0029 mol, yield: 12%) as a minor isomer. The relative configurations of the main isomer and the minor isomer were determined by NOESY measurement.
Main Isomer
 GC/MS (m/e):
 190 (M$^+$, <1), 172(1), 159(7), 146(9), 131(17), 118(80), 117(100), 106(60), 105(80), 91(45), 77(20)
 $^1$H (500 MHz, CDCl$_3$):
 7.31 (ddm, J=8.3, 7.1, 2H), 7.27 (dm, J=8.3, 2H), 7.20 (tm, J=7.1, 1H), 3.41 (d, J=11.0, 1H), 3.35 (d, J=11.0, 1H), 2.31 (dq, J=10.6, 7.0, 1H), 1.34 (d, J=7.0, 3H), 1.28 (s, 3H), 0.87 (ddd, J=10.6, 8.8, 5.7, 1H), 0.52 (dd, J=8.8, 4.9, 1H), 0.12 (dd, J=5.7, 4.9, 1H)
 $^{13}$C (125 MHz, CDCl$_3$)
 147.2 (s), 128.3 (d), 126.0 (d), 126.0 (d), 72.4 (t), 39.8 (d), 29.7 (d), 23.6 (s), 22.6 (q), 16.6 (t), 15.3 (q)
Minor Isomer
 GC/MS (m/e):
 190 (M$^+$, <1), 172(1), 159(7), 146(5), 131(17), 118(80), 117(100), 106(60), 105(80), 91(45), 77(20)
 $^1$H (500 MHz, CDCl$_3$):
 7.29 (ddm, J=8.3, 7.1, 2H), 7.26 (dm, J=8.3, 2H), 7.18 (tm, J=7.1, 1H), 3.33 (d, J=10.4, 1H), 3.27 (d, J=10.4, 1H), 2.34 (dq, J=10.5, 7.0, 1H), 1.35 (d, J=7.0, 3H), 1.06 (s, 3H), 0.97 (ddd, J=10.5, 8.9, 5.5, 1H), 0.70 (dd, J=8.9, 4.7, 1H), 0.18 (dd, J=5.5, 4.7, 1H)

$^{13}$C (125 MHz, CDCl$_3$)

147.7 (s), 128.4 (d), 126.6 (d), 125.9 (d), 72.2 (t), 40.0 (d), 29.2 (d), 23.4 (s), 23.3 (q), 16.5 (t), 15.7 (q)

Synthesis Example 2

Synthesis of [1-Methyl-2-(1-phenylethyl)cyclopropyl]methanol

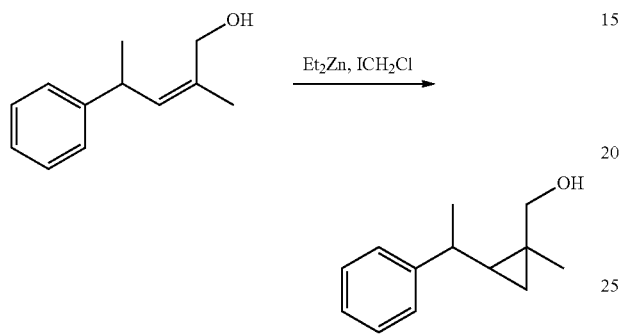

In a nitrogen atmosphere, a diethylzinc solution in toluene (concentration: 15% by weight, 69.8 g, 0.0848 mol) was placed in a 100 ml flask equipped with a stirrer, a dropping funnel, and a thermometer, and cooled to −20° C. Chloroiodomethane (29.9 g, 0.1696 mol) was placed in the dropping funnel, and added dropwise with the temperature being kept at −15 to −20° C. After completion of the dropwise addition, the mixture was stirred at −10 to −15° C. for 30 minutes. Then, the mixture was cooled to −25° C., and (Z)-2-methyl-4-phenylpent-2-en-1-ol (7.59 g, 0.0424 mol) was added dropwise over 60 minutes in the range from −20 to −25° C. After completion of the dropwise addition, stirring was continued at −15 to −25° C. for 60 minutes. Next, a 20% aqueous sulfuric acid solution (31.3 ml) was added, followed by stirring for 10 minutes. Then, the aqueous layer was separated. The organic layer was washed with water (30 ml) twice, and the solvent was recovered under reduced pressure to obtain a concentrated residue. This residue was purified by silica gel column chromatography (hexane:ethyl acetate=8:2) to obtain [(1S*,2S*)-1-methyl-2-((R*)-1-phenylethyl)cyclopropyl]methanol (4.93 g, 0.0259 mol, yield: 61%) as a main isomer, and [(1S*,2S*)-1-methyl-2-((S*)-1-phenylethyl)cyclopropyl]methanol (0.61 g, 0.0032 mol, yield 7.5%) as a minor isomer. The relative configurations of the main isomer and the minor isomer were determined by NOESY measurement.

Main Isomer

GC/MS (m/e):

172 (M$^+$-H$_2$O, 1), 157(5), 146(20), 131(27), 118(72), 117(100), 106(65), 105(75), 91(53), 77(25)

$^1$H (500 MHz, CDCl$_3$):

7.30 (ddm, J=7.9, 7.2, 2H), 7.25 (dm, J=7.9, 2H), 7.19 (tm, J=7.2, 1H), 3.70 (m, 2H), 2.35 (dq, J=10.6, 7.0, 1H), 1.38 (d, J=7.0, 3H), 1.30 (m, OH), 1.21 (s, 3H), 0.94 (ddd, J=10.6, 8.4, 5.9, 1H), 0.45 (dd, J=8.4, 4.8, 1H), 0.21 (dd, J=5.9, 4.8, 1H)

$^{13}$C (125 MHz, CDCl$_3$)

147.3 (s), 128.3 (d), 126.9 (d), 125.9 (d), 67.1 (t), 40.0 (d), 33.3 (d), 23.5 (s), 23.0 (q), 22.9 (q), 17.3 (t)

Minor Isomer

GC/MS (m/e):

190 (M$^+$, <1), 172(4), 157(10), 143(7), 131(17), 118(72), 117(100), 106(65), 105(67), 91(44), 77(20)

$^1$H (500 MHz, CDCl$_3$):

7.32 (ddm, J=8.3, 7.1, 2H), 7.28 (dm, J=8.3, 2H), 7.21 (tm, J=7.1, 1H), 3.52 (dd, J=11.6, 9.1, 1H), 3.33 (d, J=11.6, 1H), 2.34 (dq, J=10.6, 6.9, 1H), 1.34 (d, J=6.9, 3H), 1.13 (s, 3H), 1.06 (ddd, J=10.6, 8.3, 5.5, 1H), 0.66 (dd, J=8.3, 4.6, 1H), 0.40 (m, OH), 0.27 (dd, J=5.5, 4.6, 1H)

$^{13}$C (125 MHz, CDCl$_3$)

147.7 (s), 128.8 (d), 126.4 (d), 126.4 (d), 67.3 (t), 40.9 (d), 31.9 (d), 24.1 (q), 23.1 (s), 22.6 (q), 17.8 (t)

Synthesis Example 3

Synthesis of (1S*,2S*)-1-Methyl-2-((R*)-1-phenylethyl)cyclopropane-1-carb aldehyde

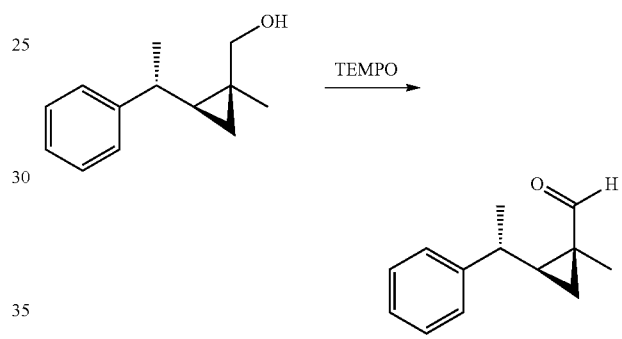

In a nitrogen atmosphere, [(1S*,2S*)-1-methyl-2-((R*)-1-phenylethyl)cyclopropyl]methanol (1.02 g, 0.00537 mol), potassium bromide (0.36 g), 2,2,6,6-tetramethylpiperidine 1-oxyl free radical (0.085 g), and toluene (10 ml) were placed in a 100 ml flask equipped with a stirrer, a dropping funnel, and a thermometer, and cooled to 0° C. An aqueous sodium hypochlorite solution (concentration: approximately 13.5%, 5.0 g, 0.0091 mol) was placed in the dropping funnel, and added dropwise with the temperature being kept at 0° C. After completion of the dropwise addition, the temperature was raised to 18° C. over 60 minutes. After that, the aqueous layer was separated, and the organic layer was washed with a 10% aqueous sodium thiosulfate solution and with water. The solvent was recovered under reduced pressure to obtain a concentrated residue of (1S*,2S*)-1-methyl-2-[(R*)-1-phenylethyl]cyclopropane-1-carb aldehyde (0.91 g, 0.0048 mol, yield: 89%).

GC/MS (m/e):

188 (M$^+$, 5), 159(7), 141(5), 128(20), 118(82), 117(100), 115(45), 105(43), 91(60), 83(60)77(44)

$^1$H (500 MHz, CDCl$_3$):

9.37 (s, 1H), 7.34 (ddm, J=8.3, 7.2, 2H), 7.28 (dm, J=8.3, 2H), 7.24 (tm, J=7.2, 1H), 2.71 (dq, J=10.4, 7.0, 1H), 1.51-1.42 (m, 2H), 1.32 (s, 3H), 1.30 (d, J=7.0, 3H), 1.09 (dd, J=7.5, 4.6, 1H)

$^{13}$C (125 MHz, CDCl$_3$)

202.7 (d), 145.6 (s), 128.5 (d), 126.7 (d), 126.5 (d), 40.1 (d), 38.8 (d), 32.9 (s), 22.5 (t), 21.9 (q), 18.4 (q)

Synthesis Example 4

Synthesis of 1-[(1S*,2S*)-1-Methyl-2-((R*)-1-phenylethyl)cyclopropyl]ethanol

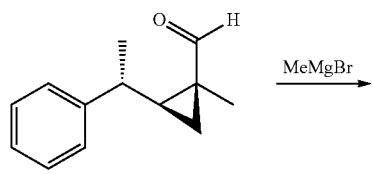

In a nitrogen atmosphere, methyl magnesium bromide (0.97 mol/L solution in tetrahydrofuran, 8.5 ml, 0.00825 mol) was placed in a 100 ml flask equipped with a stirrer, a dropping funnel, and a thermometer, and cooled to −10° C. (1S*,2S*)-1-Methyl-2-[(R*)-1-phenylethyl]cyclopropanecarbaldehyde (1.03 g, 0.0055 mol) was placed in the dropping funnel, and added dropwise in 5 minutes with the temperature being kept at −10° C. After completion of the dropwise addition, the mixture was stirred for 60 minutes. Then, a 20% aqueous sulfuric acid solution (4.5 g) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=10:1) to obtain (R*)-1-[(1S*,2S*)-1-methyl-2-((R*)-1-phenylethyl)cyclopropyl]ethanol (0.75 g, 0.00368 mol, yield: 67%) as a main isomer, and (S*)-1-[(1S*,2S*)-1-methyl-2-((R*)-1-phenylethyl)cyclopropyl]ethanol (0.205 g, 0.001 mol, yield: 18%) as a minor isomer.

The relative configurations of the main isomer and the minor isomer were determined by NOESY measurement.

Main Isomer

GC/MS (m/e):
186 (M$^+$-H$_2$O, 1), 171(6), 160(15), 145(7), 131(29), 118 (87), 117(100), 106(68), 105(86), 91(53), 77(26), 72(30), 70(30)

$^1$H (500 MHz, CDCl$_3$):
7.29 (ddm, J=8.3, 7.2, 2H), 7.24 (dm, J=8.3, 2H), 7.19 (tm, J=7.2, 1H), 3.60 (q, J=6.4, 1H), 2.46 (dq, J=10.4, 6.9, 1H), 1.46 (d, J=6.9, 3H), 1.31 (d, 6.4, 3H), 1.09 (s, 3H), 0.92 (ddd, J=10.4, 8.5, 5.9, 1H), 0.41 (dd, J=8.5, 4.9, 1H), 0.01 (dd, J=5.9, 4.9, 1H)

$^{13}$C (125 MHz, CDCl$_3$)
147.7 (s), 128.3 (d), 127.0 (d), 125.9 (d), 70.5 (d), 39.0 (d), 34.5 (d), 26.5 (s), 23.6 (q), 20.5 (q), 18.4 (q), 17.5 (t)

Minor Isomer

GC/MS (m/e):
186 (M$^+$-H$_2$O, 1), 171(7), 160(13), 145(7), 131(32), 118 (85), 117(100), 106(65), 105(84), 91(55), 77(27), 72(21), 70(29)

$^1$H (500 MHz, CDCl$_3$)
7.30 (ddm, J=8.3, 7.2, 2H), 7.21 (dm, J=8.3, 2H), 7.19 (tm, J=7.2, 1H), 3.58 (q, J=6.4, 1H), 2.39 (dq, J=10.5, 6.9, 1H), 1.37 (d, J=6.4, 3H), 1.36 (d, 6.9, 3H), 1.09 (s, 3H), 0.95 (ddd, J=10.5, 8.6, 5.7, 1H), 0.46 (dd, J=8.6, 4.6, 1H), 0.19 (dd, J=5.7, 4.6, 1H)

$^{13}$C (125 MHz, CDCl$_3$)
147.5 (s), 128.3 (d), 126.9 (d), 126.0 (d), 70.8 (d), 39.1 (d), 34.1 (d), 27.5 (s), 23.6 (q), 20.4 (q), 18.9 (t), 18.7 (q)

Synthesis Example 5

Synthesis of [1,2-Dimethyl-2-(1-phenylethyl)cyclopropyl]methanol

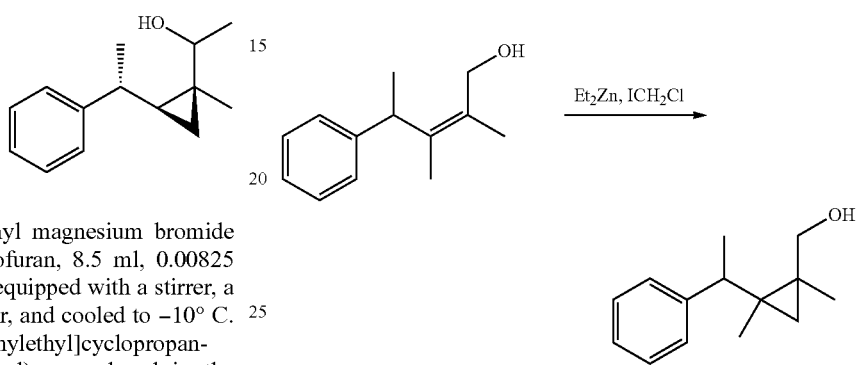

In a nitrogen atmosphere, a diethylzinc solution in toluene (concentration: 15% by weight, 10.9 g, 0.0132 mol) was placed in a 100 ml flask equipped with a stirrer, a dropping funnel, and a thermometer, and cooled to −15° C. Chloroiodomethane (4.68 g, 0.0265 mol) was placed in the dropping funnel, and added dropwise with the temperature being kept at −15 to −20° C. After completion of the dropwise addition, the mixture was stirred at −15° C. for 30 minutes. Then, the mixture was cooled to −15° C., and (Z)-2,3-dimethyl-4-phenylpent-2-en-1-ol (1.26 g, 0.00663 mol) was added dropwise over 20 minutes at −10 to −15° C. After completion of the dropwise addition, stirring was continued at 12° C. for 60 minutes. Next, a 20% aqueous sulfuric acid solution (4.8 ml) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=9:1) to obtain [(1S*,2S*)-1,2-dimethyl-2-((S*)-1-phenylethyl)cyclopropyl]methanol (0.47 g, 0.0023 mol, yield: 35%) as a main isomer, and [(1S*,2S*)-1,2-dimethyl-2-((R*)-1-phenylethyl)cyclopropyl]methanol (0.45 g, 0.0022 mol, yield: 33%) as a minor isomer. The relative configurations of the main isomer and the minor isomer were determined by NOESY measurement.

Main Isomer

GC/MS (m/e):
204 (M$^+$, <1), 186(3), 171(25), 149(45), 132(39), 131 (79), 117(86), 115(36), 106(44), 105(100), 99(37), 91(60), 77(31)

$^1$H (500 MHz, CDCl$_3$):
7.32-7.27 (m, 4H), 7.20 (m, 1H), 3.78 (m, 2H), 2.68 (q, 7.2, 1H), 1.36 (d, J=7.2, 3H), 1.35 (OH), 1.25 (s, 3H), 0.92 (s, 3H), 0.73 (d, J=4.8, 1H), 0.22 (d, J=4.8, 1H)

$^{13}$C (125 MHz, CDCl$_3$)
145.1 (s), 128.0 (d), 127.9 (d), 125.9 (d), 68.2 (t), 42.3 (d), 30.2 (s), 26.7 (s), 25.5 (t), 18.3 (q), 16.8 (q), 14.7 (q)

Minor Isomer

GC/MS (m/e):

204 (M+, <1), 186(3), 171(24), 149(44), 132(46), 131(89), 117(94), 115(38), 106(48), 105(100), 99(38), 91(65), 77(35)

$^1$H (500 MHz, CDCl$_3$):

7.32 (ddm, J=7.8, 7.0, 2H), 7.28 (dm, J=7.8, 2H), 7.19 (tm, J=7.0, 1H), 3.64 (m, 2H), 2.64 (q, 7.1, 1H), 1.40 (d, J=7.1, 3H), 1.24 (s, 3H), 1.08 (s, 3H), 0.90 (t, J=6.7, OH), 0.45 (d, J=4.6, 1H), 0.29 (d, J=4.6, 1H)

$^{13}$C (125 MHz, CDCl$_3$)

145.3 (s), 128.4 (d), 127.5 (d), 126.0 (d), 68.3 (t), 42.5 (d), 29.3 (s), 28.5 (s), 25.1 (t), 18.9 (q), 18.2 (q), 15.6 (q)

Synthesis Example 6

Synthesis of [1-Methyl-2-(1-(4-methylphenyl)ethyl)cyclopropyl]methanol

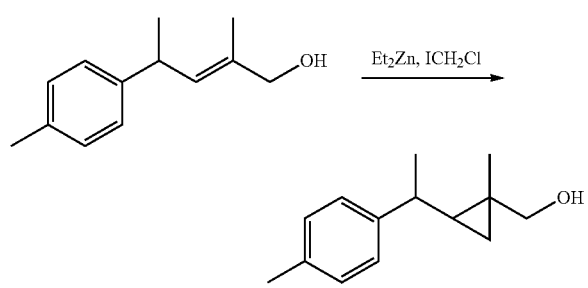

In a nitrogen atmosphere, a diethylzinc solution in toluene (concentration: 15% by weight, 5.3 g, 0.0064 mol) was placed in a 100 ml flask equipped with a stirrer, a dropping funnel, and a thermometer, and cooled to −20° C. Chloroiodomethane (2.26 g, 0.0128 mol) was placed in the dropping funnel, and added dropwise with the temperature being kept at −15 to −20° C. After completion of the dropwise addition, the mixture was stirred at −10 to −15° C. for 10 minutes. Then, the mixture was cooled to −20° C., and (E)-2-methyl-4-(4-methylphenyl)pent-2-en-1-ol (0.60 g, 0.0032 mol) was added dropwise over 10 minutes at the same temperature. After completion of the dropwise addition, stirring was continued at −15 to −25° C. for 60 minutes. Next, a 20% aqueous sulfuric acid solution (2.5 ml) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=9:1) to obtain [(1R*,2S*)-1-methyl-2-((R*)-1-(4-methylphenyl)ethyl)cyclopropyl]methanol (0.24 g, 0.00118 mol, yield: 36%) as a main isomer, and [(1R*,2S*)-1-methyl-2-((S*)-1-(4-methylphenyl)ethyl)cyclopropyl]methanol (0.013 g, 0.000064 mol, yield: 2%) as a minor isomer. The relative configurations of the main isomer and the minor isomer were determined by NOESY measurement.

Main Isomer

GC/MS (m/e):

186 (M+-H$_2$O, 2), 173(13), 160(13), 149(19), 145(23), 132(80), 131(64), 120(62), 119(88), 117(100), 115(48), 105(40), 91(62), 77(21)

$^1$H (500 MHz, CDCl$_3$):

7.16 (dm, J=8.2, 2H), 7.12 (dm, J=8.2, 2H), 3.41 (d, J=11.0, 1H), 3.35 (d, J=11.0, 1H), 2.33 (s, 3H) 2.27 (dq, J=10.6, 7.0, 1H), 1.32 (d, J=7.0, 3H), 1.28 (s, 3H), 0.84 (ddd, J=10.6, 8.8, 5.7, 1H), 0.52 (dd, J=8.8, 4.8, 1H), 0.11 (dd, J=5.7, 4.8, 1H)

$^{13}$C (125 MHz, CDCl$_3$)

144.2 (s), 135.4 (s), 129.0 (d), 126.8 (d), 72.5 (t), 39.4 (d), 29.9 (d), 23.6 (s), 22.7 (q), 21.0 (q), 16.6 (t), 15.3 (q)

Minor Isomer

GC/MS (m/e):

204 (M+, <1), 186(7), 173(16), 157(8), 149(23), 145(20), 132(98), 131(84), 120(66), 119(100), 117(96), 115(53), 105(42), 91(64), 77(24)

$^1$H (500 MHz, CDCl$_3$):

7.14 (dm, J=8.2, 2H), 7.10 (dm, J=8.2, 2H), 3.34 (d, J=10.8, 1H), 3.27 (d, J=10.8, 1H), 2.32 (s, 3H) 2.31 (dq, J=10.6, 7.0, 1H), 1.33 (d, J=7.0, 3H), 1.06 (s, 3H), 0.95 (ddd, J=10.6, 8.9, 5.6, 1H), 0.68 (dd, J=8.9, 4.7, 1H), 0.18 (dd, J=5.6, 4.7, 1H)

$^{13}$C (125 MHz, CDCl$_3$)

144.6 (s), 135.2 (s), 129.1 (d), 126.4 (d), 72.3 (t), 39.6 (d), 29.3 (d), 23.36 (q), 23.35 (s), 20.9 (q), 16.5 (t), 15.7 (q)

Synthesis Example 7

Synthesis of [1-Methyl-2-(1-(4-methylphenyl)ethyl)cyclopropyl]methanol

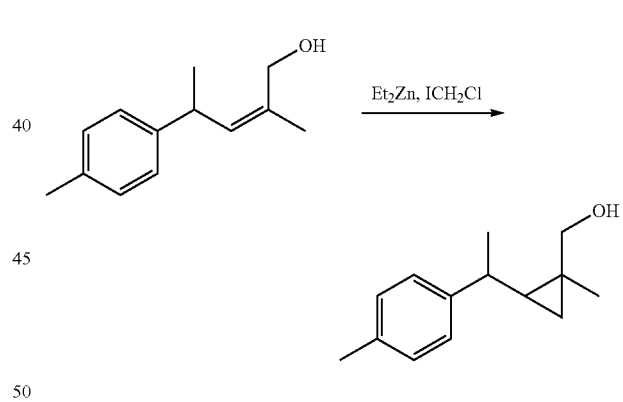

In a nitrogen atmosphere, a diethylzinc solution in toluene (concentration: 15% by weight, 9.4 g, 0.0114 mol) was placed in a 100 ml flask equipped with a stirrer, a dropping funnel, and a thermometer, and cooled to −15° C. Chloroiodomethane (4.02 g, 0.0228 mol) was placed in the dropping funnel, and added dropwise with the temperature being kept at −15° C. After completion of the dropwise addition, the mixture was stirred at −10 to −15° C. for 20 minutes. Then, the mixture was cooled to −25° C., and (Z)-2-methyl-4-(4-methylphenyl)pent-2-en-1-ol (1.08 g, 0.0057 mol) was added dropwise at −20 to −25° C. over 20 minutes. After completion of the dropwise addition, stirring was continued at −15 to −25° C. for 60 minutes. Next, a 20% aqueous sulfuric acid solution (4.2 ml) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=9:1) to obtain [(1S*,2S*)-1-methyl-2-((R*)-1-(4-methylphenyl)ethyl)cyclopropyl]methanol (0.79 g, 0.0038 mol, yield: 68%) as a main isomer, and [(1S*,2S*)-1-methyl-2-((S*)-1-(4-methylphenyl)ethyl)cyclopropyl] methanol (0.21 g, 0.0010 mol, yield: 18%) as a minor isomer.

The relative configurations of the main isomer and the minor isomer were determined by NOESY measurement.

Main Isomer

GC/MS (m/e):

186 ($M^+$-$H_2O$, 1), 173(9), 171(7), 160(18), 149(16), 145 (25), 132(76), 131(66), 120(65), 119(82), 117(100), 115(47), 105(46), 91(56), 77(19)

$^1$H (500 MHz, $CDCl_3$):

7.14 (dm, J=8.3, 2H), 7.12 (dm, J=8.3, 2H), 3.71 (d, J=11.3, 1H), 3.69 (d, J=11.3, 1H), 2.32 (s, 3H) 2.32 (dq, J=10.6, 6.9, 1H), 1.36 (d, J=6.9, 3H), 1.29 (br. s, OH), 1.20 (s, 3H), 0.92 (ddd, J=10.6, 8.4, 5.8, 1H), 0.44 (dd, J=8.4, 4.8, 1H), 0.20 (dd, J=5.8, 4.8, 1H)

$^{13}$C (125 MHz, $CDCl_3$)

144.3 (s), 135.4 (s), 129.0 (d), 126.7 (d), 67.1 (t), 39.6 (d), 33.4 (d), 23.5 (s), 23.1 (q), 22.9 (q), 21.0 (q), 17.3 (t)

Minor Isomer

GC/MS (m/e):

186 ($M^+$-$H_2O$, 9), 173(11), 171(15), 157(10), 149(19), 145(20), 132(91), 131(90), 120(70), 119(95), 117(100), 115 (54), 105(43), 91(66), 77(23)

$^1$H (500 MHz, $CDCl_3$):

7.17 (dm, J=8.2, 2H), 7.13 (dm, J=8.2, 2H), 3.54 (dd, J=12.6, 9.7, 1H), 3.33 (dd, J=12.6, 1.2, 1H), 2.31 (s, 3H) 2.30 (dq, J=10.6, 6.9, 1H), 1.32 (d, J=6.9, 3H), 1.13 (s, 3H), 1.03 (ddd, J=10.6, 8.3, 5.4, 1H), 0.64 (dd, J=8.3, 4.6, 1H), 0.39 (br. d, J=9, 7, OH), 0.25 (dd, J=5.4, 4.6, 1H)

$^{13}$C (125 MHz, $CDCl_3$)

144.7 (s), 135.9 (s), 129.5 (d), 126.3 (d), 67.4 (t), 40.5 (d), 32.0 (d), 24.2 (q), 23.1 (s), 22.6 (q), 21.0 (q), 17.9 (t)

Synthesis Example 8

Synthesis of [1-Methyl-2-(1-(3-methylphenyl)ethyl)cyclopropyl]methanol

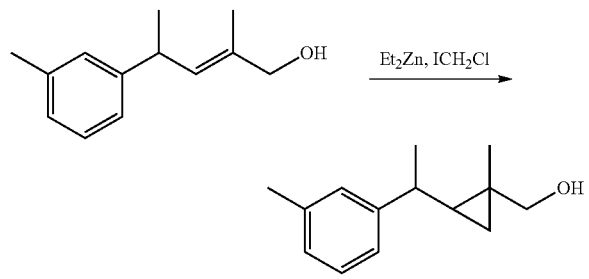

In a nitrogen atmosphere, a diethylzinc solution in toluene (concentration: 15% by weight, 6.92 g, 0.0084 mol) was placed in a 100 ml flask equipped with a stirrer, a dropping funnel, and a thermometer, and cooled to −25° C. Chloroiodomethane (2.96 g, 0.0168 mol) was placed in the dropping funnel, and added dropwise with the temperature being kept at −20 to −25° C. After completion of the dropwise addition, the mixture was stirred at −10 to −20° C. for 15 minutes. Then, the mixture was cooled to −25° C., and (E)-2-methyl-4-(3-methylphenyl)pent-2-en-1-ol (0.80 g, 0.0042 mol) was added dropwise over 20 minutes at the same temperature. After completion of the dropwise addition, stirring was continued at −10 to −25° C. for 20 minutes. Next, a 20% aqueous sulfuric acid solution (3.1 ml) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=9:1) to obtain [(1R*,2S*)-1-methyl-2-((R*)-1-(3-methylphenyl)ethyl)cyclopropyl]methanol (0.38 g, 0.0019 mol, yield: 45%) as a main isomer, and [(1R*,2S*)-1-methyl-2-((S*)-1-(3-methylphenyl)ethyl)cyclopropyl]methanol (0.014 g, 0.000069 mol, yield 1.6%) as a minor isomer. The relative configurations of the main isomer and the minor isomer were determined by NOESY measurement.

Main Isomer

GC/MS (m/e):

186 ($M^+$-$H_2O$, 1), 173(16), 160(15), 145(30), 132(81), 131(66), 120(73), 119(81), 117(100), 115(46), 105(36), 91(49), 77(16)

$^1$H (500 MHz, $CDCl_3$):

7.19 (dd, J=8.0, 7.4, 1H), 7.07 (br. s, 1H), 7.06 (dm, 8.0, 1H), 7.02 (dm, 7.4, 1H), 3.42 (d, J=11.0, 1H), 3.36 (d, J=11.0, 1H), 2.35 (s, 3H) 2.26 (dq, J=10.6, 7.0, 1H), 1.33 (d, J=7.0, 3H), 1.28 (s, 3H), 0.86 (ddd, J=10.6, 8.8, 5.7, 1H), 0.52 (dd, J=8.8, 4.8, 1H), 0.12 (dd, J=5.7, 4.8, 1H)

$^{13}$C (125 MHz, $CDCl_3$)

147.2 (s), 137.8 (s), 128.2 (d), 127.7 (d), 126.7 (d), 124.0 (d), 72.4 (t), 39.7 (d), 29.7 (d), 23.6 (s), 22.7 (q), 21.5 (q), 16.6 (t), 15.3 (q)

Minor Isomer

GC/MS (m/e):

204 ($M^+$, <1), 186(4), 173(17), 157(10), 149(11), 145(21), 132(93), 131(80), 120(79), 119(88), 117(100), 115(54), 105 (42), 91(71), 77(26)$^1$H (500 MHz, $CDCl_3$):

7.18 (ddm, J=8.4, 7.4, 1H), 7.06 (br. s, 1H), 7.05 (dm, 8.4, 1H), 6.99 (dm, 7.4, 1H), 3.33 (d, J=10.9, 1H), 3.27 (d, J=10.9, 1H), 2.33 (s, 3H) 2.30 (dq, J=10.5, 7.0, 1H), 1.34 (d, J=7.0, 3H), 1.09 (br. s, OH) 1.06 (s, 3H), 0.96 (ddd, J=10.5, 8.9, 5.5, 1H), 0.68 (dd, J=8.9, 4.7, 1H), 0.17 (dd, J=5.5, 4.7, 1H)

$^{13}$C (125 MHz, $CDCl_3$)

147.6 (s), 137.8 (s), 128.3 (d), 127.4 (d), 126.6 (d), 123.6 (d), 72.2 (t), 39.9 (d), 29.2 (d), 23.34 (s), 23.28 (q), 21.5 (q), 16.5 (t), 15.7 (q)

Synthesis Example 9

Synthesis of [1-Methyl-2-(1-(3-methylphenyl)ethyl)cyclopropyl]methanol

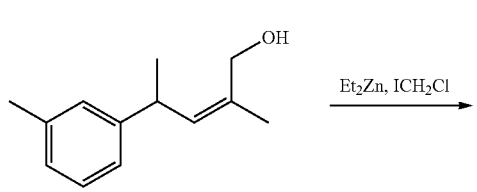

27
-continued

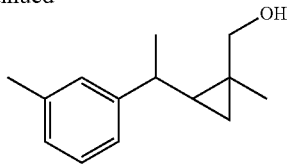

In a nitrogen atmosphere, a diethylzinc solution in toluene (concentration: 15% by weight, 9.4 g, 0.0114 mol) was placed in a 100 ml flask equipped with a stirrer, a dropping funnel, and a thermometer, and cooled to −15° C. Chloroiodomethane (4.02 g, 0.0228 mol) was placed in the dropping funnel, and added dropwise with the temperature being kept at −15 to −20° C. After completion of the dropwise addition, the mixture was stirred at −10 to −15° C. for 20 minutes. Then, the mixture was cooled to −25° C., and (Z)-2-methyl-4-(3-methylphenyl)pent-2-en-1-ol (1.09 g, 0.0057 mol) was added dropwise at −20 to −25° C. over 20 minutes. After completion of the dropwise addition, stirring was continued at −15 to −25° C. for 40 minutes. Next, a 20% aqueous sulfuric acid solution (4.2 ml) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=9:1) to obtain [(1S*,2S*)-1-methyl-2-((R*)-1-(3-methylphenyl)ethyl)cyclopropyl]methanol (0.83 g, 0.0041 mol, yield: 70%) as a main isomer, and [(1S*,2S*)-1-methyl-2-((S*)-1-(3-methylphenyl)ethyl)cyclopropyl]methanol (0.20 g, 0.00099 mol, yield: 17%) as a minor isomer. The relative configurations of the main isomer and the minor isomer were determined by NOESY measurement.

Main Isomer

GC/MS (m/e):

186 ($M^+$-$H_2O$, 1), 171(7), 160(20), 145(30), 132(66), 131(65), 120(69), 119(71), 117(100), 115(50), 105(46), 91(62), 77(21)

$^1$H (500 MHz, $CDCl_3$):

7.19 (dt, J=0.9, 7.4, 1H), 7.05 (s, 1H), 7.04 (dm, J=7.4, 1H), 7.01 (dm, J=7.4, 1H), 3.71 (d, J=11.3, 1H), 3.68 (d, J=11.3, 1H), 2.34 (s, 3H) 2.32 (dq, J=10.6, 7.0, 1H), 1.36 (d, J=7.0, 3H), 1.31 (br. s, OH) 1.20 (s, 3H), 0.93 (ddd, J=10.6, 8.4, 5.8, 1H), 0.44 (dd, J=8.4, 4.8, 1H), 0.21 (dd, J=5.8, 4.8, 1H)

$^{13}$C (125 MHz, $CDCl_3$)

147.3 (s), 137.8 (s), 128.2 (d), 127.7 (d), 126.7 (d), 123.9 (d), 67.1 (t), 40.0 (d), 33.3 (d), 23.5 (s), 23.1 (q), 22.9 (q), 21.5 (q), 17.3 (t)

Minor Isomer

GC/MS (m/e):

186 ($M^+$-$H_2O$, 7), 171(18), 157(11), 145(22), 132(81), 131(95), 120(77), 119(83), 117(100), 115(63), 105(45), 91(76), 77(25)

$^1$H (500 MHz, $CDCl_3$):

7.21 (dd, J=8, 7, 1H), 7.08 (dm, J=7, 1H), 7.07 (m, 1H), 7.02 (dm, J=8, 1H), 3.53 (dd, J=11.7, 10.0, 1H), 3.34 (dd, J=11.7, 2.8, 1H), 2.34 (s, 3H) 2.30 (dq, J=10.6, 6.9, 1H), 1.33 (d, J=6.9, 3H), 1.13 (s, 3H), 1.04 (ddd, J=10.6, 8.3, 5.4, 1H), 0.64 (dd, J=8.3, 4.6, 1H), 0.42 (dd, J=10.0, 2.8, OH) 0.26 (dd, J=5.4, 4.6, 1H)

$^{13}$C (125 MHz, $CDCl_3$)

147.7 (s), 138.4 (s), 128.7 (d), 127.3 (d), 127.2 (d), 123.4 (d), 67.4 (t), 40.8 (d), 31.9 (d), 24.1 (q), 23.1 (s), 22.6 (q), 21.5 (q), 17.9 (t)

28

Synthesis Example 10

Synthesis of [1-Methyl-2-(1-(2-methylphenyl)ethyl)cyclopropyl]methanol

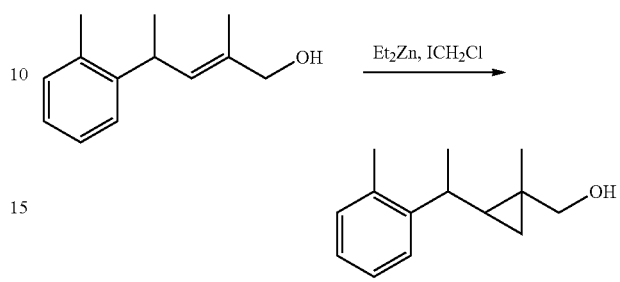

In a nitrogen atmosphere, a diethylzinc solution in toluene (concentration: 15% by weight, 6.92 g, 0.0084 mol) was placed in a 100 ml flask equipped with a stirrer, a dropping funnel, and a thermometer, and cooled to −20° C. Chloroiodomethane (2.96 g, 0.0168 mol) was placed in the dropping funnel, and added dropwise with the temperature being kept at −15 to −20° C. After completion of the dropwise addition, the mixture was stirred at −5 to −15° C. for 10 minutes. Then, the mixture was cooled to −25° C., and (E)-2-methyl-4-(2-methylphenyl)pent-2-en-1-ol (0.80 g, 0.0042 mol) was added dropwise at −20 to −25° C. over 20 minutes. After completion of the dropwise addition, stirring was continued at −15 to −25° C. for 60 minutes. Next, a 20% aqueous sulfuric acid solution (3.1 ml) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=9:1) to obtain [(1R*,2S*)-1-methyl-2-((R*)-1-(2-methylphenyl)ethyl)cyclopropyl]methanol (0.32 g, 0.0016 mol, yield: 37%) as a main isomer, and [(1R*,2S*)-1-methyl-2-((S*)-1-(2-methylphenyl)ethyl)cyclopropyl]methanol (0.025 g, 0.00012 mol, yield: 3%) as a minor isomer.

The relative configurations of the main isomer and the minor isomer were determined by NOESY measurement.

Main Isomer

GC/MS (m/e):

204 ($M^+$, <1), 186(5), 171(13), 157(10), 149(10), 145 (15), 143(20), 132(64), 131(63), 120(74), 119(87), 117 (100), 115(53), 105(35), 91(56), 77(18)

$^1$H (500 MHz, $CDCl_3$):

7.36 (dd, J=7.7, 1.0, 1H), 7.19 (tm, J=7.7, 1H), 7.13 (dm, J=7.7, 1H), 7.09 (dt, J=1.4, 7.7, 1H), 3.45 (d, J=11.0, 1H), 3.38 (d, J=11.0, 1H), 2.62 (dq, J=10.5, 6.9, 1H), 2.31 (s, 3H), 1.30 (s, 3H), 1.27 (d, J=6.9, 3H), 0.99 (ddd, J=10.5, 8.9, 5.8, 1H), 0.51 (dd, J=8.9, 4.9, 1H), 0.02 (dd, J=5.8, 4.9, 1H)

$^{13}$C (125 MHz, $CDCl_3$)

145.6 (s), 134.7 (s), 130.2 (d), 126.2 (d), 126.1 (d), 125.6 (d), 72.5 (t), 34.6 (d), 29.1 (d), 23.6 (s), 22.9 (q), 19.6 (q), 16.5 (t), 15.5 (q)

Minor Isomer

GC/MS (m/e):

186 ($M^+$-$H_2O$, 6), 173(17), 171(15), 157(14), 149(17), 143(25), 132(62), 131(70), 129(30), 128(40), 120(52), 119 (72), 117(100), 115(66), 105(32), 91(60), 77(23)

$^1$H (500 MHz, $CDCl_3$):

7.33 (dd, J=7.5, 0.8, 1H), 7.19 (dt, J=2.0, 7.5, 1H), 7.11 (dm, J=7.5, 1H), 7.08 (dt, J=1.4, 7.5, 1H), 3.35 (d, J=10.8,

1H), 3.31 (d, J=10.8, 1H), 2.48 (dq, J=10.4, 6.9, 1H), 2.29 (s, 3H), 1.27 (d, J=6.9, 3H), 1.15 (ddd, J=10.4, 8.8, 5.4, 1H), 1.09 (br. s), 0.90 (s, 3H), 0.74 (dd, J=8.8, 4.6, 1H), 0.22 (dd, J=5.4, 4.6, 1H)

$^{13}$C (125 MHz, CDCl$_3$)

146.2 (s), 134.4 (s), 130.2 (d), 126.3 (d), 125.6 (d), 125.2 (d), 72.2 (t), 36.3 (d), 28.5 (d), 23.0 (s), 22.9 (q), 19.2 (q), 17.3 (t), 15.5 (q)

Synthesis Example 11

Synthesis of [1-Methyl-2-(1-(2-methylphenyl)ethyl)cyclopropyl]methanol

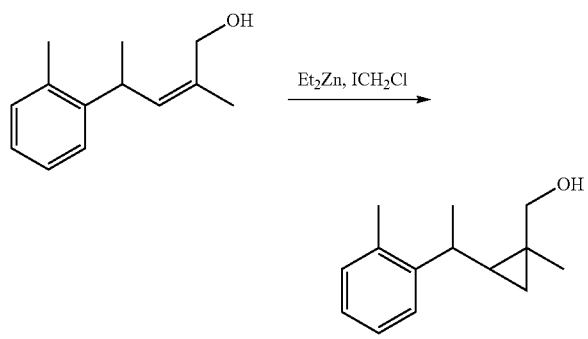

In a nitrogen atmosphere, a diethylzinc solution in toluene (concentration: 15% by weight, 5.4 g, 0.0066 mol) was placed in a 100 ml flask equipped with a stirrer, a dropping funnel, and a thermometer, and cooled to −20° C. Chloroiodomethane (2.33 g, 0.0132 mol) was placed in the dropping funnel, and added dropwise with the temperature being kept at −15 to −20° C. After completion of the dropwise addition, the mixture was stirred at −5 to −15° C. for 20 minutes. Then, the mixture was cooled to −25° C., and (Z)-2-methyl-4-(2-methylphenyl)pent-2-en-1-ol (0.62 g, 0.0033 mol) was added dropwise at −20 to −25° C. over 15 minutes. After completion of the dropwise addition, stirring was continued at −15 to −25° C. for 20 minutes. Next, a 20% aqueous sulfuric acid solution (2.5 ml) was added, followed by stirring for 10 minutes. Then, the aqueous layer was separated. The organic layer was washed with water (10 ml) twice, and the solvent was recovered under reduced pressure to obtain a concentrated residue. This residue was purified by silica gel column chromatography (hexane:ethyl acetate=9:1) to obtain [(1S*,2S*)-1-methyl-2-((R*)-1-(2-methylphenyl)ethyl)cyclopropyl]methanol (0.47 g, 0.0023 mol, yield: 70%) as a main isomer, and [(1S*,2S*)-1-methyl-2-((S*)-1-(2-methylphenyl)ethyl)cyclopropyl]methanol (0.12 g, 0.00059 mol, yield: 17%) as a minor isomer. The relative configurations of the main isomer and the minor isomer were determined by NOESY measurement.

Main Isomer

GC/MS (m/e):

186 (M$^+$-H$_2$O, <1), 173(4), 171(6), 160(8), 149(9), 145 (18), 143(15), 132(55), 131(62), 120(76), 119(77), 117 (100), 115(56), 105(38), 91(59), 77(19)

$^1$H (500 MHz, CDCl$_3$):

7.35 (dd, J=7, 1.1, 1H), 7.19 (dt, J=1.8, 7, 1H), 7.12 (dd, J=7, 1.8, 1H), 7.08 (dt, J=1.3, 7, 1H), 3.725 (d, J=11.5, 1H), 3.715 (d, J=11.5, 1H), 2.67 (dq, J=10.5, 6.9, 1H), 2.29 (s, 3H) 1.32 (d, J=6.9, 3H), 1.23 (s, 3H), 1.06 (ddd, J=10.5, 8.4, 5.9, 1H), 0.43 (dd, J=8.4, 4.8, 1H), 0.11 (dd, J=5.9, 4.8, 1H)

$^{13}$C (125 MHz, CDCl$_3$)

145.8 (s), 134.7 (s), 130.2 (d), 126.2 (d), 126.1 (d), 125.6 (d), 67.3 (t), 34.8 (d), 32.6 (d), 23.5 (s), 23.2 (q), 23.0 (q), 19.6 (q), 17.1 (t)

Minor Isomer

GC/MS (m/e):

186 (M$^+$-H$_2$O, 2), 173(12), 171(8), 157(8), 149(14), 145 (14), 143(17), 132(69), 131(73), 120(64), 119(67), 117 (100), 115(64), 105(36), 91(73), 77(22)

$^1$H (500 MHz, CDCl$_3$):

7.41 (dd, J=7, 0.9, 1H), 7.22 (dt, J=2.2, 7, 1H), 7.13 (dm, J=7, 1H), 7.11 (dt, J=1.3, 7, 1H), 3.47 (dd, J=11.7, 9, 1H), 3.17 (d, J=11.7, 1H), 2.52 (dq, J=10.4, 6.8, 1H), 2.30 (s, 3H) 1.28 (d, J=6.8, 3H), 1.18 (ddd, J=10.4, 8.2, 5.4, 1H), 1.15 (s, 3H), 0.70 (dd, J=8.2, 4.2, 1H), 0.29 (dd, J=5.4, 4.2, 1H), 0.17 (br. d, J=9, OH)

$^{13}$C (125 MHz, CDCl$_3$)

145.8 (s), 134.6 (s), 130.6 (d), 126.7 (d), 126.2 (d), 125.4 (d), 67.6 (t), 37.0 (d), 31.5 (d), 22.91 (s), 22.88 (q), 22.5 (q), 19.1 (q), 18.6 (t)

Synthesis Example 12

Synthesis of 2-[(1R*,2S*)-1-Methyl-2-(1-phenylethyl)cyclopropyl]acetaldehyde

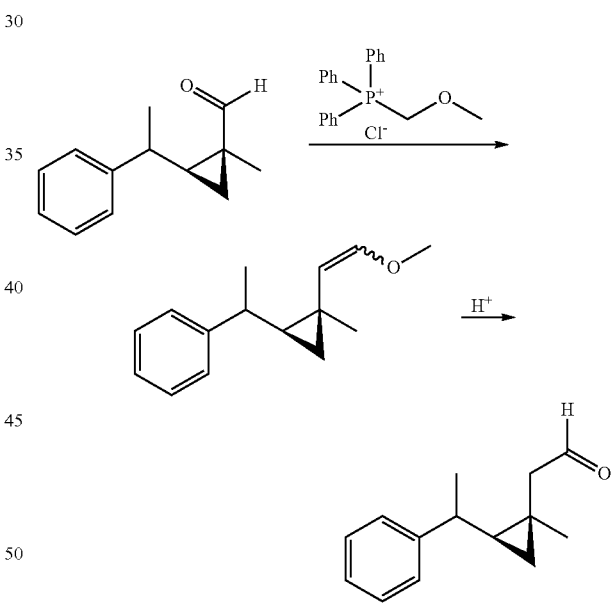

In a nitrogen atmosphere, (methoxymethyl)triphenylphosphonium chloride (5.0 g, 0.0146 mol) and tetrahydrofuran (20 ml) were placed in a 200 ml flask equipped with a stirrer, a dropping funnel, and a thermometer, and cooled to −40° C. A solution of potassium t-butoxide (1.63 g, 0.146 mol) in tetrahydrofuran (10 ml) was placed in the dropping funnel, and added dropwise with the temperature being kept at −35 to −40° C. After completion of the dropwise addition, the mixture was stirred at the same temperature for 5 minutes. Then, (1S*,2S*)-1-methyl-2-(1-phenylethyl)cyclopropanecarbaldehyde (1.5 g, 0.0080 mol, a mixture of two diastereomers at a component ratio of 1:2) was added dropwise over 5 minutes. After completion of the dropwise addition, the temperature was raised to −20° C., and stirring was continued for 2 hours. Next, a saturated aqueous ammonium chloride solution (20 ml) and hexane (30 ml) were added, followed by stirring for 10 minutes. Then, the aqueous layer was separated. The organic layer was washed with water (10 ml) twice, and the solvent was recovered under reduced pressure. The precipitated white solid was filtered, and the residue was obtained. Next, in a nitrogen atmosphere, the residue (1.33 g) obtained as above, acetonitrile (6 ml), and a 5% aqueous sulfuric acid solution (2 ml) were placed in a 100 ml flask equipped with a stirrer, a reflux tube, and a thermometer, and stirred at 55° C. for 1 hour. After that, toluene (10 ml) was added, and the aqueous layer was separated. The organic layer was washed with water, and the solvent was recovered under reduced pressure to obtain a concentrated residue. This residue was purified by silica gel column chromatography (hexane:ethyl acetate=8:2) to obtain 2-[(1R*,2S*)-1-methyl-2-(1-phenylethyl)cyclopropyl]acetaldehyde (a mixture of tow diastereomers, 0.56 g, 0.0028 mol, yield: 35%).

Main Isomer

GC/MS (m/e):

202 (M+, <1), 187(<1), 169(1), 158(9), 143(14), 128(11), 118(100), 117(85), 105(90), 97(56), 91(36), 77(22)

Minor Isomer

GC/MS (m/e):

202 (M+, <1), 187(<1), 169(1), 158(9), 143(16), 128(11), 118(99), 117(76), 105(100), 97(51), 91(39), 77(23)

$^{13}C$ (125 MHz, CDCl$_3$): data of mixture 203.5 (d), 203.1 (d), 146.9 (s), 146.8 (s), 128.5 (d), 128.4 (d), 126.9 (d), 126.6 (d), 126.1 (d), 48.0 (t), 47.9 (t), 41.4 (d), 40.6 (d), 31.7 (d), 30.6 (d), 25.5 (q), 25.2 (q), 23.8 (q), 22.5 (q), 18.6 (t), 18.3 (t), 17.1 (s), 16.7 (s)

Synthesis Example 13

Synthesis of 2-[(1R*,2S*)-1-Methyl-2-(1-phenylethyl)cyclopropyl]ethanol

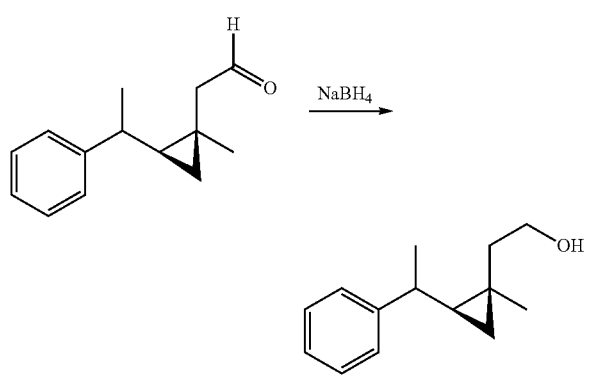

In a nitrogen atmosphere, 2-[(1R*,2S*)-1-methyl-2-(1-phenylethyl)cyclopropyl]acetaldehyde (a mixture of two diastereomers at a component ratio of 1:2, 0.20 g, 0.00099 mol), cyclopentyl methyl ether (4 ml), and sodium borohydride (0.05 g, 0.0013 mol) were placed in a 30 ml flask equipped with a stirrer, a dropping funnel, and a thermometer, and methanol (0.05 g) was added at 20° C. with stirring. The mixture was stirred at the same temperature for 60 minutes. Next, a 5% aqueous sulfuric acid solution (1.3 g) was added, followed by stirring for 10 minutes. Then, the aqueous layer was separated. The organic layer was washed with water (2 ml) twice, and the solvent was recovered under reduced pressure to obtain a concentrated residue. This residue was purified by silica gel column chromatography (hexane:ethyl acetate=8:2) to obtain 2-[(1R*,2S*)-1-methyl-2-(1-phenylethyl)cyclopropyl]ethanol (a mixture of two diastereomers at a component ratio of 1:2, 0.19 g, 0.00093 mol, yield: 94%).

Main Isomer

GC/MS (m/e):

204 (M+, <1), 189(<1), 171(1), 159(7), 143(6), 131(23), 118(100), 117(51), 105(87), 91(28), 77(15)

Minor Isomer

GC/MS (m/e):

204 (M+, <1), 189(<1), 171(2), 159(10), 143(8), 131(27), 118(92), 117(47), 105(100), 91(30), 77(16)

$^{13}C$ (125 MHz, CDCl$_3$): data of mixture 147.7 (s), 147.5 (s), 128.29 (d), 128.26 (d), 126.9 (d), 126.7 (d), 125.9 (d), 125.8 (d), 61.7 (t), 61.5 (t), 40.5 (d), 40.1 (d), 36.6 (t), 36.4 (t), 32.6 (d), 31.3 (d), 25.1 (q), 24.7 (q), 23.8 (q), 22.6 (q), 18.5 (t), 18.33 (t), 18.30 (s), 18.0 (s)

Synthesis Example 14

Synthesis of 1-[(1R*,2S*)-1-Methyl-2-(1-phenylethyl)cyclopropyl]propane-2-ol

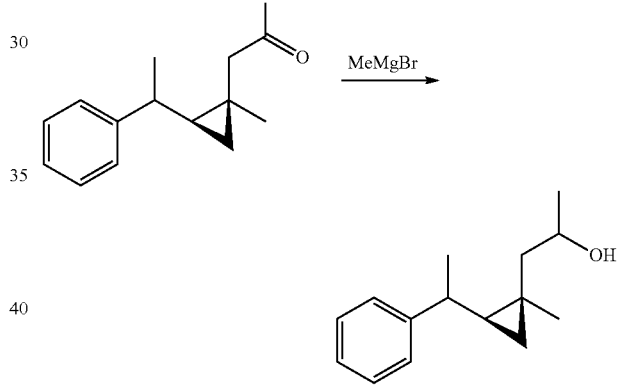

In a nitrogen atmosphere, methyl magnesium bromide (0.97 mol/L solution in tetrahydrofuran, 3.0 ml, 0.0029 mol) was placed in a 30 ml flask equipped with a stirrer, a dropping funnel, and a thermometer. 2-[(1R*,2S*)-1-Methyl-2-(1-phenylethyl)cyclopropyl]acetaldehyde (a mixture of two diastereomers at a component ratio of 1:2, 0.20 g, 0.00099 mol) and tetrahydrofuran (1 ml) were placed in the dropping funnel, and added dropwise in 5 minutes with the temperature being kept at 20° C. This mixture was stirred at the same temperature for 30 minutes. Next, a 5% aqueous sulfuric acid solution (2.9 g) was added, followed by stirring for 10 minutes. Then, the aqueous layer was separated. The organic layer was washed with water (2 ml) twice, and the solvent was recovered under reduced pressure to obtain a concentrated residue. The results of a GC analysis showed that the concentrated residue was a mixture of four isomers. This concentrated residue was purified by silica gel column chromatography (hexane:ethyl acetate=8:2), and the component with the longest retention time in the GC analysis was obtained (0.016 g, 0.00007 mol, yield: 7%). The concentrated residue was subjected to gas chromatography-olfactometry. The results showed that the obtained component had the lowest threshold among the four components.

GC/MS (m/e):

218 (M+, <1), 200(1), 185(3), 171(4), 157(8), 143(16), 131(13), 118(100), 117(50), 105(90), 91(35), 77(14), 69(18)

$^1$H (500 MHz, CDCl$_3$):

7.29 (ddm, J=7.5, 7.2, 2H), 7.25 (dm, J=7.5, 2H), 7.19 (tm, J=7.2, 1H), 4.09 (m, 1H), 2.29 (dq, J=10.5, 6.9, 1H), 2.03 (ddd, J=13.6, 5.9, 1.3, 1H), 1.42 (br. s, OH), 1.33 (d, J=6.9, 3H), 1.28 (d, 6.2, 3H), 1.27 (dd, J=13.6, 7.7, 1H), 1.11 (s, 3H), 0.71 (ddd, J=10.5, 8.6, 5.8, 1H), 0.44 (ddd, J=8.6, 4.7, 1.3, 1H), 0.01 (dd, J=5.8, 4.7, 1H)

$^{13}$C (125 MHz, CDCl$_3$)

147.6 (s), 128.3 (d), 127.0 (d), 125.8 (d), 67.6 (d), 42.7 (t), 40.0 (d), 32.9 (d), 25.7 (q), 23.5 (q), 22.5 (q), 18.95 (s), 18.90 (t)

Synthesis Example 15

Synthesis of 2-[(1S*,2S*)-1-Methyl-2-((R*)1-phenylethyl)cyclopropyl]ethanol

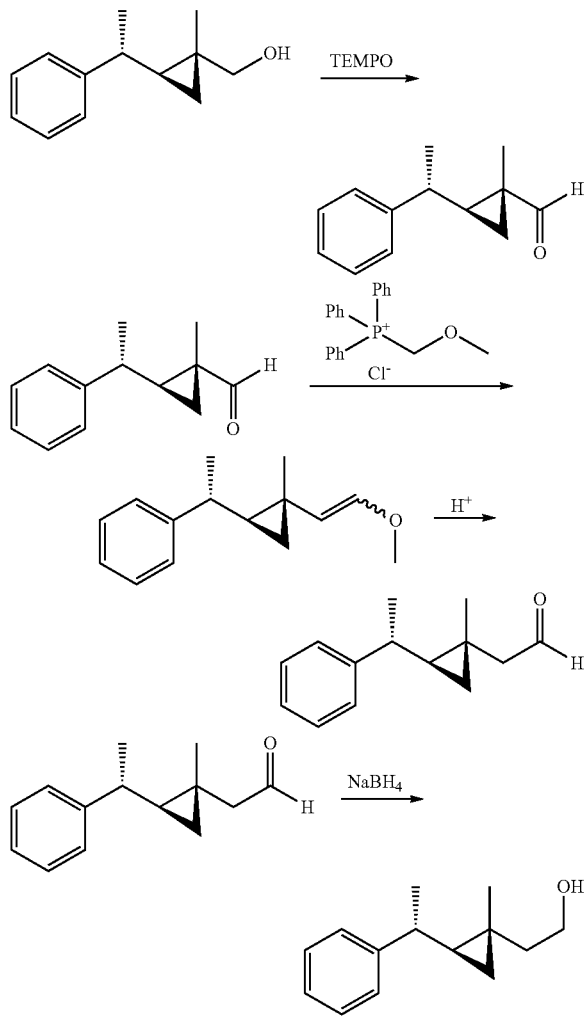

(1R*,2S*)-1-Methyl-2-[(R*)-1-phenylethyl]cyclopropanecarbaldehyde was obtained by conducting the same method as in Example 3, while the raw material in the method of Synthesis Example 3 was changed to 2-[(1R*, 2S*)-1-methyl-2-((R*)1-phenylethyl)cyclopropyl]methanol (2.04 g, 0.0107 mol). Then, 2-[(1S*,2S*)-1-methyl-2-((R*) 1-phenylethyl)cyclopropyl]acetaldehyde (1.26 g, 0.0062 mol) was obtained by the same method as in Example 12. Further, 2-[(1S*,2S*)-1-methyl-2-((R*)1-phenylethyl)cyclopropyl]ethanol (1.21 g, 0.0059 mol) was obtained by the same method as in Synthesis Example 13. The total yield was 55%.

GC/MS (m/e):

204 (M+, <1), 189(<1), 171(1), 159(8), 143(7), 131(22), 118(100), 117(52), 105(87), 91(28), 77(15), $^1$H (500 MHz, CDCl$_3$):

7.30 (ddm, J=8.3, 7.1, 2H), 7.26 (dm, J=8.3, 2H), 7.19 (tm, J=7.1, 1H), 3.80 (m, 2H), 2.28 (dq, J=10.7.0, 1H), 1.68 (ddd, J=13.8, 7.6, 6.5, 1H), 1.42 (ddd, J=, 13.8, 7.7, 6.7, 1H), 1.34 (d, J=7.0, 3H), 1.27 (m, OH), 1.20 (s, 3H), 0.78 (ddd, J=10.6, 8.7, 5.7, 1H), 0.45 (dd, J=8.7, 4.7, 1H), 0.06 (dd, J=5.7, 4.7, 1H)

$^{13}$C (125 MHz, CDCl$_3$)

147.4 (s), 128.3 (d), 126.9 (d), 125.9 (d), 61.4 (t), 44.2 (t), 40.1 (d), 31.4 (d), 22.6 (q), 19.0 (t), 18.1 (s), 17.5 (q)

Synthesis Example 16

Synthesis of [(1R*,2S*)-1-Methyl-2-((S*)-1-phenylethyl)cyclopropyl)]methyl Propionate

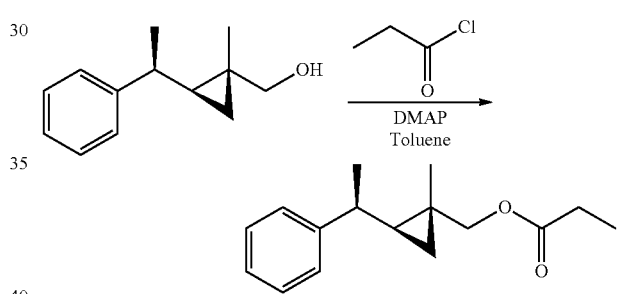

In a nitrogen atmosphere, 5 ml of anhydrous toluene, dimethylaminopyridine (154 mg, 1.26 mmol), and [(1R*, 2S*)-1-methyl-2-((S*)-1-phenylethyl)cyclopropyl)]methanol (200 mg, 1.05 mmol) were placed in a 30 ml flask equipped with a stirrer, a dropping funnel, and a thermometer, and stirred until dissolution. Then, propanoyl chloride (93 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9: 1) gave [(1R*,2S*)-1-methyl-2-((S*)-1-phenylethyl)cyclopropyl)]methyl propionate (243 g, 0.99 mmol, yield: 94%).

GC/MS (m/e): 246 (M+, 2%), 172(38), 157(77), 143(50), 129(38), 118(100), 117(100), 115(50), 105(100), 91(62), 77(35), 57(100)

$^1$H NMR (500 MHz, CDCl$_3$) δ 0.21 (dd, J=5.7 Hz, 4.8 Hz, 1H), 0.77 (dd, J=8.9 Hz, 4.8 Hz, 1H), 1.01 (s, 3H), 1.08 (t, J=7.6 Hz, 3H), 1.08 (m, 1H), 1.36 (d, J=7.0 Hz, 3H), 2.24 (dq, J=2.6 Hz, 7.6 Hz, 2H), 2.33 (m, 1H), 3.80 (d, J=11.1 Hz, 1H), 3.86 (d, J=11.1 Hz, 1H), 7.17 (m, 1H), 7.26 (m, 4H)

$^{13}$C NMR (125 MHz, CDCl$_3$) δ 174.6 (s), 147.3 (s), 128.2 (d), 126.7 (d), 125.7 (d), 73.1 (t), 40.1 (d), 29.0 (d), 27.6 (t), 23.4 (q), 20.4 (s), 17.0 (t), 16.1 (q), 9.1 (q)

Synthesis Example 17

Synthesis of [(1R*,2S*)-1-Methyl-2-((R*)-1-phenylethyl)cyclopropyl)]methyl Propionate

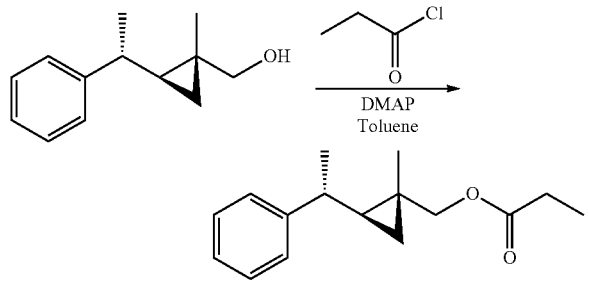

In a nitrogen atmosphere, 5 ml of anhydrous toluene, dimethylaminopyridine (154 mg, 1.26 mmol), and [(1R*,2S*)-1-methyl-2-((R*)-1-phenylethyl)cyclopropyl)]methanol (200 mg, 1.05 mmol) were placed in a 30 ml flask equipped with a stirrer, a dropping funnel, and a thermometer, and stirred until dissolution. Then, propanoyl chloride (93 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((R*)-1-phenylethyl)cyclopropyl)]methyl propionate (241 g, 0.98 mmol, yield: 93%).

GC/MS (m/e): 246 (M$^+$, <1%), 172(21), 157(42), 143 (28), 129(18), 118(100), 117(64), 105(75), 91(32), 77(15), 57(69)

$^1$H NMR (500 MHz, CDCl$_3$) δ 0.16 (dd, J=6.0 Hz, 5.0 Hz, 1H), 0.60 (dd, J=8.8 Hz, 5.0 Hz, 1H), 0.95 (ddd, J=10.6 Hz, 8.8 Hz, 6.0 Hz, 1H), 1.17 (t, J=7.6 Hz, 3H), 1.26 (s, 3H), 1.32 (d, J=6.9 Hz, 3H), 2.30 (dq, J=10.6 Hz, 6.9 Hz, 1H), 2.37 (q, J=7.6 Hz, 2H), 3.85 (d, J=11.1 Hz, 1H), 3.92 (d, J=11.1 Hz, 1H), 7.20 (tm, J=7.2 Hz, 1H), 7.26 (dm, J=7.2 Hz, 2H), 7.30 (t, J=7.2 Hz, 2H)

$^{13}$C NMR (125 MHz, CDCl$_3$) δ 174.7 (s), 147.0 (s), 128.3 (d), 126.9 (d), 126.0 (d), 73.3 (t), 39.8 (d), 30.0 (d), 27.7 (t), 22.4 (q), 20.4 (s), 17.1 (t), 15.8 (q), 9.3 (q)

Synthesis Example 18

Synthesis of [(1R*,2S*)-1-Methyl-2-((S*)-1-phenylethyl)cyclopropyl)]methyl Isobutanoate

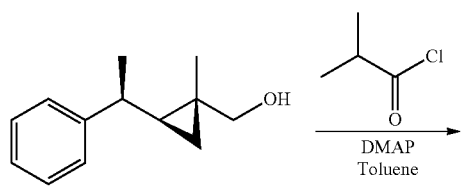

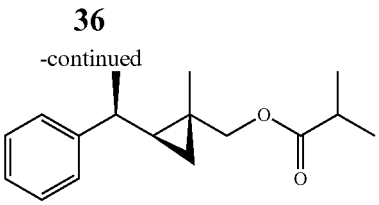

In a nitrogen atmosphere, 5 ml of anhydrous toluene, dimethylaminopyridine (154 mg, 1.26 mmol), and [(1R*,2S*)-1-methyl-2-((S*)-1-phenylethyl)cyclopropyl)]methanol (200 mg, 1.05 mmol) were placed in a 30 ml flask equipped with a stirrer, a dropping funnel, and a thermometer, and stirred until dissolution. Then, 2-methylpropanoyl chloride (134 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((S*)-1-phenylethyl)cyclopropyl)]methyl isobutanoate (257 mg, 0.99 mmol, yield: 94%).

GC/MS (m/e): 260 (M$^+$, 1%), 190(1), 172(16), 157(36), 143(20), 129(9), 118(100), 105(52), 91(14), 71(64), 43(27).

$^1$H NMR (500 MHz, CDCl$_3$) δ 0.21 (dd, 1H, J=5.2 Hz, 5.2 Hz), 0.75 (dd, 1H, J=4.8 Hz, 8.9 Hz), 1.02 (s, 3H), 1.04-1.11 (m, 1H), 1.08 (dd, 6H, J=7.0 Hz, 0.8 Hz), 1.35 (d, 3H, J=7.0 Hz), 2.28-2.37 (m, 1H), 2.46 (hept, 1H, J=7.0 Hz), 3.72 (d, 1H, J=11.1 Hz), 3.92 (d, 1H, J=11.1 Hz), 7.14-7.20 (m, 1H), 7.25-7.30 (m, 4H).

$^{13}$C NMR (CDCl$_3$, 125 MHz) δ 177.2 (s), 147.3 (s), 128.2 (d), 126.8 (d), 125.7 (d), 73.1 (t), 40.1 (d), 34.1 (d), 29.2 (d), 23.5 (q), 20.4 (s), 18.9 (q), 16.9 (t), 16.0 (q).

Synthesis Example 19

Synthesis of [(1R*,2S*)-1-Methyl-2-((R*)-1-phenylethyl)cyclopropyl)]methyl Isobutanoate

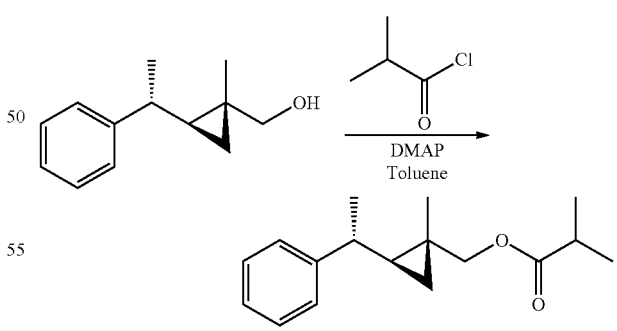

In a nitrogen atmosphere, 5 ml of anhydrous toluene, dimethylaminopyridine (154 mg, 1.26 mmol), and [(1R*,2S*)-1-methyl-2-((R*)-1-phenylethyl)cyclopropyl)]methanol (200 mg, 1.05 mmol) were placed in a 30 ml flask equipped with a stirrer, a dropping funnel, and a thermometer, and stirred until dissolution. Then, 2-methylpropanoyl chloride (134 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((R*)-1-phenylethyl)cyclopropyl)]methyl isobutanoate (255 mg, 0.98 mmol, yield: 93%). 129(8), 118(100), 105(53), 91(15), 71(59), 43(25).

$^1$H NMR (500 MHz, CDCl$_3$) δ 0.15 (dd, 1H, J=5.5 Hz, 5.5 Hz), 0.60 (dd, 1H, J=8.8 Hz, 5.0 Hz), 0.93-1.00 (m, 1H), 1.20 (dd, 6H, J=7.0 Hz, 3.5 Hz), 1.26 (s, 3H), 1.33 (d, 3H, J=6.9 Hz), 2.25-2.33 (m, 1H), 2.59 (quin, 1H, J=7.0 Hz), 3.79 (d, 1H, J=11.1 Hz), 3.96 (d, 1H, J=11.1 Hz), 7.17-7.22 (m, 1H), 7.24-7.33 (m, 4H).

$^{13}$C NMR (CDCl$_3$, 125 MHz) δ 177.2 (s), 147.0 (s), 128.3 (d), 126.9 (d), 126.0 (d), 73.2 (t), 39.8 (d), 34.2 (d), 30.1 (d), 22.5 (q), 20.5 (s), 19.1 (q), 19.0 (q), 17.0 (t), 15.8 (d).

Synthesis Example 20

Synthesis of [(1R*,2S*)-1-Methyl-2-((S*)-1-phenylethyl)cyclopropyl)]methyl Cyclopropanecarboxylate

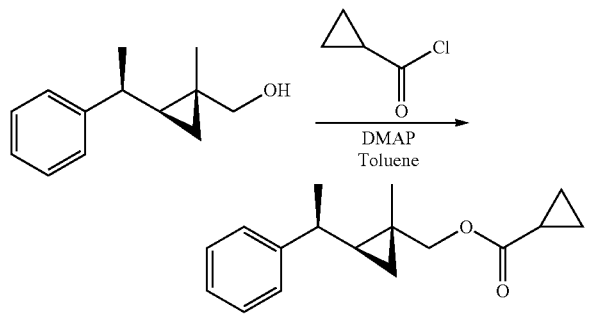

In a nitrogen atmosphere, 5 ml of anhydrous toluene, dimethylaminopyridine (154 mg, 1.26 mmol), and [(1R*,2S*)-1-methyl-2-((S*)-1-phenylethyl)cyclopropyl)]methanol (200 mg, 1.05 mmol) were placed in a 30 ml flask equipped with a stirrer, a dropping funnel, and a thermometer, and stirred until dissolution. Then, cyclopropanecarbonyl chloride (132 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((S*)-1-phenylethyl)cyclopropyl)]methyl cyclopropanecarboxylate (250 mg, 0.97 mmol, yield: 92%).

GC/MS (m/e): 258 (M$^+$, 0.2%), 188(2), 172(14), 157(32), 143(18), 129(8), 118(92), 105(42), 91(13), 77(8), 69(100), 55(3), 41(16);

$^1$H NMR (500 MHz, CDCl$_3$) δ 0.22 (dd, 1H, J=5.2 Hz, 5.2 Hz), 0.77 (dd, 1H, J=4.8 Hz, 8.9 Hz), 0.76-0.84 (m, 2H), 0.87-0.95 (m, 2H), 1.02 (s, 3H), 1.03-1.10 (m, 1H), 1.35 (d, 3H, J=7.0 Hz), 1.51-1.56 (m, 1H), 2.27-2.38 (m, 1H), 3.77 (d, 1H, J=11.1 Hz), 3.86 (d, 1H, J=11.1 Hz), 7.15-7.20 (m, 1H), 7.24-7.31 (m, 4H).

$^{13}$C NMR (CDCl$_3$, 125 MHz) δ 175.0 (s), 147.3 (s), 128.2 (d), 126.7 (d), 125.7 (d), 73.2 (t), 40.1 (d), 28.9 (d), 23.5 (q), 20.3 (s), 17.0 (t), 16.1 (q), 13.0 (d), 8.2 (t).

Synthesis Example 21

Synthesis of [(1R*,2S*)-1-Methyl-2-((R*)-1-phenylethyl)cyclopropyl)]methyl Cyclopropanecarboxylate

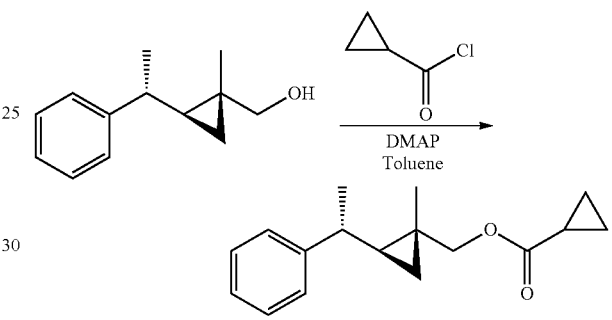

In a nitrogen atmosphere, 5 ml of anhydrous toluene, dimethylaminopyridine (154 mg, 1.26 mmol), and [(1R*,2S*)-1-methyl-2-((R*)-1-phenylethyl)cyclopropyl)]methanol (200 mg, 1.05 mmol) were placed in a 30 ml flask equipped with a stirrer, a dropping funnel, and a thermometer, and stirred until dissolution. Then, cyclopropanecarbonyl chloride (132 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((R*)-1-phenylethyl)cyclopropyl)]methyl cyclopropanecarboxylate (250 mg, 0.97 mmol, yield: 92%).

GC/MS (m/e): 258 (M$^+$, 0.2%), 188(2), 172(13), 157(32), 143(19), 129(8), 118(92), 105(44), 91(14), 77(8), 69(100), 55(3), 41(15);

$^1$H NMR (500 MHz, CDCl$_3$) δ 0.16 (dd, 1H, J=5.5 Hz, 5.5 Hz), 0.60 (dd, 1H, J=8.8 Hz, 5.0 Hz), 0.84-0.89 (m, 2H), 0.92-0.99 (m, 1H), 0.99-1.04 (m, 2H), 1.26 (s, 3H), 1.33 (d, 3H, J=7.0 Hz), 1.61-1.68 (m, 1H), 2.26-2.34 (m, 1H), 3.83 (d, 1H, J=11.1 Hz), 3.92 (d, 1H, J=11.1 Hz), 7.18-7.22 (m, 1H), 7.24-7.33 (m, 4H).

$^{13}$C NMR (CDCl$_3$, 125 MHz) δ 175.0 (s), 147.0 (s), 128.3 (d), 126.9 (d), 126.0 (d), 73.4 (t), 39.8 (d), 30.0 (d), 22.5 (q), 20.4 (s), 17.0 (t), 15.8 (q), 13.0 (d), 8.3 (t).

Synthesis Example 22

Synthesis of [(1R*,2S*)-1-Methyl-2-((S*)-1-phenyl-ethyl)cyclopropyl)]methyl Cyclobutanecarboxylate

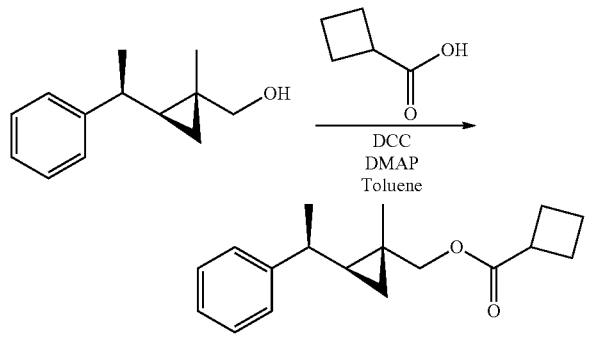

In a nitrogen atmosphere, 5 ml of anhydrous toluene, dimethylaminopyridine (154 mg, 1.26 mmol), dicyclohexylcarbodiimide (260 mg, 1.26 mmol), [(1R*,2S*)-1-methyl-2-((S*)-1-phenylethyl)cyclopropyl]methanol (200 mg, 1.05 mmol), and cyclobutanecarboxylic acid (126 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*, 2S*)-1-methyl-2-((S*)-1-phenylethyl)cyclopropyl)]methyl cyclobutanecarboxylate (250 mg, 0.97 mmol, yield: 92%).

GC/MS (m/e): 272 (M+, 0.4%), 202(2), 188(1), 172(15), 157(35), 143(18), 129(8), 118(100), 105(45), 91(13), 83(47), 69(4), 55(41), 29(7);

$^1$H NMR (500 MHz, CDCl$_3$) δ 0.21 (dd, 1H, J=5.2 Hz, 5.2 Hz), 0.76 (dd, 1H, J=4.8 Hz, 8.9 Hz), 1.02 (s, 3H), 1.04-1.12 (m, 1H), 1.34 (d, 3H, J=7.0 Hz), 1.79-1.89 (m, 1H), 1.89-1.98 (m, 1H), 2.06-2.23 (m, 4H), 2.28-2.36 (m, 1H), 3.05 (quint d, 1H, J=8.6 Hz, J=0.9 Hz), 3.75 (d, 1H, J=11.1 Hz), 3.90 (d, 1H, J=11.1 Hz), 7.15-7.19 (m, 1H), 7.24-7.30 (m, 4H).

$^{13}$C NMR (CDCl$_3$, 125 MHz) δ 177.6 (s), 147.3 (s), 128.2 (d), 126.7 (d), 125.7 (d), 73.0 (t), 40.1 (d), 38.2 (d), 29.1 (d), 25.23 (t), 25.19 (t), 23.4 (q), 20.4 (s), 18.4 (t), 16.9 (t), 16.0 (q).

Synthesis Example 23

Synthesis of [(1R*,2S*)-1-Methyl-2-((R*)-1-phenyl-ethyl)cyclopropyl)]methyl Cyclobutanecarboxylate

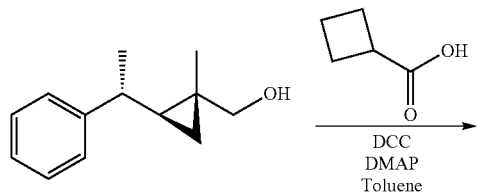

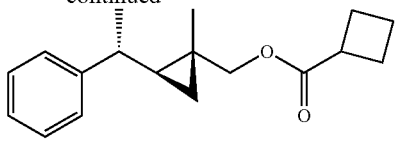

In a nitrogen atmosphere, 5 ml of anhydrous toluene, dimethylaminopyridine (154 mg, 1.26 mmol), dicyclohexylcarbodiimide (260 mg, 1.26 mmol), (1R*,2S*)-1-methyl-2-((R*)-1-phenylethyl)cyclopropyl)methanol (200 mg, 1.05 mmol), and cyclobutanecarboxylic acid (126 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave (1R*, 2S*)-1-methyl-2-((R*)-1-phenylethyl)cyclopropyl)methyl cyclobutylcarboxylate (250 mg, 0.97 mmol, yield: 92%).

GC/MS (m/e): 272 (M+, 0.3%), 202(2), 172(13), 157(34), 143(19), 129(7), 118(100), 105(46), 91(13), 83(44), 69(4), 55(40), 29(7);

$^1$H NMR (500 MHz, CDCl$_3$) δ 0.15 (dd, 1H, J=5.5 Hz, 5.5 Hz), 0.60 (dd, 1H, J=8.8 Hz, 5.0 Hz), 0.92-0.99 (m, 1H), 1.25 (s, 3H), 1.32 (d, 3H, J=7.0 Hz), 1.88-1.97 (m, 1H), 1.93-2.04 (m, 1H), 2.18-2.37 (m, 5H), 3.17 (quint d, 1H, J=8.5 Hz, J=0.9 Hz), 3.83 (d, 1H, J=11.1 Hz), 3.94 (d, 1H, J=11.1 Hz), 7.17-7.22 (m, 1H), 7.24-7.33 (m, 4H).

$^{13}$C NMR (CDCl$_3$, 125 MHz) δ 175.6 (s), 147.0 (s), 128.3 (d), 126.9 (d), 126.0 (d), 73.1 (t), 39.8 (d), 38.3 (d), 30.0 (d), 25.4 (t), 25.3 (t), 22.4 (q), 20.5 (s), 18.5 (t), 17.0 (t), 15.8 (q).

Synthesis Example 24

Synthesis of [(1S*,2R*)-1-Methyl-2-((R*)-5-meth-ylhex-4-en-2-yl)cyclopropyl)]methyl Propionate

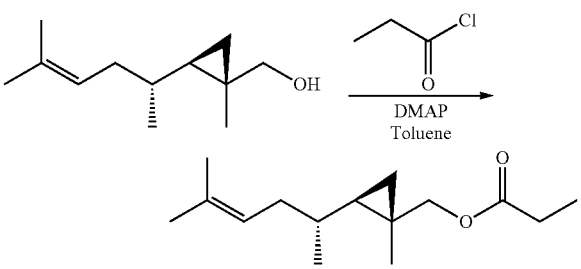

In a nitrogen atmosphere, 5 ml of anhydrous toluene, dimethylaminopyridine (154 mg, 1.26 mmol), and [(1S*, 2R*)-1-methyl-2-((R*)-5-methylhex-4-en-2-yl)cyclopropyl)]methanol (191 mg, 1.05 mmol) (synthesized by the method described in International Patent Application Publication No. WO2012/160189) were placed in a 30 ml flask equipped with a stirrer, a dropping funnel, and a thermometer, and stirred until dissolution. Then, propanoyl chloride (117 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1S*,2R*)-1-methyl-2-((R*)-5-methylhex-4-en-2-yl)cyclopropyl)]methyl propionate (236 mg, 0.99 mmol, yield: 94%).

GC/MS (m/e): 238 (M+, undetected), 182(1), 169(1), 164(8), 149(6), 135(1), 121(24), 109(5), 107(4), 95(73), 81(8), 69(15), 67(13), 57(100), 55(14), 41(19), 29(24);

$^1$H NMR (CDCl$_3$, 500 MHz) δ 0.10 (dd, 1H, J=5.2 Hz, 5.2 Hz), 0.47-0.54 (m, 1H), 0.60 (dd, 1H, J=8.8 Hz, J=4.7 Hz), 0.93 (d, 3H, J=6.6 Hz), 1.00-1.08 (m, 1H), 1.12 (s, 3H), 1.15 (t, 3H, J=7.6 Hz), 1.60 (s, 3H), 1.70 (d, 3H, J=1.0 Hz), 1.91-2.00 (m, 1H), 2.07-2.15 (m, 1H), 2.35 (q, 2H, J=7.6 Hz), 3.79 (d, 1H, J=11.1 Hz), 3.85 (d, 1H, J=11.1 Hz), 5.13-5.20 (m, 4H).

$^{13}$C NMR (CDCl$_3$, 125 MHz) δ 174.7 (s), 132.0 (s), 123.0 (d), 73.6 (t), 35.5 (t), 34.6 (d), 29.4 (d), 27.1 (t), 25.8 (q), 20.1 (q), 19.1 (s), 17.7 (q), 16.8 (t), 15.7 (q), 9.2 (q).

Synthesis Example 25

Synthesis of [(1S*,2R*)-1-Methyl-2-((S*)-5-methylhex-4-en-2-yl)cyclopropyl)]methyl Propionate

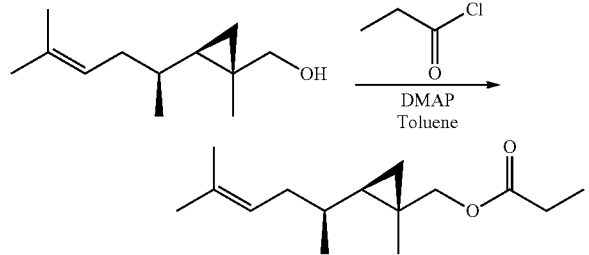

In a nitrogen atmosphere, 5 ml of anhydrous toluene, dimethylaminopyridine (154 mg, 1.26 mmol), and [(1S*,2R*)-1-methyl-2-((S*)-5-methylhex-4-en-2-yl)cyclopropyl)]methanol (191 mg, 1.05 mmol) (synthesized by the method described in International Patent Application Publication No. WO2012/160189) were placed in a 30 ml flask equipped with a stirrer, a dropping funnel, and a thermometer, and stirred until dissolution. Then, propanoyl chloride (117 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1S*,2R*)-1-methyl-2-((S*)-5-methylhex-4-en-2-yl)cyclopropyl)]methyl propionate (232 mg, 0.97 mmol, yield: 92%).

GC/MS (m/e): 238 (M+, 0.1), 182(1), 169(5), 164(13), 149(6), 135(2), 121(21), 109(12), 95(100), 81(10), 79(6), 69(24), 67(24), 57(82), 41(17), 29(28);

$^1$H NMR (CDCl$_3$, 500 MHz) δ 0.01 (dd, 1H, J=5.5 Hz, 4.5 Hz), 0.48-0.55 (m, 1H), 0.58 (dd, 1H, J=9.0 Hz, J=4.5 Hz), 0.96 (d, 3H, J=6.6 Hz), 1.03-1.10 (m, 1H), 1.12 (s, 3H), 1.15 (t, 3H, J=7.6 Hz), 1.60 (s, 3H), 1.71 (d, 3H, J=0.9 Hz), 1.89-1.98 (m, 1H), 2.01-2.09 (m, 1H), 2.35 (q, 2H, J=7.6 Hz), 3.81 (s, 2H), 5.14-5.21 (m, 4H).

$^{13}$C NMR (CDCl$_3$, 500 MHz) δ 174.7 (s), 131.8 (s), 123.0 (d), 73.5 (t), 35.7 (t), 34.2 (d), 29.5 (d), 27.7 (t), 25.8 (q), 20.0 (s), 19.9 (q), 17.7 (q), 16.2 (d), 16.1 (t), 9.2 (q).

Synthesis Example 26

Synthesis of [(1R*,2S*)-1-Methyl-2-((S*)-1-phenylethyl)cyclopropyl)]methyl Acrylate

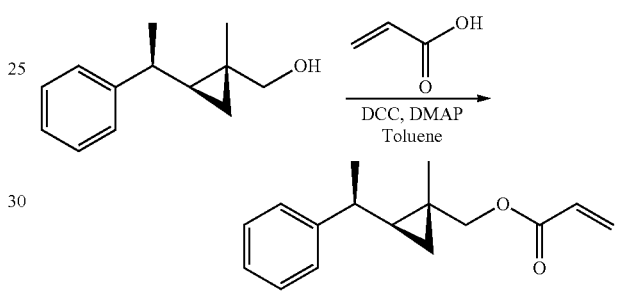

In a nitrogen atmosphere, 5 ml of anhydrous toluene, dimethylaminopyridine (154 mg, 1.26 mmol), dicyclohexylcarbodiimide (260 mg, 1.26 mmol), [(1R*,2S*)-1-methyl-2-((S*)-1-phenylethyl)cyclopropyl)]methanol (200 mg, 1.05 mmol), and acrylic acid (91 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((S*)-1-phenylethyl)cyclopropyl)]methyl acrylate (242 mg, 0.99 mmol, yield: 94%).

GC/MS (m/e): 244 (M+, 0.3%), 189(1), 172(16), 157(29), 143(16), 129(9), 118(100), 105(59), 91(16), 77(11), 65(4), 55(46), 39(4), 27(13);

$^1$H NMR (CDCl$_3$, 500 MHz) δ 0.24 (dd, 1H, J=5.3 Hz, 5.3 Hz), 0.80 (dd, 1H, J=8.9 Hz, 4.8 Hz), 1.03 (s, 3H), 1.06-1.13 (m, 1H), 1.35 (d, 3H, J=7.0 Hz), 2.30-2.38 (m, 1H), 3.85 (d, 1H, J=11.1 Hz), 3.98 (d, 1H, J=11.1 Hz), 5.78 (dd, 1H, J=10.4 Hz, 1.5 Hz), 6.05 (dd, 1H, J=17.4 Hz, 10.4 Hz), 6.28 (dd, 1H, J=17.4 Hz, 1.45 Hz), 7.14-7.19 (m, 1H), 7.24-7.28 (m, 4H).

$^{13}$C NMR (CDCl$_3$, 125 MHz) δ 166.3 (s), 147.3 (s), 130.4 (t), 128.6 (d), 128.2 (d), 126.7 (d), 125.7 (d), 73.4 (t), 40.1 (d), 29.0 (d), 23.5 (q), 20.3 (s), 17.1 (t), 16.1 (q).

Synthesis Example 27

Synthesis of [(1R*,2S*)-1-Methyl-2-((R*)-1-phenylethyl)cyclopropyl)]methyl Acrylate

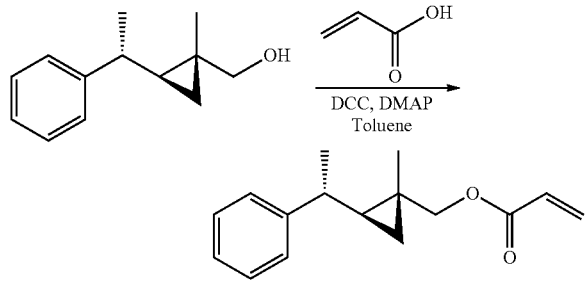

In a nitrogen atmosphere, 5 ml of anhydrous toluene, dimethylaminopyridine (154 mg, 1.26 mmol), dicyclohexylcarbodiimide (260 mg, 1.26 mmol), [(1R*,2S*)-1-methyl-2-((R*)-1-phenylethyl)cyclopropyl)]methanol (200 mg, 1.05 mmol), and acrylic acid (91 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((R*)-1-phenylethyl)cyclopropyl)]methyl acrylate (238 mg, 0.97 mmol, yield: 93%).

GC/MS (m/e): 244 (M+, 0.2%), 189(1), 172(16), 157(26), 143(15), 129(9), 118(100), 105(59), 91(17), 77(11), 65(4), 55(42), 39(4), 27(12);

$^1$H NMR (CDCl$_3$, 500 MHz) δ 0.18 (dd, 1H, J=5.5 Hz, 5.5 Hz), 0.63 (dd, 1H, J=8.9 Hz, 5.1 Hz), 0.94-1.02 (m, 1H), 1.28 (s, 3H), 1.33 (d, 3H, J=6.9 Hz), 2.26-2.35 (m, 1H), 3.91 (d, 1H, J=11.2 Hz), 4.03 (d, 1H, J=11.2 Hz), 5.84 (dd, 1H, J=10.4 Hz, 1.5 Hz), 6.17 (dd, 1H, J=17.3 Hz, 10.5 Hz), 6.43 (dd, 1H, J=17.3 Hz, 1.5 Hz), 7.17-7.23 (m, 1H), 7.24-7.33 (m, 4H).

$^{13}$C NMR (CDCl$_3$, 125 MHz) δ 166.4 (s), 147.0 (s), 130.5 (t), 128.7 (d), 128.3 (d), 126.9 (d), 126.0 (d), 73.5 (t), 39.8 (d), 30.1 (d), 22.4 (q), 20.4 (s), 17.11 (t), 15.80 (q).

Synthesis Example 28

Synthesis of [(1R*,2S*)-1-Methyl-2-((S*)-1-phenylethyl)cyclopropyl)]methyl Methacrylate

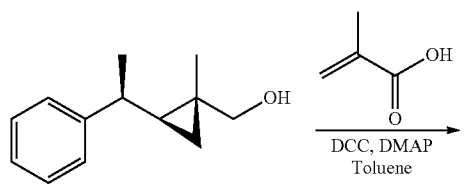

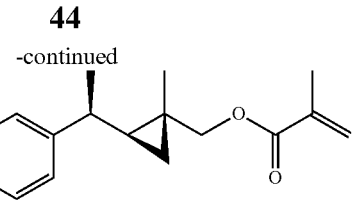

In a nitrogen atmosphere, 5 ml of anhydrous toluene, dimethylaminopyridine (154 mg, 1.26 mmol), dicyclohexylcarbodiimide (260 mg, 1.26 mmol), [(1R*,2S*)-1-methyl-2-((S*)-1-phenylethyl)cyclopropyl)]methanol (200 mg, 1.05 mmol), and methacrylic acid (108 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-1-methyl-2-((S*)-1-phenylethyl)cyclopropyl)]methyl methacrylate (254 mg, 0.99 mmol, yield: 94%).

GC/MS (m/e): 258 (M+, 0.4%), 188(1), 172(15), 157(27), 143(14), 129(8), 118(100), 105(45), 91(14), 77(9), 69(68), 55(3), 41(23), 27(3);

$^1$H NMR (CDCl$_3$, 500 MHz) δ 0.23 (dd, 1H, J=5.3 Hz, 5.3 Hz), 0.78 (dd, 1H, J=8.9 Hz, 4.9 Hz), 1.05 (s, 3H), 1.06-1.13 (m, 1H), 1.35 (d, 3H, J=7.0 Hz), 1.86 (s, 3H), 2.30-2.38 (m, 1H), 3.74 (d, 1H, J=11.1 Hz), 4.04 (d, 1H, J=11.1 Hz), 5.49 (t, J=1.6 Hz), 5.97 (d, 1H, J=0.6 Hz), 7.14-7.19 (m, 1H), 7.24-7.28 (m, 4H).

$^{13}$C NMR (CDCl$_3$, 125 MHz) δ 167.6 (s), 147.3 (s), 136.4 (s), 128.2 (d), 126.7 (d), 125.7 (d), 125.2 (t), 73.6 (t), 40.2 (d), 29.2 (d), 23.4 (q), 20.3 (s), 18.2 (q), 16.9 (t), 16.1 (q).

Synthesis Example 29

Synthesis of [(1R*,2S*)-1-Methyl-2-((R*)-1-phenylethyl)cyclopropyl)]methyl Methacrylate

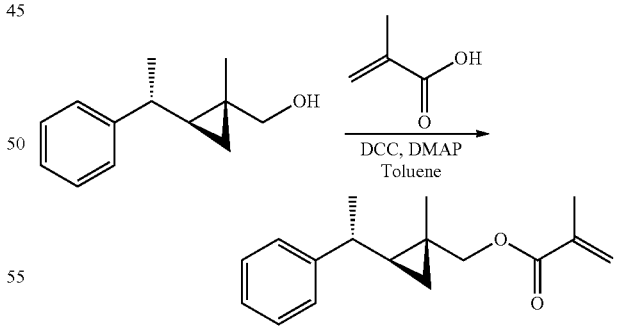

In a nitrogen atmosphere, 5 ml of anhydrous toluene, dimethylaminopyridine (154 mg, 1.26 mmol), dicyclohexylcarbodiimide (260 mg, 1.26 mmol), [(1R*,2S*)-1-methyl-2-((R*)-1-phenylethyl)cyclopropyl)]methanol (200 mg, 1.05 mmol), and methacrylic acid (108 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*, 2S*)-1-methyl-2-((R*)-1-phenylethyl)cyclopropyl)]methyl methacrylate (253 mg, 0.98 mmol, yield: 93%).

GC/MS (m/e): 258 (M+, 0.3%), 188(1), 172(14), 157(26), 143(15), 129(8), 118(100), 105(48), 91(15), 77(9), 69(67), 41(22);

$^1$H NMR (CDCl$_3$, 500 MHz) δ 0.18 (dd, 1H, J=5.5 Hz, 5.5 Hz), 0.63 (dd, 1H, J=8.8 Hz, 5.1 Hz), 0.94-1.02 (m, 1H), 1.29 (s, 3H), 1.34 (d, 3H, J=6.9 Hz), 1.98 (s, 3H), 2.26-2.35 (m, 1H), 3.81 (d, 1H, J=11.1 Hz), 4.08 (d, 1H, J=11.1 Hz), 5.57 (t, 1H, J=1.6 Hz), 6.15 (s, 1H), 7.17-7.23 (m, 1H), 7.24-7.33 (m, 4H).

$^{13}$C NMR (CDCl$_3$, 125 MHz) δ 167.6 (s), 147.0 (s), 136.6 (s), 128.3 (d), 126.9 (d), 126.0 (d), 125.2 (t), 73.8 (t), 39.8 (d), 30.0 (d), 22.4 (q), 20.4 (s), 18.3 (q), 17.0 (t), 15.9 (q).

Synthesis Example 30

Synthesis of [(1S*,2R*)-1-Methyl-2-((S*)-5-methylhex-4-en-2-yl)cyclopropyl)]methyl Isobutyrate

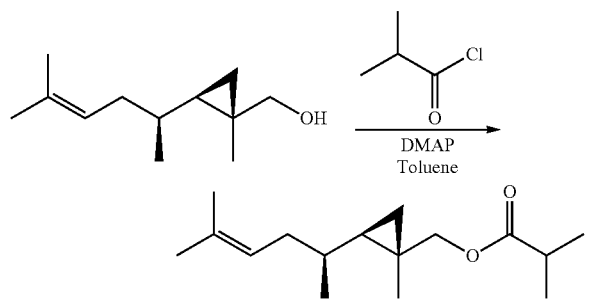

In a nitrogen atmosphere, 5 ml of anhydrous toluene, dimethylaminopyridine (154 mg, 1.26 mmol), and [(1S*, 2R*)-1-methyl-2-((S*)-5-methylhex-4-en-2-yl)cyclopropyl)]methanol (191 mg, 1.05 mmol) (synthesized by the method described in International Patent Application Publication No. WO2012/160189) were placed in a 30 ml flask equipped with a stirrer, a dropping funnel, and a thermometer, and stirred until dissolution. Then, isobutyryl chloride (134 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane: ethyl acetate=9:1) gave [(1S*,2R*)-1-methyl-2-((S*)-5-methylhex-4-en-2-yl)cyclopropyl)]methyl isobutyrate (244 mg, 0.97 mmol, yield: 92%).

GC/MS (m/e): 252 (M+, 0.1%), 183(5), 164(8), 149(4), 135(1), 121(18), 109(12), 95(100), 81(8), 71(60), 55(15), 43(60), 27(4).

$^1$H NMR (CDCl$_3$, 500 MHz) δ -0.01-0.03 (m, 1H), 0.49-0.56 (m, 1H), 0.58 (dd, 1H, J=9.0 Hz, 4.3 Hz), 0.96 (d, 3H, J=6.6 Hz), 1.02-1.10 (m, 1H), 1.13 (s, 3H), 1.18 (dd, 6H, J=7.0 Hz, J=1.7H), 1.60 (s, 3H), 1.71 (d, 3H, J=0.9 Hz), 1.87-1.97 (m, 1H), 2.03-2.11 (m, 1H), 2.57 (h, 1H, J=7.0 Hz), 3.77 (d, 1H, J=11.0 Hz), 3.84 (d, 1H, J=11.0 Hz), 5.14-5.21 (m, 1H).

$^{13}$C NMR (CDCl$_3$, 125 MHz) δ 177.3 (s), 131.8 (s), 123.0 (d), 73.3 (t), 35.7 (t), 34.24 (d), 34.15 (d), 29.6 (d), 25.8 (q), 20.0 (s), 19.9 (q), 19.0 (q), 17.7 (q), 16.1 (q), 16.0 (t).

Synthesis Example 31

Synthesis of [(1S*,2R*)-1-Methyl-2-((R*)-5-methylhex-4-en-2-yl)cyclopropyl)]methyl Isobutyrate

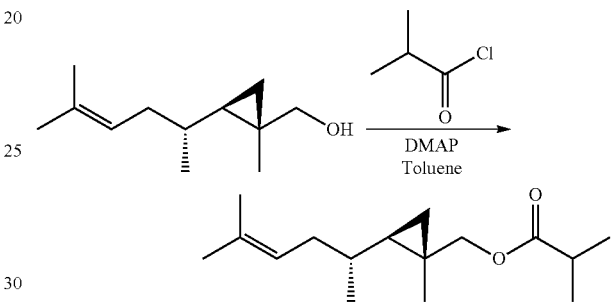

In a nitrogen atmosphere, 5 ml of anhydrous toluene, dimethylaminopyridine (154 mg, 1.26 mmol), and [(1S*, 2R*)-1-methyl-2-((R*)-5-methylhex-4-en-2-yl)cyclopropyl)]methanol (191 mg, 1.05 mmol) (synthesized by the method described in International Patent Application Publication No. WO2012/160189) were placed in a 30 ml flask equipped with a stirrer, a dropping funnel, and a thermometer, and stirred until dissolution. Then, isobutyryl chloride (134 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane: ethyl acetate=9:1) gave [(1S*,2R*)-1-methyl-2-((R*)-5-methylhex-4-en-2-yl)cyclopropyl)]methyl isobutyrate (244 mg, 0.97 mmol, yield: 92%).

GC/MS (m/e): 252 (M+, 0.3%), 183(3), 169(1), 164(11), 149(8), 135(2), 121(34), 109(8), 107(6), 95(100), 81(10), 79(5), 71(84), 69(23), 67(16), 55(18), 43(76), 41(29), 29(5), 27(5).

$^1$H NMR (CDCl$_3$, 500 MHz) δ 0.09 (dd, 1H, J=5.2 Hz, J=5.2 Hz), 0.47-0.55 (m, 1H), 0.59 (dd, 1H, J=8.9 Hz, 4.7 Hz), 0.93 (d, 3H, J=6.6 Hz), 0.97-1.09 (m, 1H), 1.12 (s, 3H), 1.18 (dd, 6H, J=7.0 Hz, J=2.3H), 1.60 (s, 3H), 1.70 (d, 3H, J=0.9 Hz), 1.91-2.22 (m, 1H), 2.03-2.08 (m, 1H), 2.56 (h, 1H, J=7.0 Hz), 3.74 (d, 1H, J=11.0 Hz), 3.88 (d, 1H, J=11.0 Hz), 5.13-5.20 (m, 1H).

$^{13}$C NMR (CDCl$_3$, 125 MHz) δ 177.3 (s), 132.0 (s), 123.0 (d), 73.4 (t), 35.5 (t), 34.7 (d), 34.2 (d), 29.5 (d), 25.8 (q), 19.2 (s), 19.1 (q), 19.0 (q), 17.7 (q), 16.8 (t), 15.7 (q).

Synthesis Example 32

Synthesis of [(1S*,2R*)-1-Methyl-2-((S)-5-methylhex-4-en-2-yl)cyclopropyl)]methyl Cyclopropanecarboxylate

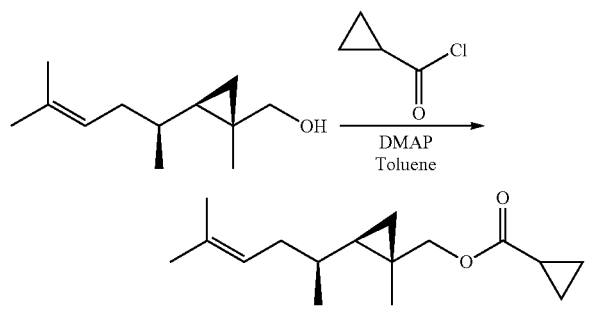

In a nitrogen atmosphere, 5 ml of anhydrous toluene, dimethylaminopyridine (154 mg, 1.26 mmol), and [(1S*,2R*)-1-methyl-2-((S*)-5-methylhex-4-en-2-yl)cyclopropyl)]methanol (191 mg, 1.05 mmol) (synthesized by the method described in International Patent Application Publication No. WO2012/160189) were placed in a 30 ml flask equipped with a stirrer, a dropping funnel, and a thermometer, and stirred until dissolution. Then, cyclopropanecarbonyl chloride (132 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1S*,2R*)-1-methyl-2-((S*)-5-methylhex-4-en-2-yl)cyclopropyl)]methyl cyclopropanecarboxylate (238 mg, 0.95 mmol, yield: 91%).

GC/MS (m/e): 250 (M$^+$, 0.04), 181(6), 164(8), 149(4), 135(1), 121(13), 109(10), 107(4), 95(63), 81(6), 79(4), 69(100), 55(8), 41(22), 29(4), 27(2);

$^1$H NMR (CDCl$_3$, 500 MHz) δ 0.01 (dd, 1H, J=4.7 Hz, 4.5 Hz), 0.48-0.56 (m, 1H), 0.58 (dd, 1H, J=9.0 Hz, 4.5 Hz), 0.82-0.87 (m, 2H), 0.97 (d, 3H, J=6.6 Hz), 0.98-1.02 (m, 2H), 1.02-1.11 (m, 1H), 1.13 (s, 3H), 1.61 (s, 3H), 1.60-1.66 (m, 1H), 1.71 (d, 3H, J=0.9 Hz), 1.90-1.98 (m, 1H), 2.01-2.09 (m, 1H), 3.79 (d, 1H, J=11.1 Hz), 3.82 (d, 1H, J=11.1 Hz), 5.15-5.22 (m, 1H).

$^{13}$C NMR (CDCl$_3$, 125 MHz) δ 175.1 (s), 131.8 (s), 123.0 (d), 73.6 (t), 35.7 (t), 34.2 (d), 29.6 (d), 25.8 (q), 20.0 (s), 19.9 (q), 17.8 (q) 16.2 (q), 16.1 (t), 13.0 (d), 8.3 (t).

Synthesis Example 33

Synthesis of [(1S*,2R*)-1-Methyl-2-((R*)-5-methylhex-4-en-2-yl)cyclopropyl)]methyl Cyclopropanecarboxylate

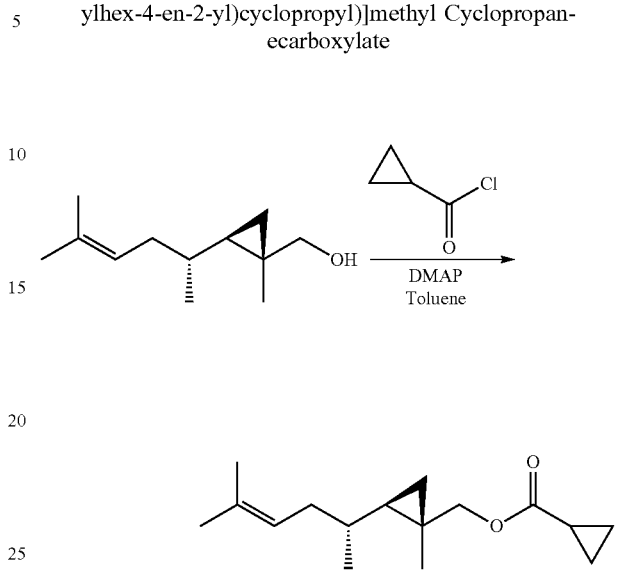

In a nitrogen atmosphere, 5 ml of anhydrous toluene, dimethylaminopyridine (154 mg, 1.26 mmol), and [(1S*,2R*)-1-methyl-2-((R*)-5-methylhex-4-en-2-yl)cyclopropyl)]methanol (191 mg, 1.05 mmol) (synthesized by the method described in International Patent Application Publication No. WO2012/160189) were placed in a 30 ml flask equipped with a stirrer, a dropping funnel, and a thermometer, and stirred until dissolution. Then, cyclopropanecarbonyl chloride (132 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1S*,2R*)-1-methyl-2-((R*)-5-methylhex-4-en-2-yl)cyclopropyl)]methyl cyclopropanecarboxylate (239 mg, 0.95 mmol, yield: 91%).

GC/MS (m/e): 250 (M+· 0.1), 181(3), 164(7), 149(6), 135(1), 121(24), 109(4), 107(4), 95(66), 81(6), 79(4), 69(100), 55(11), 41(32), 29(4), 27(2);

$^1$H NMR (CDCl$_3$, 500 MHz) δ 0.10 (dd, 1H, J=5.2 Hz, 5.2 Hz), 0.47-0.54 (m, 1H), 0.60 (dd, 1H, J=8.9 Hz, 4.7 Hz), 0.82-0.87 (m, 2H), 0.93 (d, 3H, J=6.5 Hz), 0.97-1.02 (m, 2H), 1.02-1.09 (m, 1H), 1.13 (s, 3H), 1.61 (s, 3H), 1.59-1.66 (m, 1H), 1.70 (d, 3H, J=0.9 Hz), 1.91-2.00 (m, 1H), 2.07-2.15 (m, 1H), 3.77 (d, 1H, J=11.0 Hz), 3.85 (d, 1H, J=11.0 Hz), 5.13-5.20 (m, 1H).

$^{13}$C NMR (CDCl$_3$, 125 MHz) δ 175.0 (s), 132.0 (s), 123.0 (d), 73.7 (t), 35.5 (t), 34.6 (d), 29.4 (d), 25.8 (q), 20.1 (q), 19.1 (s), 17.8 (q), 16.8 (t), 15.7 (q), 13.0 (d), 8.2 (t).

Synthesis Example 34

Synthesis of [(1S*,2R*)-1-Methyl-2-((S*)-5-methylhex-4-en-2-yl)cyclopropyl)]methyl Cyclobutanecarboxylate

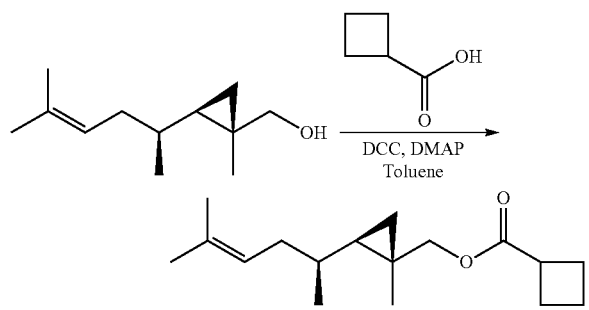

In a nitrogen atmosphere, 5 ml of anhydrous toluene, dimethylaminopyridine (154 mg, 1.26 mmol), dicyclohexylcarbodiimide (260 mg, 1.26 mmol), [(1S*,2R*)-1-methyl-2-((S*)-5-methylhex-4-en-2-yl)cyclopropyl)]methanol (191 mg, 1.05 mmol) (synthesized by the method described in International Patent Application Publication No. WO2012/160189), and cyclobutanecarboxylic acid (126 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave [(1S*,2R*)-1-methyl-2-((S*)-5-methylhex-4-en-2-yl)cyclopropyl)]methyl cyclobutanecarboxylate (270 mg, 1.02 mmol, yield: 97%).

GC/MS (m/e): 264 (M+, 0.1%), 195(6), 164(8), 149(5), 135(2), 121(19), 109(14), 95(100), 83(46), 69(17), 67(13), 55(87), 41(20), 29(9), 27(5);

$^1$H NMR (CDCl$_3$, 500 MHz) δ −0.01-0.03 (m, 1H), 0.48-0.56 (m, 1H), 0.58 (dd, 1H, J=9.0 Hz, 4.4 Hz), 0.96 (d, 3H, J=6.6 Hz), 1.02-1.10 (m, 1H), 1.12 (s, 3H), 1.60 (s, 3H), 1.71 (d, 3H, J=0.9 Hz), 1.86-2.10 (m, 4H), 2.16-2.25 (m, 2H), 2.25-2.36 (m, 2H), 3.19 (dquin, 1H, J=8.5 Hz, J=1.1 Hz), 3.79 (d, 1H, J=11.1 Hz), 3.83 (d, 1H, J=11.1 Hz), 5.14-5.21 (m, 1H).

$^{13}$C NMR (CDCl$_3$, 500 MHz) δ 175.7 (s), 131.8 (s), 123.0 (d), 73.4 (t), 38.3 (d), 35.7 (t), 34.2 (d), 29.6 (d), 25.8 (q), 25.4 (t), 25.3 (t), 20.1 (s), 19.9 (q), 18.5 (t), 17.8 (q), 16.12 (q), 16.10 (t).

Synthesis Example 35

Synthesis of [(1S*,2R*)-1-Methyl-2-((R*)-5-methylhex-4-en-2-yl)cyclopropyl)]methyl Cyclobutanecarboxylate

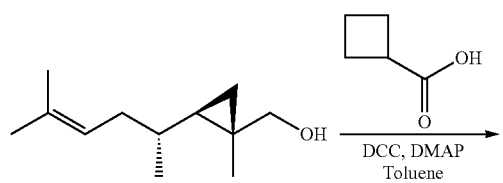

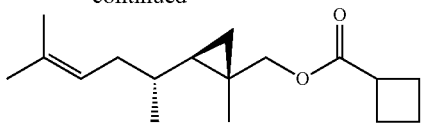

In a nitrogen atmosphere, 5 ml of anhydrous toluene, dimethylaminopyridine (154 mg, 1.26 mmol), dicyclohexylcarbodiimide (260 mg, 1.26 mmol), [(1S*,2R*)-1-methyl-2-((R*)-5-methylhex-4-en-2-yl)cyclopropyl)]methanol (191 mg, 1.05 mmol) (synthesized by the method described in International Patent Application Publication No. WO2012/160189), and cyclobutanecarboxylic acid (126 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chromatography (silica gel, hexane:ethyl acetate=9:1) gave [(1S*,2R*)-1-methyl-2-((R*)-5-methylhex-4-en-2-yl)cyclopropyl)]methyl cyclobutanecarboxylate (263 mg, 0.99 mmol, yield: 95%).

GC/MS (m/e): 264 (M+, 0.1%), 195(3), 181(1), 164(10), 149(8), 135(2), 121(35), 109(7), 107(6), 95(89), 83(61), 69(18), 67(13), 55(100), 41(21), 29(10), 27(5);

$^1$H NMR (CDCl$_3$, 500 MHz) δ 0.09 (dd, 1H, J=5.2 Hz, J=5.2 Hz), 0.47-0.56 (m, 1H), 0.60 (dd, 1H, J=8.9 Hz, 4.7 Hz), 0.93 (d, 3H, J=6.6 Hz), 0.98-1.09 (m, 1H), 1.12 (s, 3H), 1.60 (s, 3H), 1.70 (d, 3H, J=0.8 Hz), 1.86-1.93 (m, 1H), 1.92-2.03 (m, 2H), 2.07-2.15 (m, 1H), 2.16-2.25 (m, 2H), 2.25-2.36 (m, 2H), 3.15 (dquin, 1H, J=8.5 Hz, J=0.8 Hz), 3.78 (d, 1H, J=11.0 Hz), 3.87 (d, 1H, J=11.0 Hz), 5.13-5.20 (m, 1H).

$^{13}$C NMR (CDCl$_3$, 125 MHz) δ 175.7 (s), 132.0 (s), 123.0 (d), 73.4 (t), 38.3 (d), 35.5 (t), 34.6 (d), 29.4 (d), 25.8 (q), 25.4 (t), 25.3 (t), 20.1 (q), 19.2 (s), 18.5 (t), 17.7 (q), 16.8 (t), 15.7 (q).

Synthesis Example 36

Synthesis of [(1R*,2S*)2-((R*)-1-Cyclohexylethyl)-1-methylcyclopropyl)]methanol

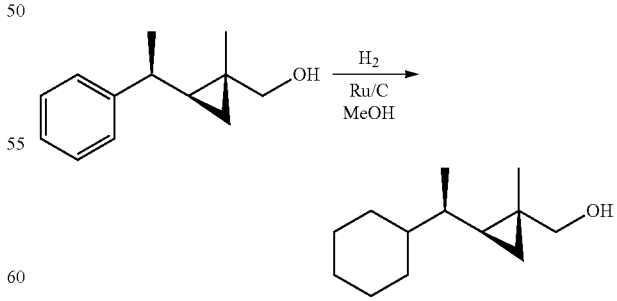

In a 100 ml autoclave, [(1R*,2S*)-1-methyl-2-((S*)-1-phenylethyl)cyclopropyl)]methanol (1.20 g, 6.31 mmol), 24 mg of 20% ruthenium-carbon catalyst, and 24 ml of methanol were placed, and hydrogenation reaction was allowed to proceed under a hydrogen pressure of 2.5 MPa at an oil bath temperature of 140° C. It took 3 hours before the consumption of hydrogen ceased. After cooling, the solvent was evaporated on an evaporator, and subsequent purification by column chromatography (silica gel, hexane:ethyl acetate=1:1) gave [(1R*,2S*)2-((R*)-1-cyclohexylethyl)-1-methylcyclopropyl)]methanol (1.21 g, 6.16 mmol, yield: 98%).

GC/MS (m/e): 196 (M+, 0.2), 178(1), 163(4), 149(3), 141(8), 139(5), 124(48), 109(31), 95(38), 82(100), 69(66), 67(72), 55(73), 43(19), 41(34), 29(21), 27(8).

$^1$H NMR (CDCl$_3$, 500 MHz) δ −0.10−−0.06 (m, 1H), 0.45-0.59 (m, 2H), 0.93 (d, 3H, J=1.3 Hz), 0.86-1.05 (m, 2H), 1.12 (s, 3H), 1.05-1.30 (m, 6H), 1.62-1.70 (m, 2H), 1.70-1.80 (m, 3H), 3.29 (d, 1H, J=10.9 Hz), 3.40 (d, 1H, J=10.9 Hz).

$^{13}$C NMR (CDCl$_3$, 125 MHz) δ 72.5 (t), 43.8 (d), 37.9 (d), 31.1 (t), 29.4 (t), 27.7 (d), 27.0 (t), 26.9 (t), 26.8 (t), 23.7 (s), 17.1 (q), 16.3 (q), 16.4 (t).

Synthesis Example 37

Synthesis of [(1R*,2S*)2-((S*)-1-Cyclohexylethyl)-1-methylcyclopropyl)]methanol

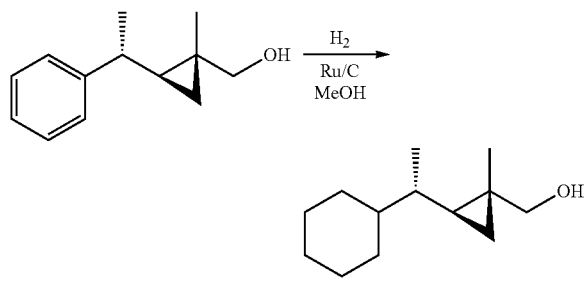

In a 100 ml autoclave, [(1R*,2S*)-1-methyl-2-((R*)-1-phenylethyl)cyclopropyl)]methanol (1.20 g, 6.31 mmol), 24 mg of 20% ruthenium-carbon catalyst, and 24 ml of methanol were placed, and hydrogenation reaction was allowed to proceed under a hydrogen pressure of 2.5 MPa at an oil bath temperature of 140° C. It took 3 hours before the consumption of hydrogen ceased. After cooling, the solvent was evaporated on an evaporator, and subsequent purification by column chromatography (silica gel, hexane:ethyl acetate=1:1) gave [(1R*,2S*)2-((S*)-1-cyclohexylethyl)-1-methylcyclopropyl)]methanol (1.23 g, 6.16 mmol, yield: 99%).

GC/MS (m/e): 196 (M+, 0.4), 178(1), 163(5), 149(4), 141(6), 139(4), 124(39), 113(20), 111(19), 110(37), 109(36), 95(47), 82(100), 69(73), 67(72), 55(91), 43(26), 41(36), 29(23), 27(9).

$^1$H NMR (CDCl$_3$, 500 MHz) δ 0.06-0.11 (m, 1H), 0.43-0.50 (m, 1H), 0.55 (dd, 1H, J=8.8 Hz, J=4.5 Hz), 0.89-0.93 (m, 3H), 1.00-1.31 (m, 8H), 1.14 (s, 3H), 1.63-1.79 (m, 5H), 3.23 (dd, 1H, J=10.8 Hz, J=2.9 Hz), 3.37 (dd, 1H, J=10.8 Hz, J=4.4 Hz).

$^{13}$C NMR (CDCl$_3$, 125 MHz) δ 72.9 (t), 43.9 (d), 38.8 (d), 31.1 (t), 29.8 (t), 27.0 (d), 26.91 (t), 26.85 (t), 26.84 (t), 21.3 (q), 17.7 (s), 17.2 (t), 15.3 (q).

Synthesis Example 38

Synthesis of [(1R*,2S*)-2-((R*)-1-Cyclohexylethyl)-1-methylcyclopropyl)]methyl Propionate

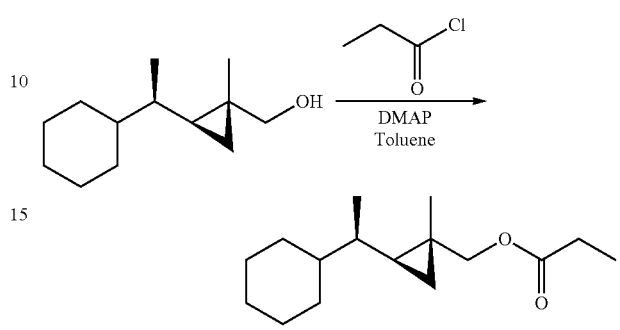

In a nitrogen atmosphere, 5 ml of anhydrous toluene, dimethylaminopyridine (154 mg, 1.26 mmol), and [(1R*,2S*)2-((R*)-1-cyclohexylethyl)-1-methylcyclopropyl)]methanol (206 mg, 1.05 mmol) were placed in a 30 ml flask equipped with a stirrer, a dropping funnel, and a thermometer, and stirred until dissolution. Then, propanoyl chloride (117 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-2-((R*)-1-cyclohexylethyl)-1-methylcyclopropyl)]methyl propionate (245 mg, 0.97 mmol, yield: 93%).

GC/MS (m/e): 252 (M+, 0.1), 196(2), 178(9), 169(4), 163(7), 149(6), 135(10), 124(36), 122(22), 110(43), 95(56), 82(70), 69(37), 67(42), 57(100), 55(54), 41(32), 29(33).

$^1$H NMR (CDCl$_3$, 500 MHz) δ −0.04 (dd, 1H, J=5.5 Hz, J=4.4 Hz), 0.56 (dd, 1H, J=9.3 Hz, J=4.3 Hz), 0.59-0.65 (m, 1H), 0.87-1.07 (m, 3H), 0.91-0.94 (m, 3H), 1.10 (s, 3H), 1.15 (t, 3H, J=7.6 Hz), 1.08-1.27 (m, 4H), 1.62-1.79 (m, 5H), 2.34 (q, 2H, J=7.6 Hz), 3.80 (d, 1H, J=11.0 Hz), 3.88 (d, 1H, J=11.0 Hz).

$^{13}$C NMR (CDCl$_3$, 125 MHz) δ 174.7 (s), 73.7 (t), 43.7 (d), 38.1 (d), 30.9 (t), 29.3 (t), 28.1 (d), 27.7 (t), 27.02 (t), 26.9 (t), 26.8 (t), 20.6 (s), 17.1 (q), 16.8 (q), 15.9 (t), 9.2 (q).

Synthesis Example 39

Synthesis of [(1R*,2S*)-2-((S*)-1-Cyclohexylethyl)-1-methylcyclopropyl)]methyl Propionate

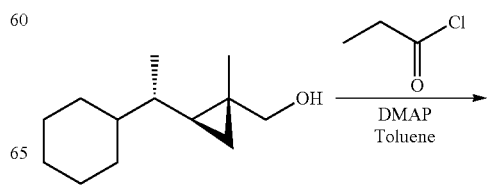

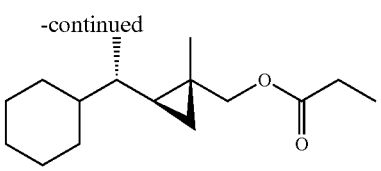

In a nitrogen atmosphere, 5 ml of anhydrous toluene, dimethylaminopyridine (154 mg, 1.26 mmol), and [(1R*,2S*)2-((S*)-1-cyclohexylethyl)-1-methylcyclopropyl)]methanol (206 mg, 1.05 mmol) were placed in a 30 ml flask equipped with a stirrer, a dropping funnel, and a thermometer, and stirred until dissolution. Then, propanoyl chloride (117 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate.

After filtration, the solvent was evaporated on a rotary evaporator, and subsequent purification by column chromatography (silica gel, hexane:ethyl acetate=9:1) gave [(1R*,2S*)-2-((S*)-1-cyclohexylethyl)-1-methylcyclopropyl)]methyl propionate (248 mg, 0.98 mmol, yield: 94%).

GC/MS (m/e): 252 (M+, 0.1), 196(2), 178(9), 169(3), 163(7), 149(5), 135(9), 129(7), 124(32), 122(20), 110(42), 95(56), 82(64), 81(59), 69(36), 67(37), 57(100), 55(52), 41(29), 29(32).

$^1$H NMR (CDCl$_3$, 500 MHz) δ 0.11 (dd, 1H, J=5.2 Hz, J=5.2 Hz), 0.51-0.58 (m, 1H), 0.63 (dd, 1H, J=8.8 Hz, J=4.7 Hz), 0.83-0.92 (m, 1H), 0.87-0.92 (m, 3H), 0.96-1.09 (m, 2H), 1.11 (s, 3H), 1.15 (t, 3H, J=7.6 Hz), 1.12-1.30 (m, 4H), 1.61-1.78 (m, 5H), 2.34 (q, 2H, J=7.6 Hz), 3.79 (d, 1H, J=11.0 Hz), 3.86 (d, 1H, J=11.0 Hz).

$^{13}$C NMR (CDCl$_3$, 125 MHz) δ 174.7 (s), 73.8 (t), 43.9 (d), 38.8 (d), 31.0 (t), 29.9 (t), 27.7 (t), 27.3 (d), 26.9 (t), 26.8 (t), 18.2 (s), 17.7 (t), 17.5 (q), 15.7 (q), 9.2 (q).

Synthesis Example 40

Synthesis of [(1R*,2S*)-2-((R*)-1-Cyclohexylethyl)-1-methylcyclopropyl)]methyl Isobutyrate

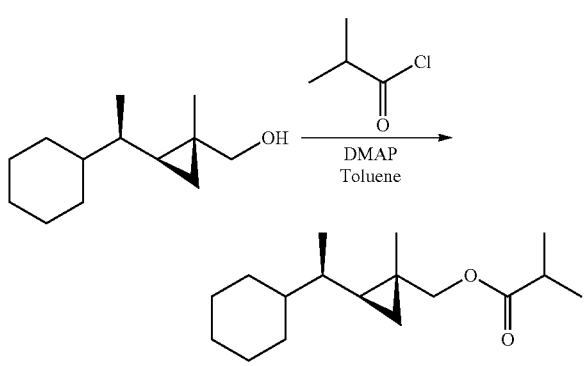

In a nitrogen atmosphere, 5 ml of anhydrous toluene, dimethylaminopyridine (154 mg, 1.26 mmol), and [(1R*,2S*)2-((R*)-1-cyclohexylethyl)-1-methylcyclopropyl)]methanol (206 mg, 1.05 mmol) were placed in a 30 ml flask equipped with a stirrer, a dropping funnel, and a thermometer, and stirred until dissolution. Then, isobutyryl chloride (134 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane:ethyl acetate=9:1) gave [(1R*,2S*)-2-((R*)-1-cyclohexylethyl)-1-methylcyclopropyl)]methyl isobutyrate (271 mg, 1.01 mmol, yield: 97%).

GC/MS (m/e): 266 (M+, 2), 211(1), 196(1), 183(8), 178 (9), 163(8), 149(6), 143(8), 135(11), 124(31), 122(25), 110 (49), 95(70), 82(78), 81(73), 71(100), 69(40), 67(42), 55(69), 43(81), 41(42), 29(10), 27(7).

$^1$H NMR (CDCl$_3$, 500 MHz) δ -0.04 (dd, 1H, J=5.8 Hz, J=4.5 Hz), 0.55 (dd, 1H, J=9.1 Hz, J=4.5 Hz), 0.59-0.66 (m, 1H), 0.87-0.95 (m, 1H), 0.91-0.95 (m, 3H), 0.95-1.17 (m, 2H), 1.10 (s, 3H), 1.18 (d, 6H, J=7.0 Hz), 1.18-1.27 (m, 4H), 1.62-1.69 (m, 1H), 1.69-1.78 (m, 4H), 2.56 (h, 1H, J=7.0 Hz), 3.70 (d, 1H, J=11.0 Hz), 3.93 (d, 1H, J=11.0 Hz).

$^{13}$C NMR (CDCl$_3$, 125 MHz) δ 177.3 (s), 73.7 (t), 43.7 (d), 38.1 (d), 34.2 (d), 30.9 (t), 29.3 (t), 28.3 (d), 27.0 (t), 26.9 (t), 26.8 (t), 20.6 (s), 19.03 (q), 19.00 (q), 17.1 (q), 16.7 (q), 15.8 (t).

Synthesis Example 41

Synthesis of [(1R*,2S*)-2-((S*)-1-Cyclohexylethyl)-1-methylcyclopropyl)]methyl Isobutyrate

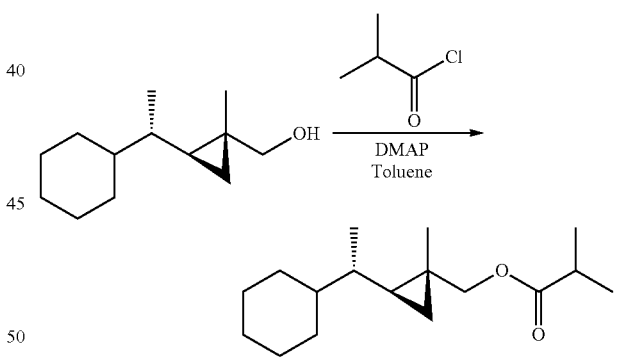

In a nitrogen atmosphere, 5 ml of anhydrous toluene, dimethylaminopyridine (154 mg, 1.26 mmol), and [(1R*,2S*)2-((S*)-1-cyclohexylethyl)-1-methylcyclopropyl)]methanol (206 mg, 1.05 mmol) were placed in a 30 ml flask equipped with a stirrer, a dropping funnel, and a thermometer, and stirred until dissolution. Then, isobutyryl chloride (134 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane: ethyl acetate=9:1) gave [(1R*,2S*)-2-((S*)-1-cyclohexylethyl)-1-methylcyclopropyl)]methyl isobutyrate (268 mg, 1.01 mmol, yield: 96%).

GC/MS (m/e): 266 (M+, 2), 211(1), 196(1), 183(7), 178 (9), 163(7), 149(6), 143(7), 135(10), 124(29), 122(24), 110(52), 95(72), 82(69), 81(65), 71(100), 69(40), 67(39), 55(60), 43(81), 41(40), 29(8), 27(6).

$^1$H NMR (CDCl$_3$, 125 MHz) δ 0.11 (dd, 1H, J=5.4 Hz, J=4.6 Hz), 0.62 (dd, 1H, J=8.8 Hz, J=4.6 Hz), 0.51-0.58 (m, 1H), 0.82-0.92 (m, 1H), 0.88-0.92 (m, 3H), 0.91-1.09 (m, 2H), 1.11 (s, 3H), 1.18 (dd, 6H, J=7.0 Hz, J=2.1 Hz), 1.14-1.29 (m, 4H), 1.61-1.78 (m, 5H), 2.56 (h, 1H, J=7.0 Hz), 3.73 (d, 1H, J=11.0 Hz), 3.90 (d, 1H, J=11.0 Hz).

$^{13}$C NMR (CDCl$_3$, 500 MHz) δ 177.3 (s), 73.7 (t), 43.9 (d), 38.9 (d), 34.2 (d), 31.0 (t), 29.9 (t), 27.4 (d), 26.9 (t), 26.8 (t), 19.1 (q), 19.0 (q), 18.3 (s), 17.6 (t), 17.5 (q), 15.7 (q).

Synthesis Example 42

Synthesis of [(1R*,2S*)-2-((R*)-1-Cyclohexylethyl)-1-methylcyclopropyl)]methyl Cyclopropanecarboxylate

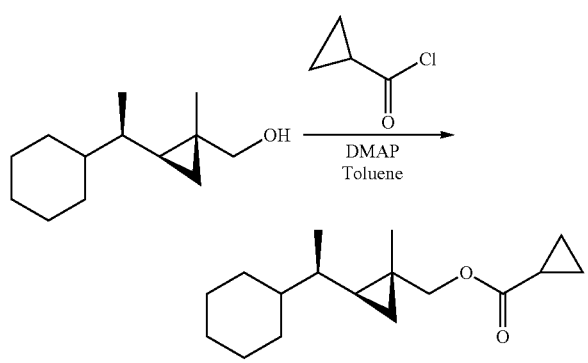

In a nitrogen atmosphere, 5 ml of anhydrous toluene, dimethylaminopyridine (154 mg, 1.26 mmol), and [(1R*,2S*)2-((R*)-1-cyclohexylethyl)-1-methylcyclopropyl)] methanol (206 mg, 1.05 mmol) were placed in a 30 ml flask equipped with a stirrer, a dropping funnel, and a thermometer, and stirred until dissolution. Then, cyclopropanecarbonyl chloride (132 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane: ethyl acetate=9:1) gave [(1R*,2S*)-2-((R*)-1-cyclohexylethyl)-1-methylcyclopropyl)]methyl cyclopropanecarboxylate (264 mg, 1.00 mmol, yield: 95%).

GC/MS (m/e): 266 (M+, 0.1), 181(6), 178(5), 163(4), 149(3), 141(5), 135(6), 124(13), 122(14), 110(25), 95(35), 82(33), 81(35), 69(100), 55(35), 41(35), 29(5), 27(2).

$^1$H NMR (CDCl$_3$, 500 MHz) δ -0.04 (dd, 1H, J=5.6 Hz, J=4.4 Hz), 0.56 (dd, 1H, J=9.1 Hz, J=4.4 Hz), 0.59-0.66 (m, 1H), 0.78-1.07 (m, 3H), 0.82-0.87 (m, 2H), 0.91-0.95 (m, 3H), 0.98-1.02 (m, 2H), 1.11 (s, 3H), 1.14-1.28 (m, 4H), 1.58-1.64 (m, 1H), 1.62-1.79 (m, 5H), 3.78 (d, 1H, J=11.1 Hz), 3.87 (d, 1H, J=11.1 Hz).

$^{13}$C NMR (CDCl$_3$, 125 MHz) δ 175.0 (s), 73.8 (t), 43.7 (d), 38.1 (d), 30.9 (t), 29.3 (t), 28.1 (d), 27.0 (t), 26.9 (t), 26.8 (t), 20.6 (s), 17.1 (q), 16.8 (q), 15.9 (t), 13.0 (d), 8.24 (t), 8.22 (t).

Synthesis Example 43

Synthesis of [(1R*,2S*)-2-((S*)-1-Cyclohexylethyl)-1-methylcyclopropyl)]methyl Cyclopropanecarboxylate

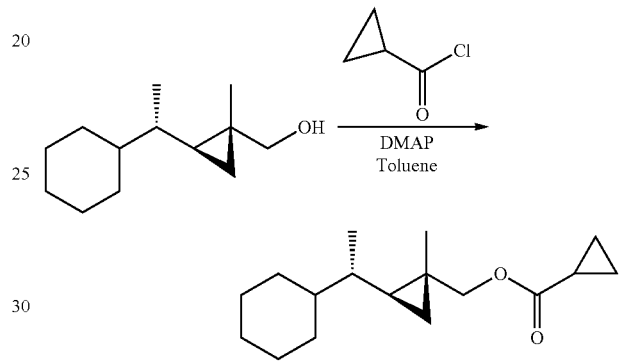

In a nitrogen atmosphere, 5 ml of anhydrous toluene, dimethylaminopyridine (154 mg, 1.26 mmol), and [(1R*,2S*)2-((S*)-1-cyclohexylethyl)-1-methylcyclopropyl)] methanol (206 mg, 1.05 mmol) were placed in a 30 ml flask equipped with a stirrer, a dropping funnel, and a thermometer, and stirred until dissolution. Then, cyclopropanecarbonyl chloride (132 mg, 1.26 mmol) was added dropwise in 5 minutes. After the dropwise addition, the mixture was stirred for 1 hour. After the disappearance of the raw material was observed by thin-layer chromatography, 0.2 ml of methanol was added, followed by stirring for further 30 minutes. The reaction solution was quenched in water, and the organic layer was separated, then washed with water, and dried over anhydrous magnesium sulfate. After filtration, the solvent was evaporated on a rotary evaporator, and subsequent purification by column chromatography (silica gel, hexane: ethyl acetate=9:1) gave [(1R*,2S*)-2-((S*)-1-cyclohexylethyl)-1-methylcyclopropyl)]methyl cyclopropanecarboxylate (263 mg, 0.99 mmol, yield: 95%).

GC/MS (m/e): 266 (M+, 0.1), 181(6), 178(5), 163(4), 149(3), 141(5), 135(6), 124(13), 122(13), 110(26), 95(37), 82(29), 81(31), 69(100), 55(31), 41(34), 29(4), 27(2).

$^1$H NMR (CDCl$_3$, 500 MHz) δ 0.11 (dd, 1H, J=5.3 Hz, J=5.3 Hz), 0.51-0.58 (m, 1H), 0.62 (dd, 1H, J=8.8 Hz, J=4.7 Hz), 0.82-0.87 (m, 2H), 0.85-0.91 (m, 1H), 0.89-0.93 (m, 3H), 0.97-1.02 (m, 2H), 0.97-1.09 (m, 2H), 1.12 (s, 3H), 1.09-1.30 (m, 4H), 1.59-1.66 (m, 1H), 1.64-1.77 (m, 5H), 3.76 (d, 1H, J=11.0 Hz), 3.86 (d, 1H, J=11.0 Hz).

$^{13}$C NMR (CDCl$_3$, 125 MHz) δ 175.1 (s), 74.0 (t), 43.9 (d), 38.8 (d), 31.0 (t), 29.9 (t), 27.3 (d), 26.9 (t), 26.8 (t), 18.2 (s), 17.7 (t), 17.5 (q), 13.0 (d), 8.24 (t), 8.22 (t).

Synthesis Example 44

Synthesis of [(1R*,2S*)-2-((R*)-1-Cyclohexyl-ethyl)-1-methylcyclopropyl)]methyl Cyclobutan-ecarboxylate

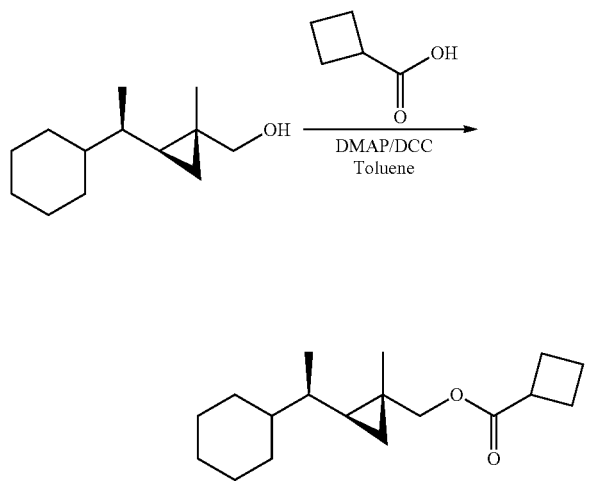

In a nitrogen atmosphere, 5 ml of anhydrous toluene, dimethylaminopyridine (154 mg, 1.26 mmol), dicyclohex-ylcarbodiimide (260 mg, 1.26 mmol), [(1R*,2S*)2-((R*)-1-cyclohexylethyl)-1-methylcyclopropyl)]methanol (206 mg, 1.05 mmol), and cyclobutanecarboxylic acid (126 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chroma-tography (silica gel, hexane:ethyl acetate=9:1) gave [(1R*, 2S*)-2-((R*)-1-cyclohexylethyl)-1-methylcyclopropyl)] methyl cyclobutanecarboxylate (270 mg, 0.97 mmol, yield: 92%).

GC/MS (m/e): 278 (M+, 0.5), 223(1), 195(8), 178(7), 163(7), 155(7), 149(5), 135(9), 124(21), 122(20), 110(39), 95(48), 83(78), 82(45), 81(45), 69(25), 67(28), 55(100), 41(23), 29(10), 27(5).

$^{1}$H NMR (CDCl$_3$, 500 MHz) δ −0.04 (dd, 1H, J=5.7 Hz, J=4.5 Hz), 0.56 (dd, 1H, J=9.1 Hz, J=4.4 Hz), 0.59-0.66 (m, 1H), 0.86-0.94 (m, 1H), 0.91-0.94 (m, 3H), 0.95-1.06 (m, 2H), 1.10 (s, 3H), 1.12-1.27 (m, 4H), 1.62-1.69 (m, 1H), 1.69-1.79 (m, 4H), 1.85-1.96 (m, 1H), 1.89-2.03 (m, 1H), 2.16-2.25 (m, 2H), 2.25-2.37 (m, 2H), 3.14 (quin. d, 1H, J=8.5 Hz, J=1.0 Hz), 3.73 (d, 1H, J=11.1 Hz), 3.92 (d, 1H, J=11.1 Hz).

$^{13}$C NMR (CDCl$_3$, 125 MHz) δ 175.7 (s), 73.7 (t), 43.7 (d), 38.3 (d), 38.1 (d), 30.9 (t), 29.4 (t), 28.2 (d), 27.0 (t), 26.9 (t), 26.8 (t), 25.34 (t), 25.32 (t), 20.6 (s), 18.5 (t), 17.2 (q), 16.7 (q), 15.9 (t).

Synthesis Example 45

Synthesis of [(1R*,2S*)-2-((S*)-1-Cyclohexyl-ethyl)-1-methylcyclopropyl)]m ethyl Cyclobutan-ecarboxylate

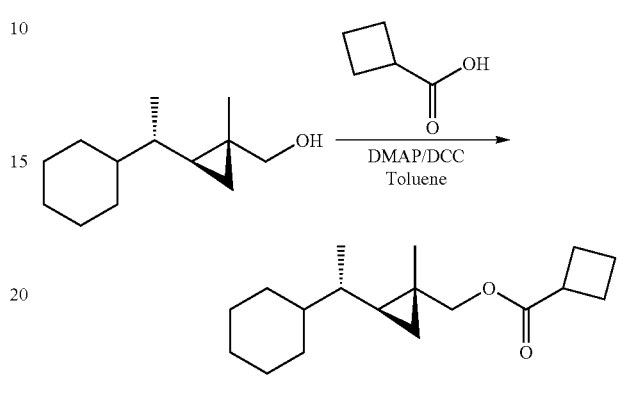

In a nitrogen atmosphere, 5 ml of anhydrous toluene, dimethylaminopyridine (154 mg, 1.26 mmol), dicyclohex-ylcarbodiimide (260 mg, 1.26 mmol), [(1R*,2S*)-2-((S*)-1-cyclohexylethyl)-1-methylcyclopropyl)]methanol (206 mg, 1.05 mmol), and cyclobutanecarboxylic acid (126 mg, 1.26 mmol) were placed in a 30 ml flask equipped with a stirrer, a dropping funnel, and a thermometer, and stirred for 1 hour. After the disappearance of the raw material was observed by thin-layer chromatography, 0.2 ml of methanol and 0.2 ml of acetic acid were added, followed by stirring for further 30 minutes. The reaction solution was filtered, then washed with water, and dried over anhydrous magnesium sulfate. After filtration, the solvent was evaporated on a rotary evaporator, and subsequent purification by column chroma-tography (silica gel, hexane:ethyl acetate=9:1) gave [(1R*, 2S*)-2-((S*)-1-cyclohexylethyl)-1-methylcyclopropyl)]m ethyl cyclobutanecarboxylate (274 mg, 0.98 mmol, yield: 94%).

GC/MS (m/e): 278 (M+, 0.3), 195(7), 178(8), 163(6), 155(6), 149(5), 135(8), 124(21), 122(19), 110(41), 95(50), 83(75), 82(43), 81(42), 69(25), 67(26), 55(100), 41(22), 29(10), 27(4).

$^{1}$H NMR (CDCl$_3$, 500 MHz) δ 0.11 (dd, 1H, J=5.3 Hz, J=5.1 Hz), 0.51-0.58 (m, 1H), 0.63 (dd, 1H, J=8.7 Hz, J=4.7 Hz), 0.82-0.91 (m, 1H), 0.88-0.92 (m, 3H), 0.91-1.09 (m, 2H), 1.11 (s, 3H), 1.16-1.30 (m, 4H), 1.61-1.68 (m, 1H), 1.67-1.78 (m, 4H), 1.85-1.96 (m, 1H), 1.90-2.02 (m, 1H), 2.15-2.25 (m, 2H), 2.24-2.36 (m, 2H), 3.15 (quin. d, 1H, J=8.5 Hz, J=1.0 Hz), 3.77 (d, 1H, J=11.0 Hz), 3.88 (d, 1H, J=11.0 Hz).

$^{13}$C NMR (CDCl$_3$, 125 MHz) δ 175.7 (s), 73.7 (t), 43.9 (d), 38.8 (d), 38.3 (d), 31.0 (t), 29.9 (t), 27.3 (d), 26.9 (t), 26.8 (t), 25.4 (t), 25.3 (t), 18.5 (t), 18.3 (s), 17.7 (t), 17.5 (q), 15.7 (q).

[Evaluation of Odor Quality]

The compounds synthesized in Synthesis Examples 16 to 35 and 38 to 45 above were evaluated in terms of odor quality. The results are classified by the odor quality and shown in Tables 10 to 14.

TABLE 10

| | Structural formula | Odor quality |
|---|---|---|
| [Synthesis Example 16] (Example Compound 32) | | Musky, Fruity, Floral, Woody Very nice Fruity-Musk |
| [Synthesis Example 17] (Example Compound 32) | | Floral, Woody, Green, Fruity Not Musk note but Floral |
| [Synthesis Example 18] (Example Compound 34) | | Fruity, Green, Floral, Acid Sweet Fruity-Green with Acidic |
| [Synthesis Example 20] (Example Compound 53) | | Floral, Musky, Woody, Green Nice Floral-Musk |
| [Synthesis Example 22] (Example Compound 54) | | Musky, Floral, Powdery, Animal Most Musky character |
| [Synthesis Example 19] (Example Compound 34) | | Floral, Musky, Fruity, Acid Weak and Acidic, less substantive |

TABLE 11

| | Structural formula | Odor quality |
|---|---|---|
| [Synthesis Example 21] (Example Compound 53) | | Floral, Green, Musky, Woody Weak with Floral-Musk tone |
| [Synthesis Example 23] (Example Compound 54) | | Green, Floral, Fruity, Citrus Fresh Citrus-Floral not substantive |
| [Synthesis Example 26] (Example Compound 46) | | Musky, Green, Floral, Fruity Nice Light Fresh Musk |

TABLE 11-continued

| | Structural formula | Odor quality |
|---|---|---|
| [Synthesis Example 28] (Example Compound 47) | | Floral, Green, Musky, Woody Weak Green-Floral Musk |
| [Synthesis Example 27] (Example Compound 46) | | Green, Floral, Woody, Metallic Green-Floral with Chemical tone |
| [Synthesis Example 29] (Example Compound 47) | | Floral, Woody, Balsamic, Musk Very Weak |

TABLE 12

| | Structural formula | Odor quality |
|---|---|---|
| [Synthesis Example 25] (Example Compound 252) | | Green, Fruity, Musky, Rhubarb Fruity-Green Musk, |
| [Synthesis Example 30] (Example Compound 254) | | Floral, Musky, Woody, Amber Weak, not so characteristic |
| [Synthesis Example 32] (Example Compound 257) | | Floral, Woody, Musky, Herbal Weak a bit green |
| [Synthesis Example 24] (Example Compound 252) | | Floral, Woody, Fruity, Musky Fruity-Green Musk, |
| [Synthesis Example 31] (Example Compound 254) | | Floral, Musky, Woody, Herbal Weak, not so characteristic |

TABLE 13

| | Structural formula | Odor quality |
|---|---|---|
| [Synthesis Example 33] (Example Compound 257) | | Floral, Musky, Green, Woody Weak a bit green |
| [Synthesis Example 34] (Example Compound 258) | | Floral, Musky, Green, Woody Weak not interesting |
| [Synthesis Example 35] (Example Compound 258) | | Floral, Musky, Green, Fruity Less characteristic |

TABLE 14

| | Structural formula | Odor quality |
|---|---|---|
| [Synthesis Example 38] (Example Compound 152) | | Musky, Animal, Powdery, Floral Very strong, Animalic Musk |
| [Synthesis Example 40] (Example Compound 154) | | Musky, Floral, Woody, Animal Weak, Less characteristic |
| [Synthesis Example 42] (Example Compound 157) | | Musky, Floral, Green, Woody Rather weak but good Musk |
| [Synthesis Example 44] (Example Compound 158) | | Musky, Fruity, Floral, Green Weak, Very light, Fruity Floral |
| [Synthesis Example 39] (Example Compound 152) | | Floral, Fruity, Green, Musky Very diffusive, Not Musky Green Floral |
| [Synthesis Example 41] (Example Compound 154) | | Musky, Floral, Woody, Powdery Weak, less substantive |

TABLE 14-continued

| | Structural formula | Odor quality |
|---|---|---|
| [Synthesis Example 43] (Example Compound 157) | | Musky, Floral, Woody, Fruity Verdox like, Fruity Woody |
| [Synthesis Example 45] (Example Compound 158) | | Floral, Fruity, Woody, Musky Not looks like Musk |

Example 1: Fragrance Compositions with Muguet Note

Fragrance compositions for perfume were prepared by using the compounds synthesized in Synthesis Example 16, 20, 22, and 26 according to the recipe shown in Table 15 below.

TABLE 15

| Component | Parts by mass |
|---|---|
| Amyl cinnamic aldehyde | 50 |
| Benzyl acetate | 50 |
| l-Citronellol | 3 |
| Citronellol | 100 |
| Dihydromyrcenol | 30 |
| Dimethyl phenylethyl carbinol | 50 |
| Hexyl cinnamic aldehyde | 100 |
| Indole | 2 |
| Linalool | 100 |
| Phenylacetaldehyde dimethyl acetal | 10 |
| Phenylethyl alcohol | 150 |
| SANTALEX T (registered trademark) (manufactured by Takasago International Corporation) | 25 |
| Terpineol | 30 |
| Compound of Synthesis Example 16, 20, 22, or 26 | 300 |
| Total | 1000 |

Sensory evaluation was conducted by four professional panelists each having a five-year experience or more. The results were that all the panelists found that the fragrance compositions with muguet note each containing one of the compounds synthesized in Synthesis Example 16, 20, 22, and 26 were excellent.

Example 2: Fragrance Compositions with Marine Note

Fragrance compositions for perfume were prepared by using the compounds synthesized in Synthesis Example 16, 20, 22, and 26 according to the recipe shown in Table 16 below.

TABLE 16

| Component | Parts by mass |
|---|---|
| CALONE (registered trademark) (manufactured by Firmenich) | 10 |

TABLE 16-continued

| Component | Parts by mass |
|---|---|
| Canthoxal | 10 |
| γ-Decalactone | 30 |
| β-Dihydroionone | 50 |
| Eugenol | 5 |
| HEDIONE (registered trademark) (manufactured by Firmenich) | 250 |
| HELIOBOUQUET (registered trademark) (manufactured by Takasago International Corporation) | 40 |
| cis-3-Hexenyl salicylate | 15 |
| l-Citronellol | 40 |
| Linalool | 50 |
| l-Muscone (manufactured by Takasago International Corporation) | 40 |
| MUSK T (registered trademark) (manufactured by Takasago International Corporation) | 200 |
| ORBITONE (registered trademark) (manufactured by Takasago International Corporation) | 150 |
| THESARON (registered trademark) (manufactured by Takasago International Corporation) | 10 |
| Compound of Synthesis Example 16, 20, 22, or 26 | 100 |
| Total | 1000 |

Sensory evaluation was conducted by four professional panelists each having a five-year experience or more. The results were that all the panelists found that the fragrance compositions with marine note each containing one of the compounds synthesized in Synthesis Example 16, 20, 22, and 26 had distinct marine and ozone nuances and were also excellent in diffusibility.

Example 3: Fragrance Compositions with Floral Note

Fragrance compositions for perfume were prepared by using the compounds synthesized in Synthesis Examples 16, 20, 22, and 26 according to the recipe shown in Table 17 below.

TABLE 17

| Component | Parts by mass |
|---|---|
| Allyl caproate | 14 |
| L-Citronellyl nitrile (manufactured by Takasago International Corporation) | 6 |

TABLE 17-continued

| Component | Parts by mass |
|---|---|
| CYCLAPROP (registered trademark) (manufactured by International Flavors & Fragrances) | 30 |
| α-Damascone | 12 |
| Ethyl 2-methylbutyrate | 10 |
| Ethyl methyl-phenylglycidate | 8 |
| Eugenol | 2 |
| FRUITATE (registered trademark) (manufactured by Kao Corporation) | 10 |
| Geranyl acetate | 16 |
| HEDIONE (registered trademark) (manufactured by Firmenich) | 100 |
| HELIOBOUQUET (registered trademark) (manufactured by Takasago International Corporation) | 6 |
| cis-3-Hexenol | 2 |
| Hexyl acetate | 30 |
| Hexyl cinnamic aldehyde | 70 |
| Hexyl salicylate | 50 |
| HINDINOL (registered trademark) (manufactured by Takasago International Corporation) | 8 |
| cis-Jasmon | 1 |
| Linalyl acetate | 10 |
| Orange oil | 50 |
| L-ORANTHA SUPER (registered trademark) @1.0% in DPG (manufactured by Takasago International Corporation) | 6 |
| ORBITONE (registered trademark) (manufactured by Takasago International Corporation) | 20 |
| PEONILE (registered trademark) (manufactured by Givaudan) | 14 |
| PHENOXANOL (registered trademark) (manufactured by International Flavors & Fragrances) | 20 |
| Raspberry ketone | 36 |
| ROSYRANE SUPER@1.0% in DPG (manufactured by Givaudan) | 4 |
| Tetrahydrolinalool | 100 |
| TRIPLAL (registered trademark) (manufactured by International Flavors & Fragrances) | 4 |
| γ-Undecalactone | 20 |
| VERDOX (manufactured by International Flavors & Fragrances) | 60 |
| Yara yara | 2 |
| Dipropylene glycol | 209 |
| Compound of Synthesis Example 16, 20, 22, or 26 | 70 |
| Total | 1000 |

Sensory evaluation was conducted by four professional panelists each having a five-year experience or more. The results were that all the panelists found that the fragrance compositions with floral note each containing one of the compound synthesized in Synthesis Example 16, 20, 22, and 26 were excellent.

Example 4: Liquid Detergents

Liquid detergents (100 g) were prepared each of which was scented with one of the fragrance compositions of Example 3 at 0.5% according to the recipe shown in Table 18 below.

TABLE 18

| Component | Blended amount (g) |
|---|---|
| Polyoxyalkylene alkyl ether | 50.00 |
| Purified water | 35.13 |
| Butyl carbitol | 8.00 |
| Linear alkylbenzenesulfonate | 2.50 |
| p-Toluenesulfonic acid | 1.00 |
| Polyethylene glycol | 1.00 |
| Monoethanolamine | 1.00 |
| Coconut fatty acid | 0.10 |
| Citric acid | 0.22 |
| Sodium benzoate | 0.50 |
| BHT | 0.50 |
| Fragrance composition of Example 3 | 0.50 |
| Total | 100.00 |

Sensory evaluation was conducted by four professional panelists each having a five-year experience or more. The results were that all the panelists found that the liquid detergents each blended with one of the fragrance compositions of Example 3, which were fragrance compositions each containing one of the compounds synthesized in Synthesis Examples 16, 20, 22, and 26, had excellent odor.

Example 5: Shampoos

Shampoos (100 g) were prepared each of which was scented with one of the fragrance compositions of Examples 1, 2, and 3 at 1.0% according to the recipe shown in Table 19 below.

TABLE 19

| Component | Blended amount (g) |
|---|---|
| Sodium polyoxyethylene lauryl ether sulfate | 14.00 |
| Lauramidopropyl betaine | 4.00 |
| Coconut fatty acid diethanolamide | 3.00 |
| Cationic cellulose | 0.50 |
| Ethylene glycol distearate | 1.00 |
| Ethyl para-hydroxybenzoate | 0.25 |
| Citric acid | quantum sufficit |
| Fragrance composition of Example 1, 2, or 3 | 1.00 |
| Purified water | the balance |
| Total | 100.00 |

Sensory evaluation was conducted by four professional panelists each having a five-year experience or more. The results were that all the panelists found that the shampoos each blended with one of the fragrance compositions of Examples 1, 2, and 3, which were fragrance compositions each containing one of the compounds synthesized in Synthesis Examples 16, 20, 22, and 26, had excellent odor.

Example 6: Body Shampoos

Body shampoos (100 g) were prepared each of which was scented with the fragrance compositions of Example 1, 2, or 3 at 0.95% according to the recipe shown in Table 20 below.

TABLE 20

| Component | Blended amount (g) |
|---|---|
| Triethanolamine | 9.00 |
| Lauric acid | 6.00 |
| Myristic acid | 9.00 |
| Disodium lauryl polyoxyethylene sulfosuccinate (1E.O.) (42%) | 10.00 |
| Alkyl(C8-16)glucoside | 8.00 |
| Glyceryl laurate | 1.00 |
| 2-Hydroxyethyl distearate | 2.50 |

TABLE 20-continued

| Component | Blended amount (g) |
|---|---|
| Coconut fatty acid diethanolamide | 3.00 |
| Polyoxypropylene glycol | 5.00 |
| Dibutylhydroxytoluene | 0.05 |
| Disodium edetate | 0.10 |
| Ethyl para-hydroxybenzoate | 0.20 |
| Methyl para-hydroxybenzoate | 0.10 |
| Fragrance composition of Example 1, 2, or 3 | 0.95 |
| Purified water | the balance |
| Total | 100.00 |

Sensory evaluation was conducted by four professional panelists each having a five-year experience or more. The results were that all the panelists found that the body shampoos each blended with one of the fragrance compositions of Example 1, 2, and 3, which were the fragrance compositions each containing one of the compounds synthesized in Synthesis Example 16, 20, 22, and 26, had excellent odor.

The invention claimed is:

1. A compound of the following general formula (1):

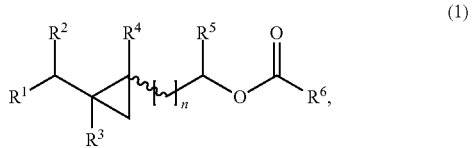

wherein

R$^1$ is an alkenyl group having 2 to 9 carbon atoms, a cycloalkyl group having 3 to 10 carbon atoms which may have a substituent, or a phenyl group which may have a substituent, R$^2$ is an alkyl group having 1 to 3 carbon atoms, R$^3$ to R$^5$ are each independently a hydrogen atom or an alkyl group having 1 to 3 carbon atoms, R$^6$ is an alkyl group having 1 to 5 carbon atoms, an alkenyl group having 2 to 5 carbon atoms, a cycloalkyl group having 3 to 10 carbon atoms which may have a substituent, or an alkoxy group having 1 to 5 carbon atoms, n is 0 or 1, and the wavy line means that the compound is a cis isomer, a trans isomer, or a mixture of cis and trans isomers.

2. A flavor and/or fragrance composition comprising the compound according to claim 1.

3. A beverage, food, cosmetic, toiletry product, air-care product, oral cavity composition, hair-care product, skin-care product, body-care product, laundry detergent, finishing softener for clothes, quasi drug, or drug comprising the flavor and/or fragrance composition according to claim 2.

4. A method for improving an odor of a flavor and/or fragrance, the method comprising adding the compound according to claim 1 to the flavor and/or fragrance.

5. The compound according to claim 1, wherein R$^3$ is a hydrogen atom.

6. A flavor and/or fragrance composition comprising the compound according to claim 5.

7. A beverage, food, cosmetic, toiletry product, air-care product, oral cavity composition, hair-care product, skin-care product, body-care product, laundry detergent, finishing softener for clothes, quasi drug, or drug comprising the flavor and/or fragrance composition according to claim 6.

8. A method for improving an odor of a flavor and/or fragrance, the method comprising adding the compound according to claim 5 to the flavor and/or fragrance.

* * * * *